(12) United States Patent
Whitman et al.

(10) Patent No.: US 9,247,940 B2
(45) Date of Patent: Feb. 2, 2016

(54) SURGICAL CUTTING AND STAPLING DEVICE

(71) Applicant: Covidien LP, Mansfield, MA (US)

(72) Inventors: Michael P. Whitman, New Hope, PA (US); David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/755,055

(22) Filed: Jun. 30, 2015

(65) Prior Publication Data

US 2015/0297220 A1    Oct. 22, 2015

Related U.S. Application Data

(62) Division of application No. 13/207,585, filed on Aug. 11, 2011, now abandoned, which is a division of application No. 10/785,672, filed on Feb. 23, 2004, now Pat. No. 8,025,199.

(51) Int. Cl.
| | |
|---|---|
| *A61B 17/064* | (2006.01) |
| *A61B 17/068* | (2006.01) |
| *A61B 17/115* | (2006.01) |
| *A61B 17/3205* | (2006.01) |
| *A61B 17/32* | (2006.01) |
| *A61B 17/072* | (2006.01) |

(52) U.S. Cl.
CPC .............. *A61B 17/068* (2013.01); *A61B 17/115* (2013.01); *A61B 17/32053* (2013.01); *A61B 2017/07285* (2013.01); *A61B 2017/320052* (2013.01)

(58) Field of Classification Search
CPC ................. A61B 17/1155; A61B 2017/00477; A61B 2019/4857; A61B 2017/07214; A61B 17/064; A61B 17/068
USPC ....................... 227/179.1, 175.1, 176.1, 180.1
See application file for complete search history.

(56) References Cited

U.S. PATENT DOCUMENTS

| | | | |
|---|---|---|---|
| 1,798,902 | A | 3/1931 | Raney |
| 1,881,250 | A | 10/1932 | Tomlinson |
| 2,031,682 | A | 2/1936 | Wappler et al. |

(Continued)

FOREIGN PATENT DOCUMENTS

| | | | |
|---|---|---|---|
| DE | 2330182 | A1 | 1/1975 |
| DE | 3114135 | A1 | 10/1982 |

(Continued)

OTHER PUBLICATIONS

New York Magazine, Jun. 10, 2002 The Best Doctors in New York, p. 80.

*Primary Examiner* — Michelle Lopez

(57) ABSTRACT

The present invention, in accordance with various embodiments thereof, relates to a surgical device for at least one of cutting and stapling a section of tissue. The surgical device includes a housing including at least two drivers. The surgical device also includes an anvil mechanically attachable to the housing and moveable relative to the housing between an open position and a closed position. The first driver operates to move the anvil relative to the housing to an intermediate position between the open position and the closed position. The second driver operates to move at least a portion of the housing relative to the anvil between the intermediate position and the closed position.

17 Claims, 33 Drawing Sheets

(56) References Cited

U.S. PATENT DOCUMENTS

| | | |
|---|---|---|
| 2,174,219 A | 9/1939 | Balma |
| 2,246,647 A | 6/1941 | Vancura |
| 2,419,045 A | 4/1947 | Whittaker |
| 2,725,628 A | 12/1955 | O'Neilly et al. |
| 3,079,606 A | 3/1963 | Bobrov et al. |
| 3,120,845 A | 2/1964 | Homer |
| 3,193,165 A | 7/1965 | Akhalaya et al. |
| 3,252,643 A | 5/1966 | Strekopov et al. |
| 3,253,643 A | 5/1966 | Gudheim |
| 3,256,875 A | 6/1966 | Tsepelev et al. |
| 3,275,211 A | 9/1966 | Hirsch et al. |
| 3,315,863 A | 4/1967 | O'Dea |
| 3,317,105 A | 5/1967 | Astafjev et al. |
| 3,388,847 A | 6/1968 | Kasulin et al. |
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,568,659 A | 3/1971 | Karnegis |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green et al. |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles |
| 3,858,577 A | 1/1975 | Bass et al. |
| 3,859,986 A | 1/1975 | Okada et al. |
| 3,882,854 A | 5/1975 | Hulka et al. |
| 3,892,228 A | 7/1975 | Mitsui |
| 3,935,981 A | 2/1976 | Akopov et al. |
| 3,945,375 A | 3/1976 | Banko |
| 3,949,924 A | 4/1976 | Green |
| 3,952,748 A | 4/1976 | Kaliher et al. |
| RE28,932 E | 8/1976 | Noiles et al. |
| 3,990,453 A | 11/1976 | Douvas et al. |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,261,244 A | 4/1981 | Becht et al. |
| 4,273,111 A | 6/1981 | Tsukaya |
| 4,273,129 A | 6/1981 | Boebel |
| 4,286,585 A | 9/1981 | Ogawa |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,351,466 A | 9/1982 | Noiles |
| 4,354,628 A | 10/1982 | Green |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,423,730 A | 1/1984 | Gabbay |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,534,352 A | 8/1985 | Korthoff |
| 4,534,420 A | 8/1985 | Goldelius |
| 4,535,773 A | 8/1985 | Yoon |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| D286,567 S | 11/1986 | Lichtman et al. |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,654,030 A | 3/1987 | Moll et al. |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,682,596 A | 7/1987 | Bales et al. |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,715,502 A | 12/1987 | Salmon |

(56) References Cited

U.S. PATENT DOCUMENTS

| | | |
|---|---|---|
| 4,728,020 A | 3/1988 | Green et al. |
| 4,729,763 A | 3/1988 | Henrie |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,763,669 A | 8/1988 | Jaeger |
| 4,767,044 A | 8/1988 | Green |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,789,090 A | 12/1988 | Blake, III |
| 4,796,793 A | 1/1989 | Smith et al. |
| 4,805,823 A | 2/1989 | Rothfuss |
| 4,815,469 A | 3/1989 | Cohen et al. |
| 4,817,847 A | 4/1989 | Redtenbacher et al. |
| 4,819,632 A | 4/1989 | Davies |
| 4,819,853 A | 4/1989 | Green |
| 4,841,888 A | 6/1989 | Mills et al. |
| 4,848,637 A | 7/1989 | Pruitt |
| 4,858,608 A | 8/1989 | McQuilkin |
| 4,863,088 A | 9/1989 | Redmond et al. |
| 4,867,158 A | 9/1989 | Sugg |
| 4,869,415 A | 9/1989 | Fox |
| 4,873,977 A | 10/1989 | Avant et al. |
| 4,887,599 A | 12/1989 | Muller |
| 4,887,612 A | 12/1989 | Esser et al. |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,902,280 A | 2/1990 | Lander |
| 4,903,697 A | 2/1990 | Resnick et al. |
| 4,907,591 A | 3/1990 | Vasconcellos et al. |
| 4,917,114 A | 4/1990 | Green et al. |
| 4,919,152 A | 4/1990 | Ger |
| 4,928,699 A | 5/1990 | Sasai |
| 4,930,494 A | 6/1990 | Takehana et al. |
| 4,932,960 A | 6/1990 | Green et al. |
| 4,936,845 A | 6/1990 | Stevens |
| 4,940,468 A | 7/1990 | Petillo |
| 4,941,454 A | 7/1990 | Wood et al. |
| 4,941,623 A | 7/1990 | Pruitt |
| 4,943,277 A | 7/1990 | Bolling |
| 4,944,093 A | 7/1990 | Falk |
| 4,944,443 A | 7/1990 | Oddsen et al. |
| 4,955,882 A | 9/1990 | Hakky |
| 4,955,959 A | 9/1990 | Tompkins et al. |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,977,900 A | 12/1990 | Fehling et al. |
| 4,978,049 A | 12/1990 | Green |
| 4,982,726 A | 1/1991 | Taira |
| 4,991,764 A | 2/1991 | Mericle |
| 4,994,060 A | 2/1991 | Rink et al. |
| 4,995,877 A | 2/1991 | Ams et al. |
| 5,005,749 A | 4/1991 | Aranyi |
| 5,018,657 A | 5/1991 | Pedlick et al. |
| 5,030,206 A | 7/1991 | Lander |
| 5,031,814 A | 7/1991 | Tompkins et al. |
| 5,037,379 A | 8/1991 | Clayman et al. |
| 5,040,715 A | 8/1991 | Green et al. |
| 5,047,026 A | 9/1991 | Rydell |
| 5,059,203 A | 10/1991 | Husted |
| 5,065,929 A | 11/1991 | Schulze et al. |
| D322,143 S | 12/1991 | Spreckelmeier |
| 5,071,430 A | 12/1991 | de Salis et al. |
| 5,077,506 A | 12/1991 | Krause |
| 5,084,045 A | 1/1992 | Helenowski |
| 5,100,041 A | 3/1992 | Storace |
| 5,104,025 A | 4/1992 | Main et al. |
| 5,108,391 A | 4/1992 | Flachenecker et al. |
| 5,114,065 A | 5/1992 | Storace |
| 5,119,983 A | 6/1992 | Green et al. |
| 5,129,570 A | 7/1992 | Schulze et al. |
| 5,133,359 A | 7/1992 | Kedem |
| 5,133,360 A | 7/1992 | Spears |
| 5,133,713 A | 7/1992 | Huang et al. |
| 5,139,513 A | 8/1992 | Segato |
| 5,143,082 A | 9/1992 | Kindberg et al. |
| 5,156,315 A | 10/1992 | Green et al. |
| 5,156,614 A | 10/1992 | Green et al. |
| 5,158,222 A | 10/1992 | Green et al. |
| 5,170,925 A | 12/1992 | Madden et al. |
| 5,171,247 A | 12/1992 | Hughett et al. |
| 5,171,251 A | 12/1992 | Bregen et al. |
| 5,173,133 A | 12/1992 | Morin et al. |
| 5,176,687 A | 1/1993 | Hasson et al. |
| 5,186,714 A | 2/1993 | Boudreault et al. |
| 5,190,542 A | 3/1993 | Nakao et al. |
| 5,192,292 A | 3/1993 | Cezana et al. |
| 5,197,649 A | 3/1993 | Bessler et al. |
| 5,197,968 A | 3/1993 | Clement |
| 5,201,325 A | 4/1993 | McEwen et al. |
| 5,201,750 A | 4/1993 | Hocherl et al. |
| 5,205,459 A | 4/1993 | Brinkerhoff et al. |
| 5,207,684 A | 5/1993 | Nobles |
| 5,207,691 A | 5/1993 | Nardella |
| 5,207,697 A | 5/1993 | Carusillo et al. |
| 5,215,521 A | 6/1993 | Cochran et al. |
| 5,217,003 A | 6/1993 | Wilk |
| 5,217,030 A | 6/1993 | Yoon |
| 5,217,460 A | 6/1993 | Knoepfler |
| 5,221,279 A | 6/1993 | Cook et al. |
| 5,221,281 A | 6/1993 | Klicek |
| 5,224,951 A | 7/1993 | Freitas |
| 5,226,426 A | 7/1993 | Yoon |
| 5,234,439 A | 8/1993 | Wilk et al. |
| 5,237,884 A | 8/1993 | Seto |
| 5,243,967 A | 9/1993 | Hibino |
| 5,249,583 A | 10/1993 | Mallaby |
| 5,253,793 A | 10/1993 | Green et al. |
| 5,254,117 A | 10/1993 | Rigby et al. |
| 5,256,149 A | 10/1993 | Banik et al. |
| 5,258,004 A | 11/1993 | Bales et al. |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,609 A | 1/1994 | Pingleton et al. |
| 5,279,565 A | 1/1994 | Klein et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,290,303 A | 3/1994 | Pingleton et al. |
| 5,292,053 A | 3/1994 | Bilotti et al. |
| 5,295,990 A | 3/1994 | Levin |
| 5,300,087 A | 4/1994 | Knoepfler |
| 5,307,976 A | 5/1994 | Olson et al. |
| 5,312,023 A | 5/1994 | Green et al. |
| 5,312,416 A | 5/1994 | Spaeth et al. |
| 5,312,434 A | 5/1994 | Crainich |
| 5,318,221 A | 6/1994 | Green et al. |
| 5,320,627 A | 6/1994 | Sorensen et al. |
| 5,322,055 A | 6/1994 | Davison et al. |
| 5,324,288 A | 6/1994 | Billings et al. |
| 5,324,300 A | 6/1994 | Elias et al. |
| 5,326,013 A | 7/1994 | Green et al. |
| 5,330,471 A | 7/1994 | Eggers |
| 5,330,483 A | 7/1994 | Heaven et al. |
| 5,330,486 A | 7/1994 | Wilk |
| 5,333,772 A | 8/1994 | Rothfuss et al. |

(56) References Cited

U.S. PATENT DOCUMENTS

| | | |
|---|---|---|
| 5,333,773 A | 8/1994 | Main et al. |
| 5,336,229 A | 8/1994 | Noda |
| 5,336,237 A | 8/1994 | Chin et al. |
| 5,342,299 A | 8/1994 | Snoke et al. |
| 5,342,381 A | 8/1994 | Tidemand |
| 5,342,382 A | 8/1994 | Brinkerhoff et al. |
| 5,344,420 A | 9/1994 | Hilal et al. |
| 5,346,497 A | 9/1994 | Simon et al. |
| 5,350,104 A | 9/1994 | Main et al. |
| 5,352,222 A | 10/1994 | Rydell |
| 5,352,223 A | 10/1994 | McBrayer et al. |
| 5,352,235 A | 10/1994 | Koros et al. |
| 5,354,266 A | 10/1994 | Snoke |
| 5,354,303 A | 10/1994 | Spaeth et al. |
| 5,356,408 A | 10/1994 | Rydell |
| 5,358,496 A | 10/1994 | Ortiz et al. |
| 5,358,506 A | 10/1994 | Green et al. |
| 5,364,001 A | 11/1994 | Bryan |
| 5,364,409 A | 11/1994 | Kuwabara et al. |
| 5,366,133 A | 11/1994 | Geiste |
| 5,366,476 A | 11/1994 | Noda |
| 5,368,015 A | 11/1994 | Wilk |
| 5,368,607 A | 11/1994 | Freitas |
| 5,380,321 A | 1/1995 | Yoon |
| 5,383,880 A | 1/1995 | Hooven |
| 5,387,196 A | 2/1995 | Green et al. |
| 5,389,098 A | 2/1995 | Tsuruta et al. |
| 5,391,156 A | 2/1995 | Hildwein et al. |
| 5,395,030 A | 3/1995 | Kuramoto et al. |
| 5,395,033 A | 3/1995 | Byrne et al. |
| 5,395,369 A | 3/1995 | McBrayer et al. |
| 5,396,900 A | 3/1995 | Slater et al. |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Yates et al. |
| 5,403,326 A | 4/1995 | Harrison et al. |
| 5,403,327 A | 4/1995 | Thornton et al. |
| 5,409,487 A | 4/1995 | Jalbert et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,425,705 A | 6/1995 | Evard et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,437,684 A | 8/1995 | Calabrese et al. |
| 5,441,507 A | 8/1995 | Wilk |
| 5,443,198 A | 8/1995 | Viola et al. |
| 5,454,825 A | 10/1995 | Van Leeuwen et al. |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,482,054 A | 1/1996 | Slater et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,496,317 A | 3/1996 | Goble et al. |
| 5,514,134 A | 5/1996 | Rydell et al. |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,529,235 A | 6/1996 | Boiarski et al. |
| 5,531,687 A | 7/1996 | Snoke et al. |
| 5,533,661 A | 7/1996 | Main et al. |
| 5,535,937 A | 7/1996 | Boiarski et al. |
| 5,549,565 A | 8/1996 | Ryan et al. |
| 5,553,765 A | 9/1996 | Knodel et al. |
| 5,554,169 A | 9/1996 | Green et al. |
| RE35,352 E | 10/1996 | Peters |
| 5,562,677 A | 10/1996 | Hildwein et al. |
| 5,562,702 A | 10/1996 | Huitema et al. |
| 5,569,274 A | 10/1996 | Rapacki et al. |
| 5,571,116 A | 11/1996 | Bolanos et al. |
| 5,578,052 A | 11/1996 | Koros et al. |
| 5,580,067 A | 12/1996 | Hamblin et al. |
| 5,582,611 A | 12/1996 | Tsuruta et al. |
| 5,584,425 A | 12/1996 | Savage et al. |
| 5,584,848 A | 12/1996 | Yoon |
| 5,588,579 A | 12/1996 | Schnut et al. |
| 5,591,186 A | 1/1997 | Wurster et al. |
| 5,591,196 A | 1/1997 | Marin et al. |
| 5,597,107 A | 1/1997 | Knodel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,609,560 A | 3/1997 | Ichikawa et al. |
| 5,618,303 A | 4/1997 | Marlow et al. |
| 5,618,307 A | 4/1997 | Donlon et al. |
| 5,626,607 A | 5/1997 | Malecki et al. |
| 5,639,008 A | 6/1997 | Gallagher et al. |
| 5,651,780 A | 7/1997 | Jackson et al. |
| 5,653,374 A | 8/1997 | Young et al. |
| 5,653,692 A | 8/1997 | Masterson et al. |
| 5,662,680 A | 9/1997 | Desai |
| 5,665,100 A | 9/1997 | Yoon |
| 5,667,473 A | 9/1997 | Finn et al. |
| 5,667,478 A | 9/1997 | McFarlin et al. |
| 5,667,517 A | 9/1997 | Hooven |
| 5,667,526 A | 9/1997 | Levin |
| 5,669,918 A | 9/1997 | Balazs et al. |
| 5,676,674 A | 10/1997 | Bolanos et al. |
| 5,688,269 A | 11/1997 | Newton et al. |
| 5,692,668 A | 12/1997 | Schulze et al. |
| 5,693,031 A | 12/1997 | Ryan et al. |
| 5,709,335 A | 1/1998 | Heck |
| 5,711,472 A | 1/1998 | Bryan |
| 5,713,870 A | 2/1998 | Yoon |
| 5,732,871 A | 3/1998 | Clark et al. |
| 5,732,872 A | 3/1998 | Bolduc et al. |
| 5,735,289 A | 4/1998 | Pfeffer et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,885 A | 5/1998 | Sjostrom et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,458 A | 6/1998 | Wang et al. |
| 5,779,130 A | 7/1998 | Alesi et al. |
| 5,782,396 A | 7/1998 | Mastri et al. |
| 5,782,397 A | 7/1998 | Koukline |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,318 A | 9/1998 | St. Goar et al. |
| 5,807,377 A | 9/1998 | Madhani et al. |
| 5,807,402 A | 9/1998 | Yoon |
| 5,814,044 A | 9/1998 | Hooven |
| 5,815,640 A | 9/1998 | Wang et al. |
| 5,817,113 A | 10/1998 | Gifford, III et al. |
| 5,823,956 A | 10/1998 | Roth et al. |
| 5,829,662 A | 11/1998 | Allen et al. |
| 5,830,191 A | 11/1998 | Hildwein et al. |
| 5,836,503 A | 11/1998 | Ehrenfels et al. |
| 5,846,221 A | 12/1998 | Snoke et al. |
| 5,855,312 A | 1/1999 | Toledano |
| 5,855,583 A | 1/1999 | Wang et al. |

(56) References Cited

U.S. PATENT DOCUMENTS

| | | |
|---|---|---|
| 5,855,590 A | 1/1999 | Malecki et al. |
| 5,857,996 A | 1/1999 | Snoke |
| 5,860,581 A | 1/1999 | Robertson et al. |
| 5,860,953 A | 1/1999 | Snoke et al. |
| 5,863,366 A | 1/1999 | Snow |
| 5,868,760 A | 2/1999 | McGuckin, Jr. |
| 5,868,779 A | 2/1999 | Ruiz |
| 5,871,471 A | 2/1999 | Ryan et al. |
| 5,878,193 A | 3/1999 | Wang et al. |
| 5,881,943 A | 3/1999 | Heck et al. |
| 5,893,875 A | 4/1999 | O'Connor et al. |
| 5,897,562 A | 4/1999 | Bolanos et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,928,261 A | 7/1999 | Ruiz |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |
| 5,993,378 A | 11/1999 | Lemelson |
| 5,993,454 A | 11/1999 | Longo |
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,054 A | 1/2000 | Johnson et al. |
| 6,010,493 A | 1/2000 | Snoke |
| 6,017,322 A | 1/2000 | Snoke et al. |
| 6,017,354 A | 1/2000 | Culp et al. |
| 6,024,741 A | 2/2000 | Williamson, IV et al. |
| 6,050,472 A | 4/2000 | Shibata |
| 6,063,095 A | 5/2000 | Wang et al. |
| 6,068,627 A | 5/2000 | Orszulak et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |
| 6,159,196 A | 12/2000 | Ruiz |
| 6,162,220 A | 12/2000 | Nezhat |
| 6,162,236 A | 12/2000 | Osada |
| 6,165,191 A | 12/2000 | Shibata et al. |
| 6,171,282 B1 | 1/2001 | Ragsdale |
| 6,174,324 B1 | 1/2001 | Egan et al. |
| 6,179,837 B1 | 1/2001 | Hooven |
| 6,193,129 B1 | 2/2001 | Bittner et al. |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| 6,209,773 B1 | 4/2001 | Bolduc et al. |
| 6,217,591 B1 | 4/2001 | Egan et al. |
| D441,862 S | 5/2001 | Cooper et al. |
| 6,231,587 B1 | 5/2001 | Makower |
| 6,237,605 B1 | 5/2001 | Vaska et al. |
| 6,244,809 B1 | 6/2001 | Wang et al. |
| 6,246,200 B1 | 6/2001 | Blumenkranz et al. |
| 6,251,093 B1 | 6/2001 | Valley et al. |
| D444,555 S | 7/2001 | Cooper et al. |
| 6,261,273 B1 | 7/2001 | Ruiz |
| 6,264,087 B1 | 7/2001 | Whitman |
| 6,280,415 B1 | 8/2001 | Johnson |
| 6,309,397 B1 | 10/2001 | Julian et al. |
| 6,312,435 B1 | 11/2001 | Wallace et al. |
| 6,315,184 B1 | 11/2001 | Whitman |
| 6,331,181 B1 | 12/2001 | Tierney et al. |
| 6,346,072 B1 | 2/2002 | Cooper |
| 6,348,061 B1 | 2/2002 | Whitman |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,443,973 B1 | 9/2002 | Whitman |
| 6,482,224 B1 | 11/2002 | Michler et al. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 6,632,227 B2 | 10/2003 | Adams |
| 6,679,904 B2 | 1/2004 | Gleeson et al. |
| 6,685,712 B2 | 2/2004 | Cummins et al. |
| 8,025,199 B2 | 9/2011 | Whitman et al. |
| 2001/0001812 A1 | 5/2001 | Valley et al. |
| 2001/0010247 A1 | 8/2001 | Snow |
| 2001/0016725 A1 | 8/2001 | Valley et al. |
| 2001/0016750 A1 | 8/2001 | Malecki et al. |
| 2001/0023334 A1 | 9/2001 | St. Goar et al. |
| 2001/0031975 A1* | 10/2001 | Whitman ............ A61B 10/0233 606/167 |
| 2001/0044591 A1 | 11/2001 | Stevens et al. |
| 2002/0013569 A1 | 1/2002 | Sterman et al. |
| 2002/0026094 A1 | 2/2002 | Roth |
| 2002/0029783 A1 | 3/2002 | Stevens et al. |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0049454 A1 | 4/2002 | Whitman et al. |
| 2002/0055795 A1 | 5/2002 | Niemeyer et al. |
| 2002/0068922 A1 | 6/2002 | Peters |
| 2002/0072736 A1 | 6/2002 | Tierney et al. |
| 2002/0072741 A1 | 6/2002 | Sliwa et al. |
| 2002/0087157 A1 | 7/2002 | Sliwa et al. |
| 2002/0104400 A1 | 8/2002 | Hillgaertner et al. |
| 2002/0165444 A1 | 11/2002 | Whitman |
| 2003/0105478 A1 | 6/2003 | Whitman et al. |
| 2003/0130677 A1 | 7/2003 | Whitman et al. |
| 2005/0051597 A1 | 3/2005 | Toledano |
| 2005/0187576 A1 | 8/2005 | Whitman et al. |

FOREIGN PATENT DOCUMENTS

| | | |
|---|---|---|
| DE | 4312147 A1 | 10/1993 |
| EP | 0041022 A1 | 12/1981 |
| EP | 0093101 A2 | 11/1983 |
| EP | 0116220 A1 | 8/1984 |
| EP | 0121474 A2 | 10/1984 |
| EP | 0142225 A1 | 5/1985 |
| EP | 0156774 A2 | 10/1985 |
| EP | 0203375 A2 | 12/1986 |
| EP | 0216532 A1 | 4/1987 |
| EP | 0293123 A2 | 11/1988 |
| EP | 0324166 A2 | 7/1989 |
| EP | 0324637 A1 | 7/1989 |
| EP | 0365153 A1 | 4/1990 |
| EP | 0369324 A1 | 5/1990 |
| EP | 0373762 A1 | 6/1990 |
| EP | 0399701 A1 | 11/1990 |
| EP | 0484677 A1 | 5/1992 |
| EP | 0514139 A2 | 11/1992 |
| EP | 0536903 A2 | 4/1993 |
| EP | 0539762 A1 | 5/1993 |
| EP | 0552050 A2 | 7/1993 |
| EP | 0552423 A2 | 7/1993 |
| EP | 0581400 A1 | 2/1994 |
| EP | 0593920 A1 | 4/1994 |
| EP | 0598579 A1 | 5/1994 |

(56) References Cited

FOREIGN PATENT DOCUMENTS

| | | |
|---|---|---|
| EP | 0621006 A1 | 10/1994 |
| EP | 0630612 A1 | 12/1994 |
| EP | 0634144 A1 | 1/1995 |
| EP | 0639349 A2 | 2/1995 |
| EP | 0653922 A1 | 5/1995 |
| EP | 0679367 A2 | 11/1995 |
| EP | 0705571 A1 | 4/1996 |
| EP | 0878169 A1 | 11/1998 |
| EP | 0947167 A1 | 10/1999 |
| FR | 2660851 A1 | 10/1991 |
| GB | 1352554 A | 5/1974 |
| GB | 1452185 A | 10/1976 |
| GB | 2022421 A | 12/1979 |
| GB | 2031733 A | 4/1980 |
| GB | 2048685 A | 12/1980 |
| GB | 2165559 A | 4/1986 |
| SU | 659146 A1 | 4/1979 |

* cited by examiner

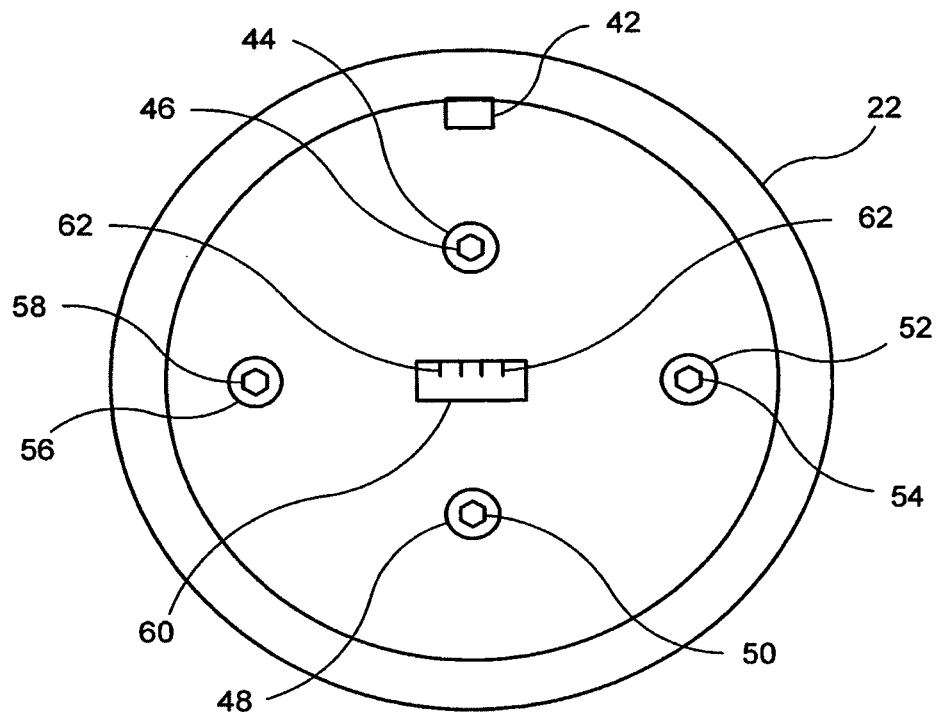
F I G. 5(a)
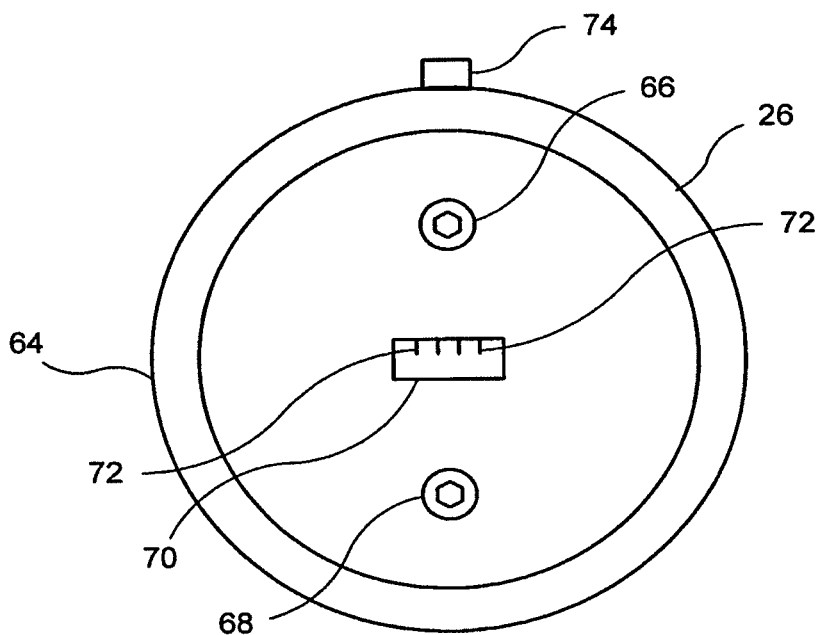
F I G. 5(b)

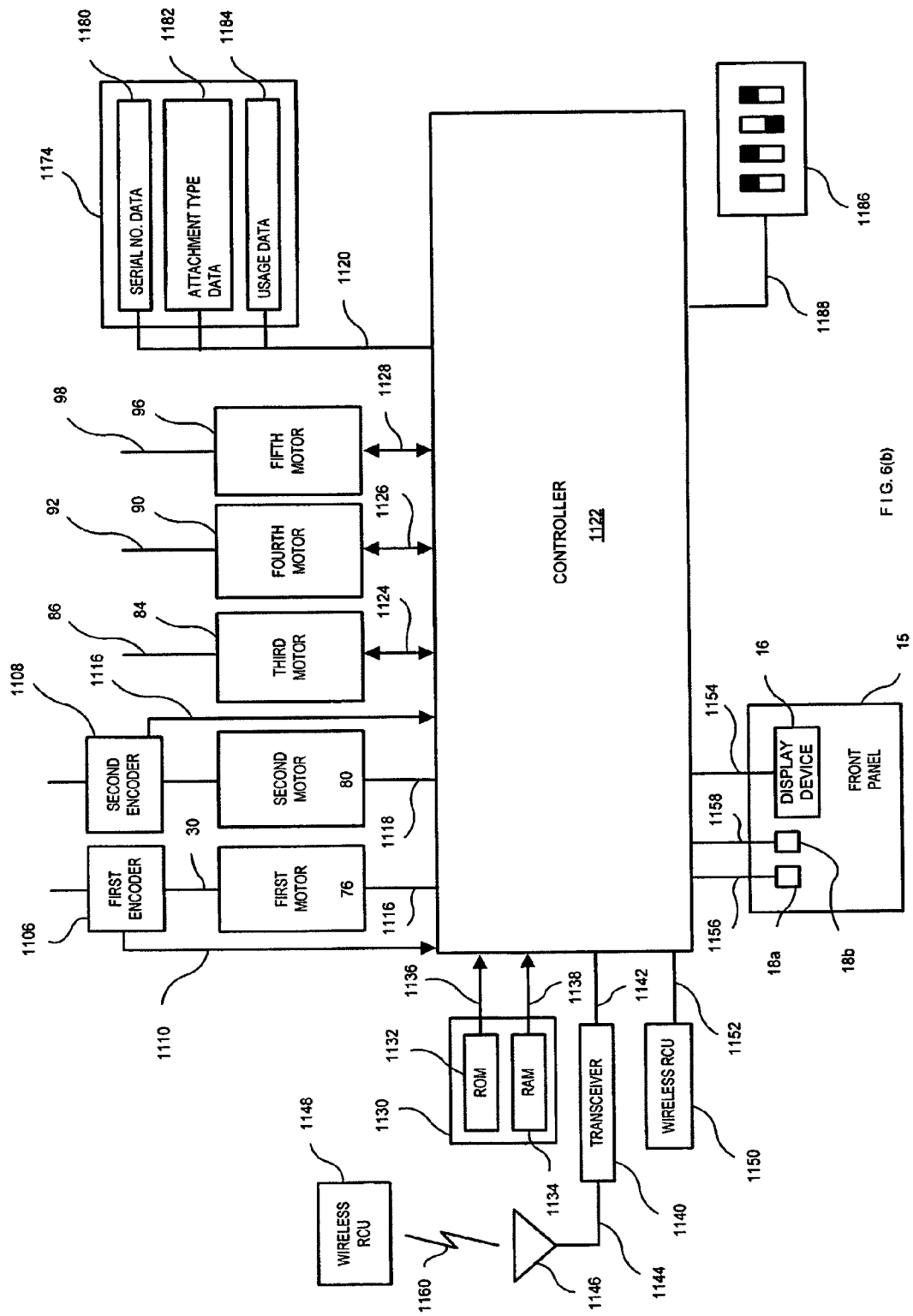

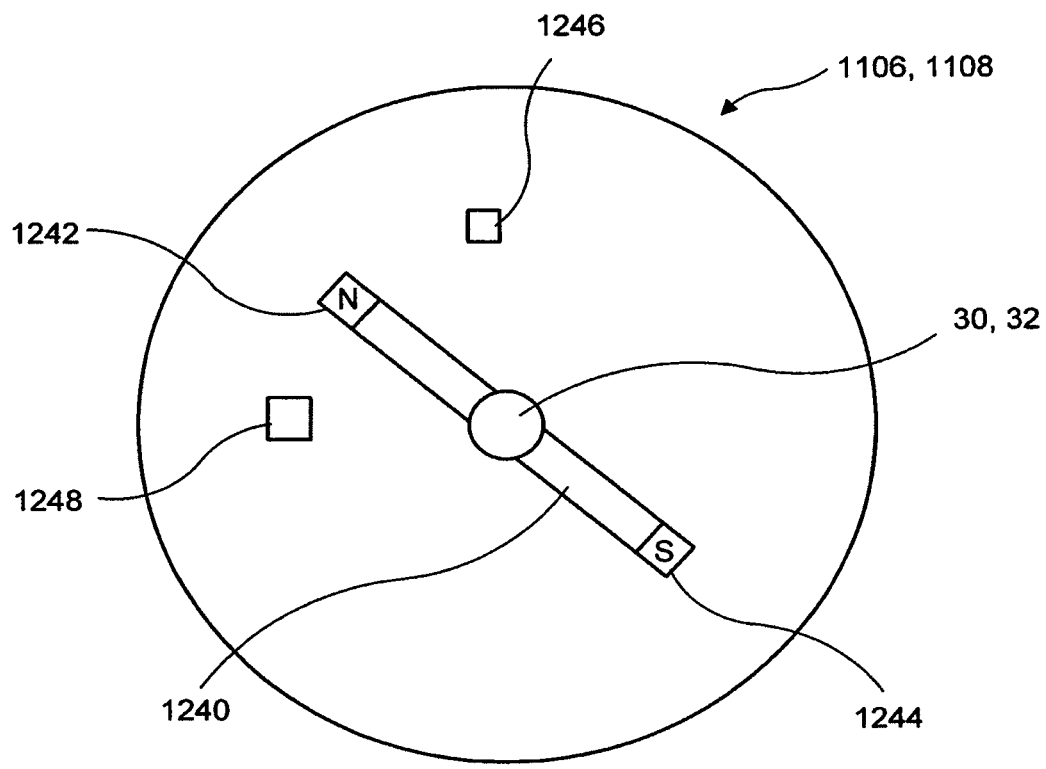
F I G. 6(c)
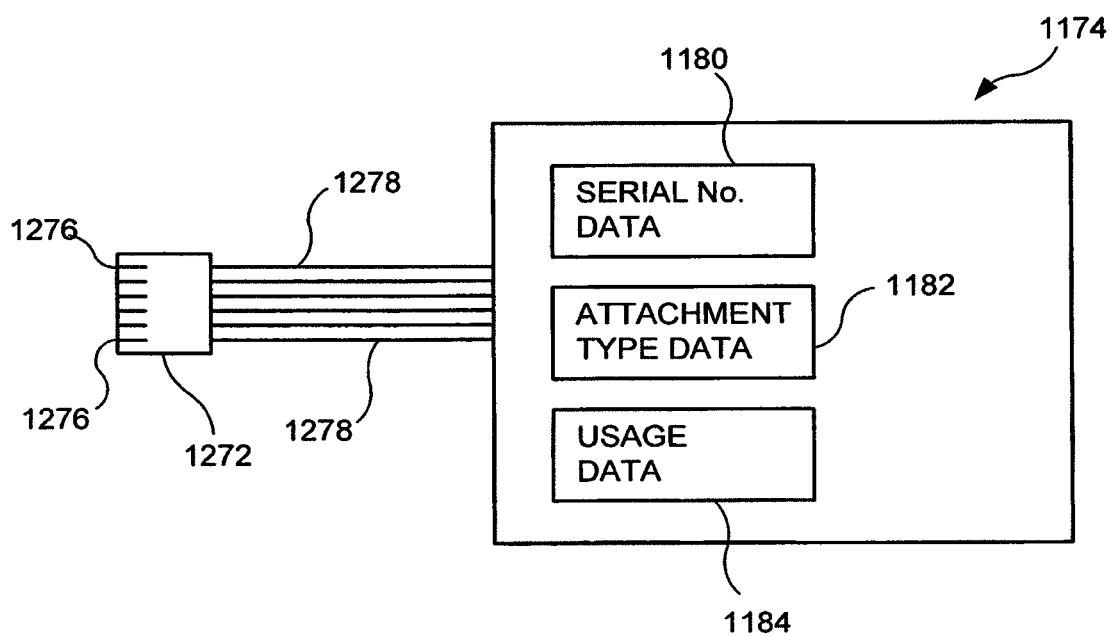
F I G. 6(d)

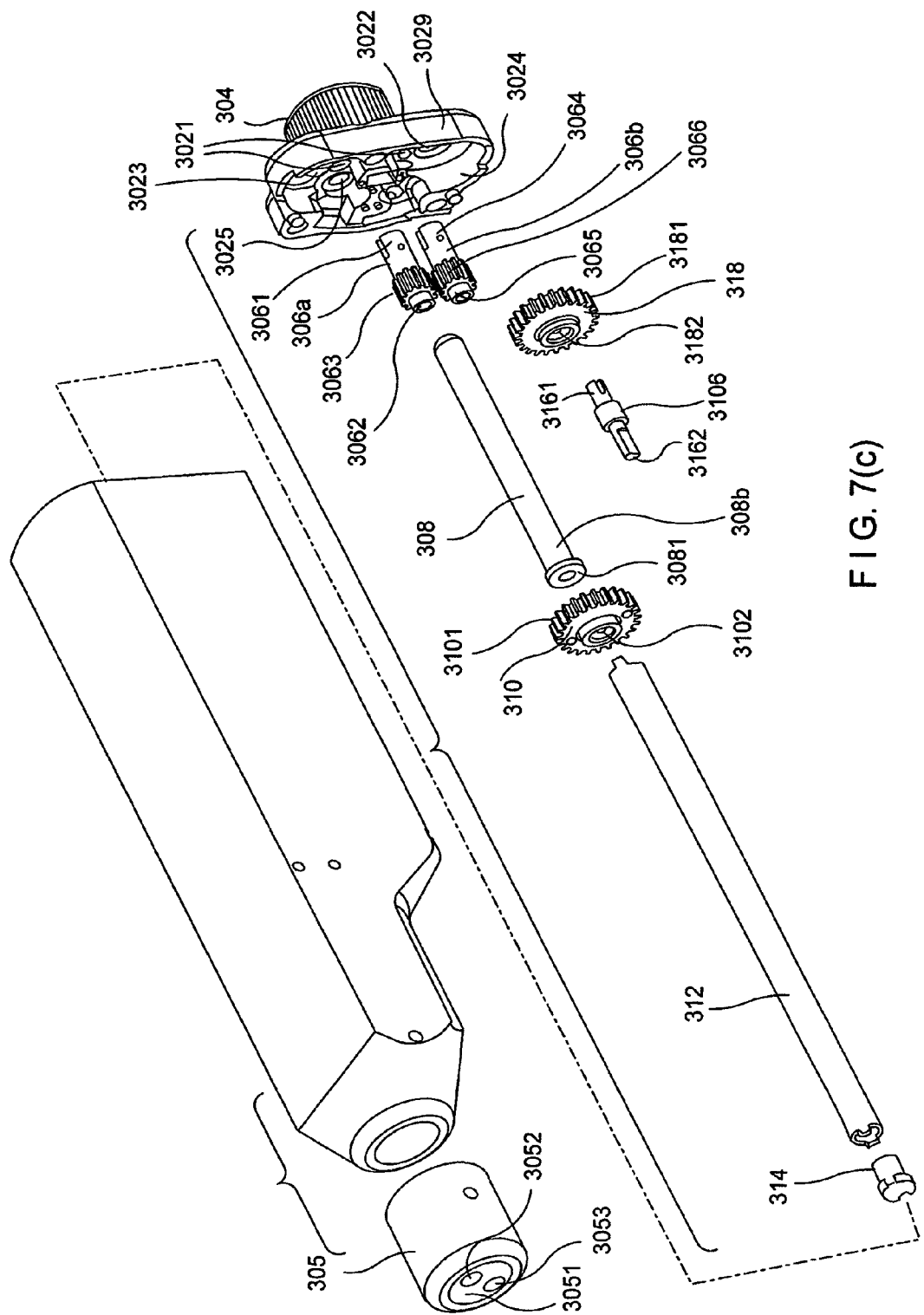
F I G. 7(c)

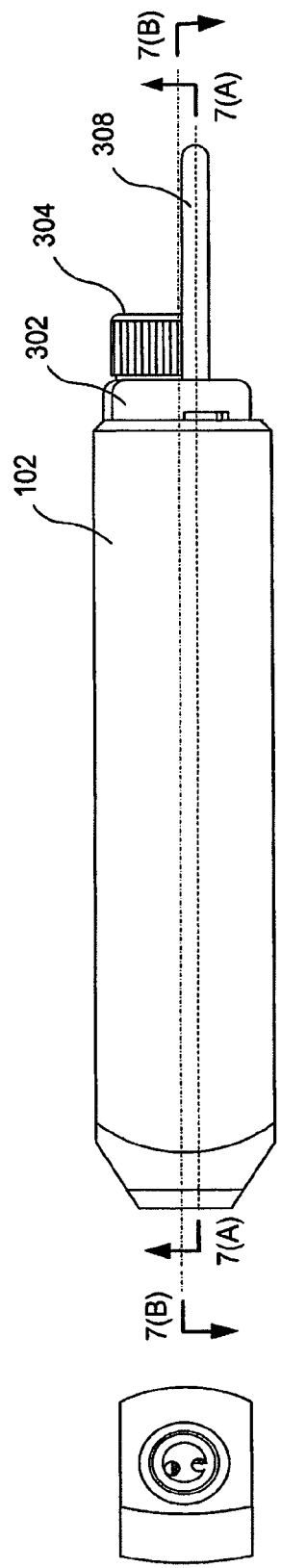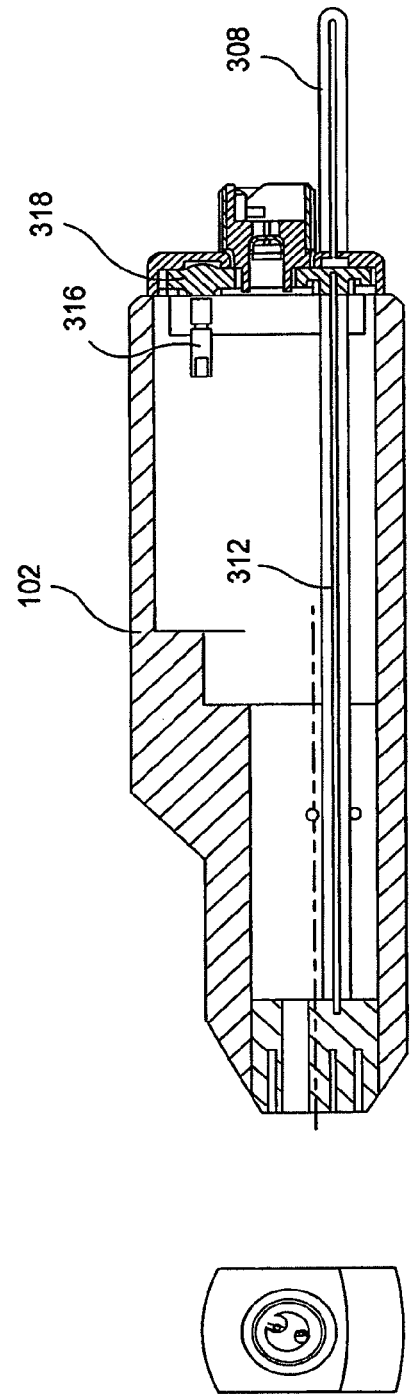
FIG. 7(d)
FIG. 7(e)

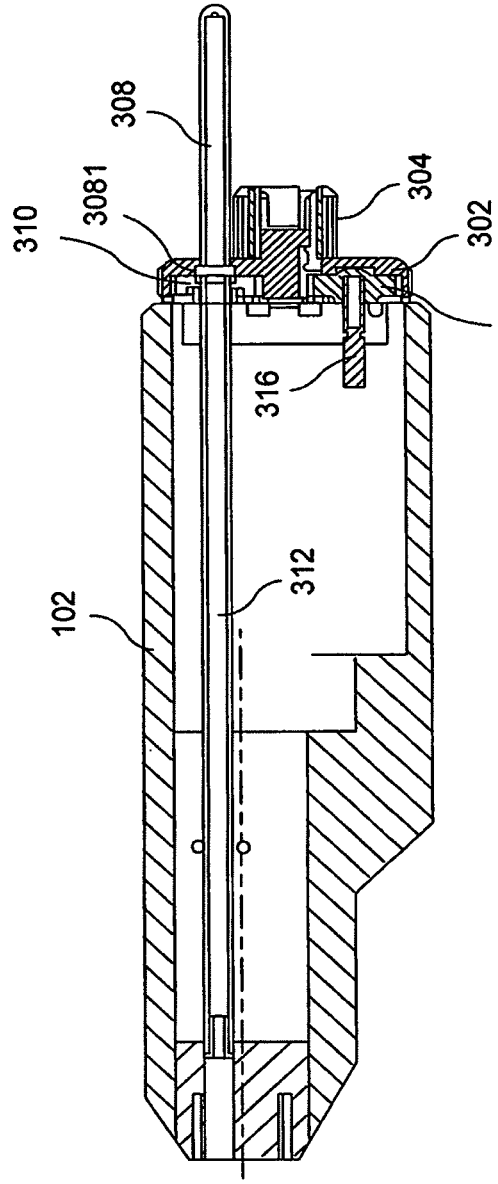
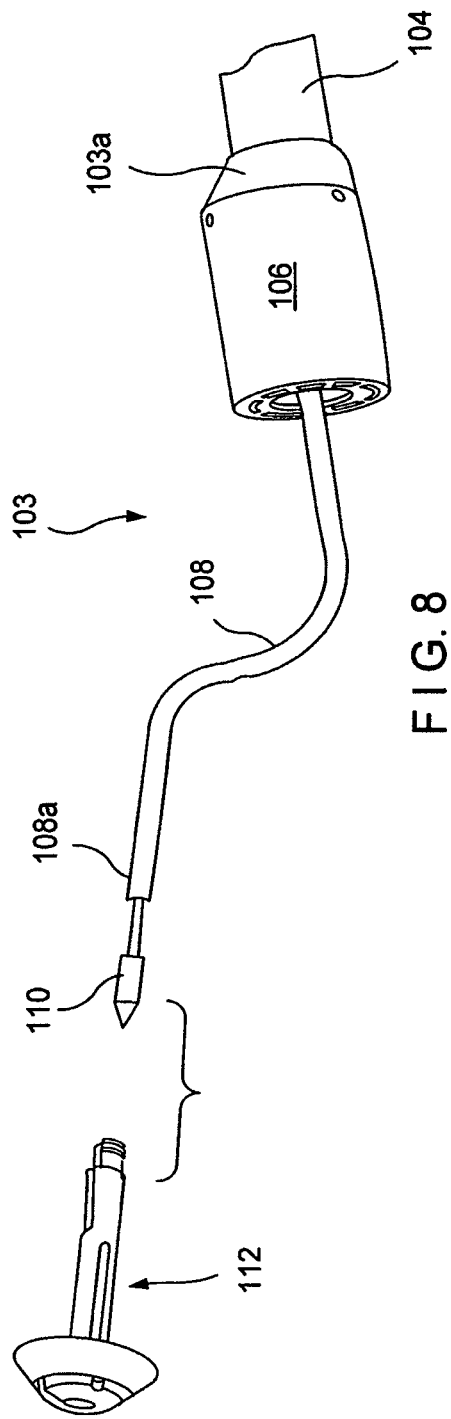
FIG. 7(f)
FIG. 8

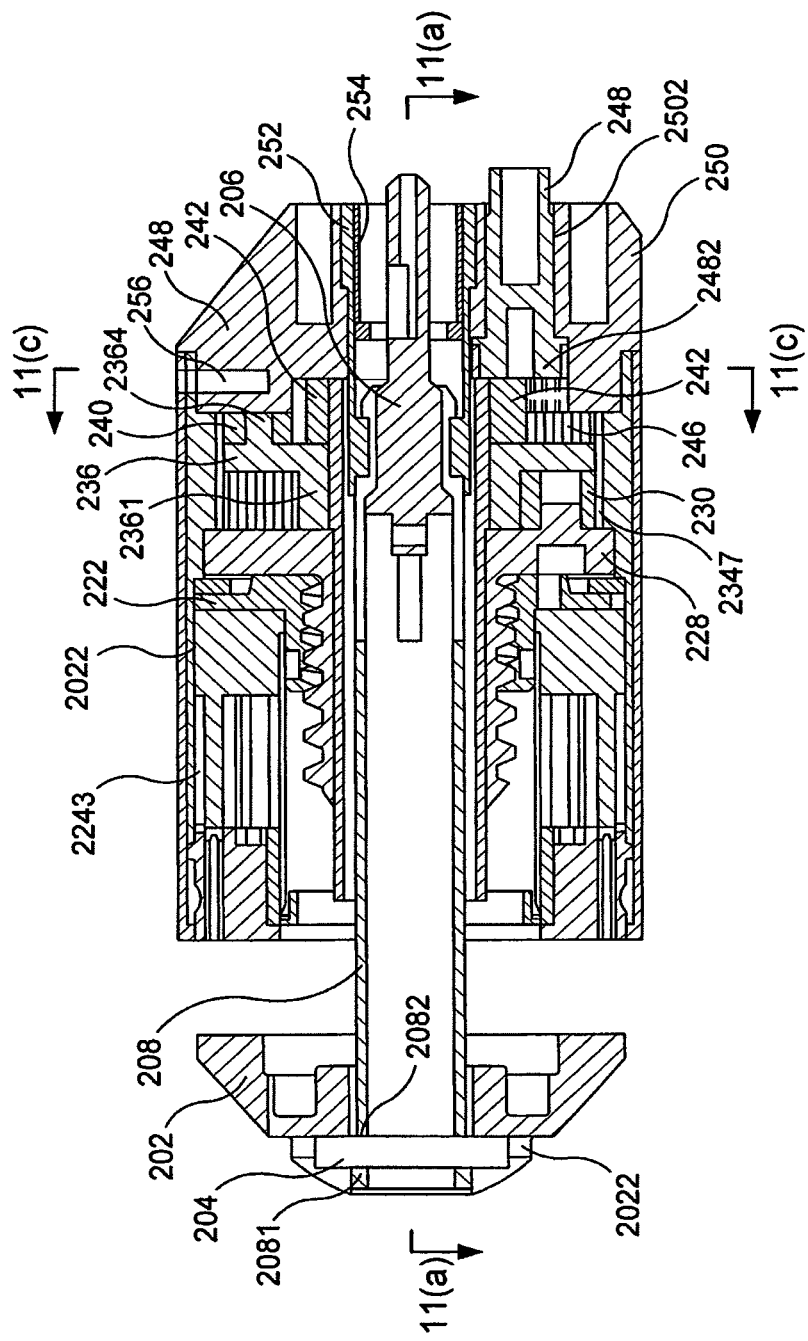
F I G. 11(b)

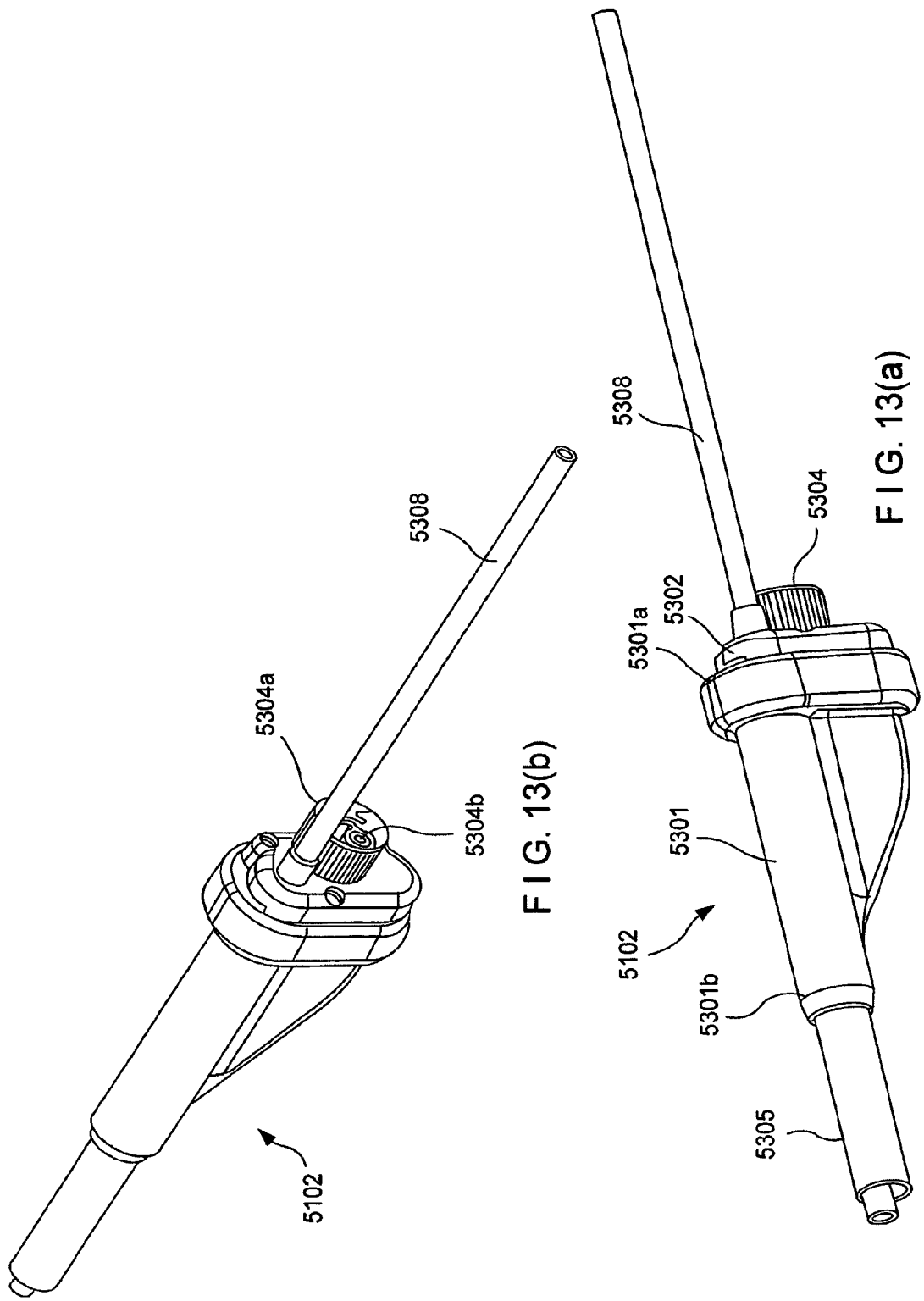

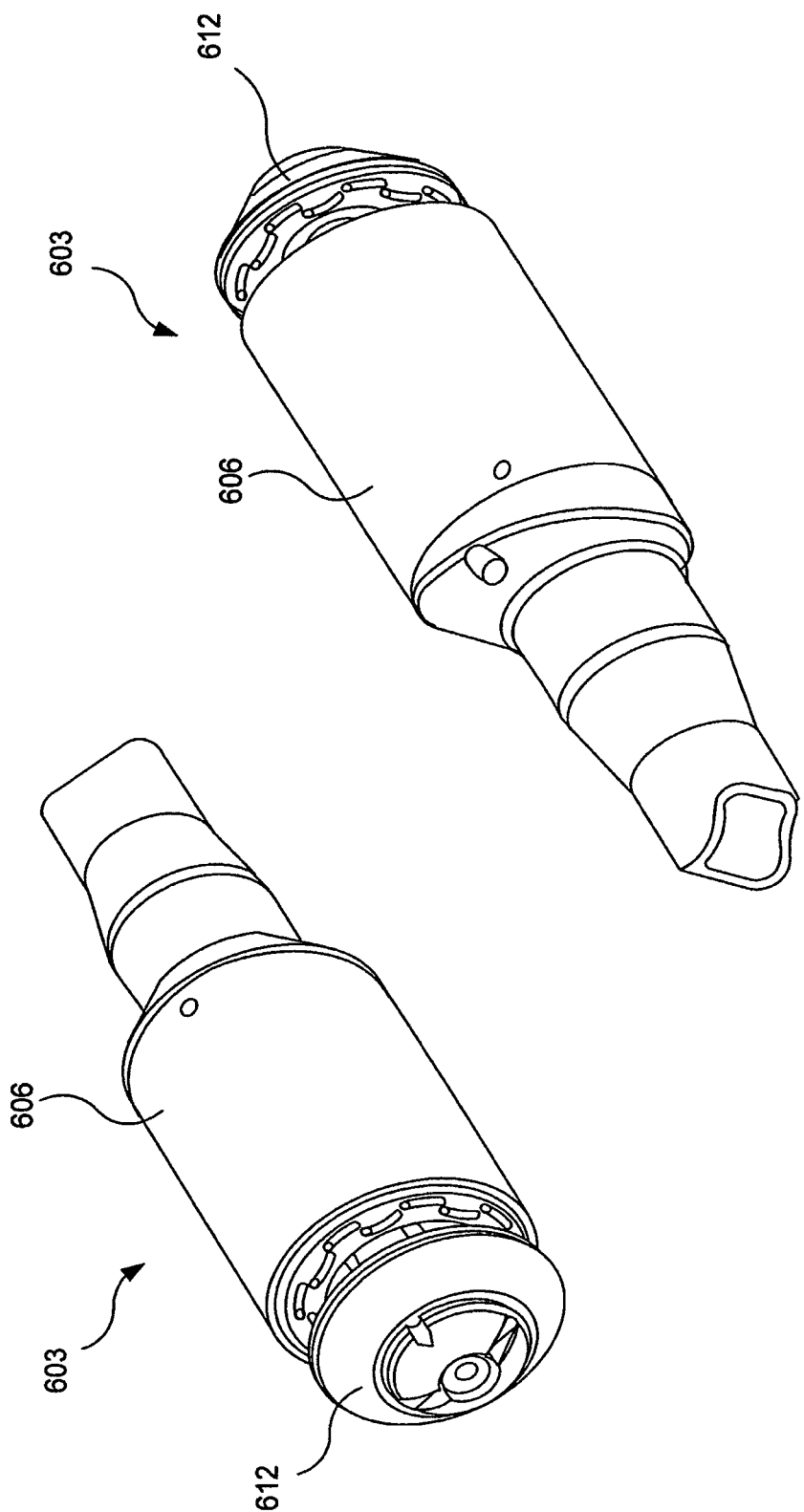

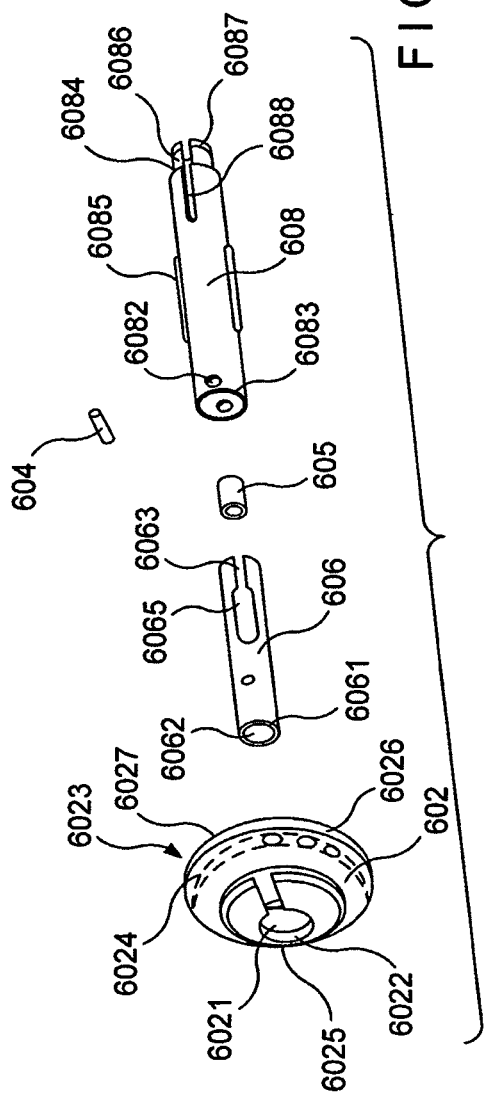
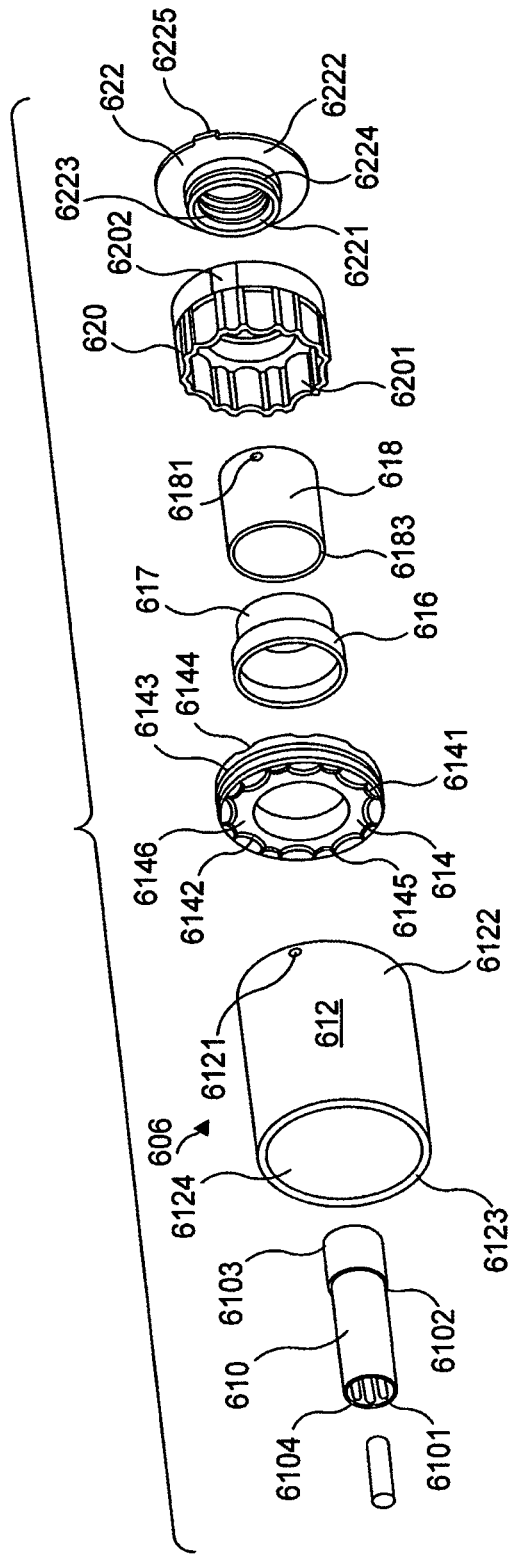
FIG. 15(a)
FIG. 15(b)

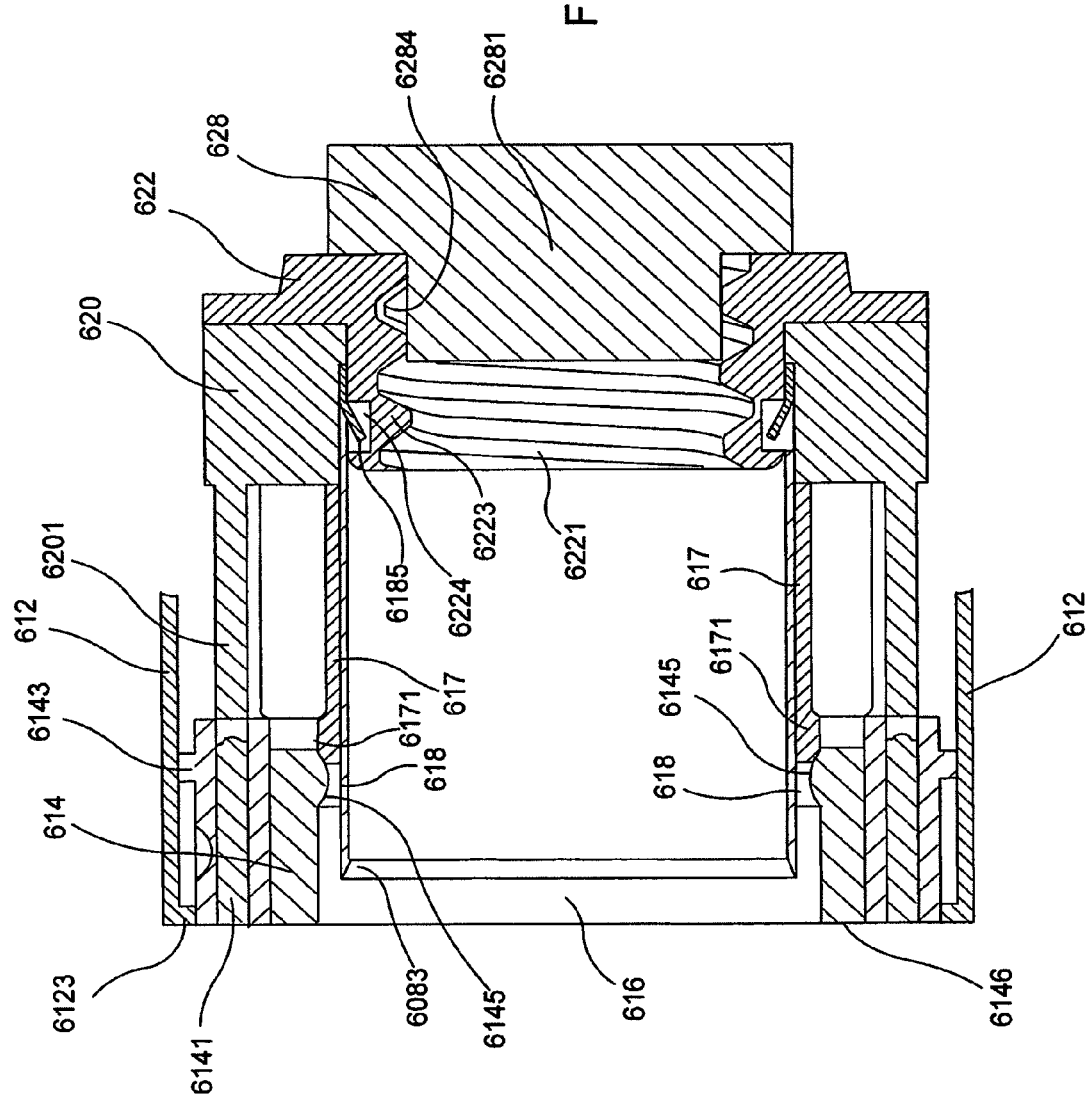

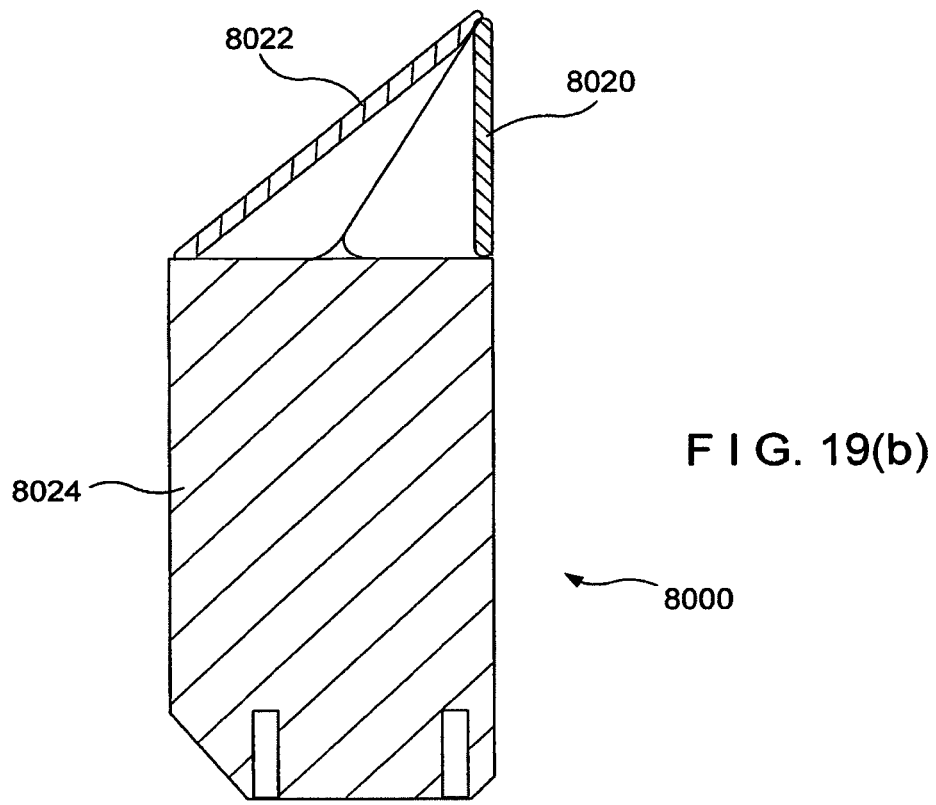
F I G. 19(b)
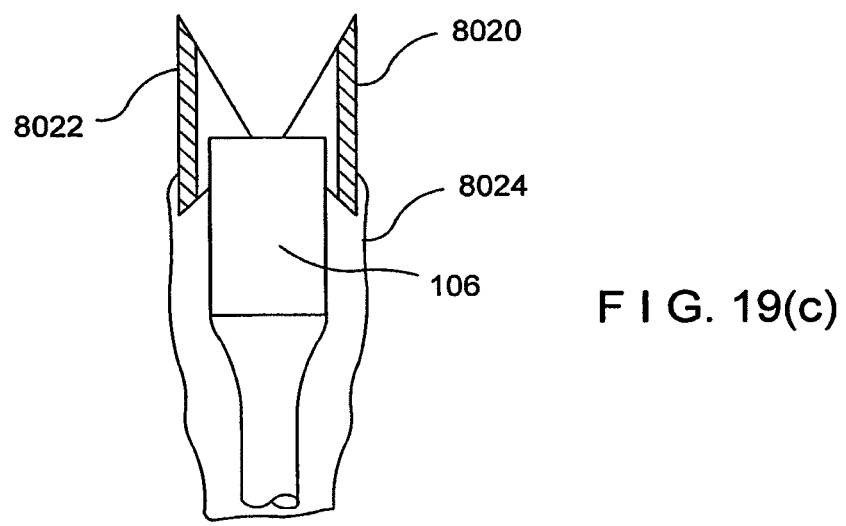
F I G. 19(c)

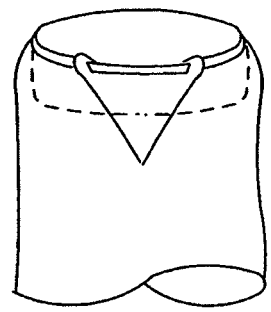
F I G. 19(d)
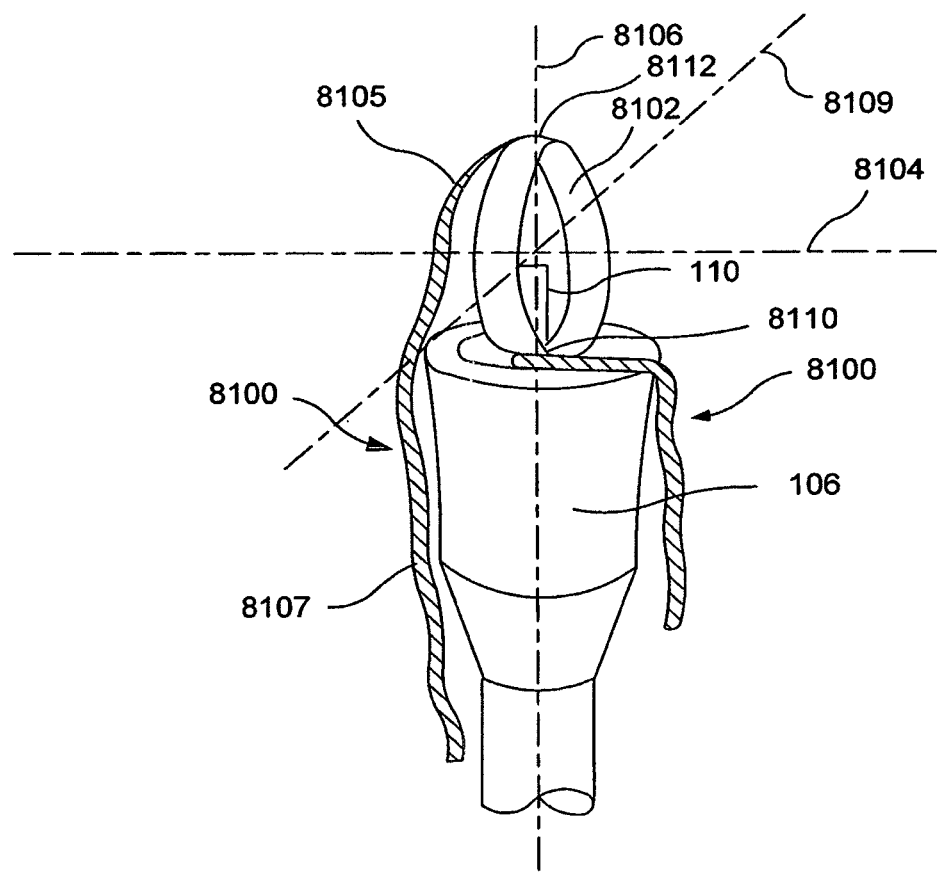
F I G. 19(e)

SURGICAL CUTTING AND STAPLING DEVICE

CROSS-REFERENCE TO RELATED APPLICATIONS

The present application is a Divisional application claiming the benefit of and priority to U.S. patent application Ser. No. 13/207,585, filed on Aug. 11, 2011, which is a Divisional application claiming the benefit of and priority to U.S. patent application Ser. No. 10/785,672, filed Feb. 23, 2004 (now U.S. Pat. No. 8,025,199), the entire content of each of which is incorporated herein by reference.

The present application relates to U.S. patent application Ser. No. 09/324,452, filed on Jun. 2, 1999 and issued as U.S. Pat. No. 6,443,973; U.S. application Ser. No. 09/723,715, filed Nov. 28, 2000 and issued as U.S. Pat. No. 6,793,652; U.S. application Ser. No. 09/324,451, filed on Jun. 2, 1999 and issued as U.S. Pat. No. 6,315,184; U.S. application Ser. No. 09/351,534, filed on Jul. 12, 1999 and issued as U.S. Pat. No. 6,264,087; U.S. application Ser. No. 09/510,923, filed on Feb. 22, 2000 and issued as U.S. Pat. No. 6,517,565; U.S. application Ser. No. 09/510,927, filed on Feb. 22, 2000 and issued as U.S. Pat. No. 6,793,652; U.S. application Ser. No. 09/510,932, filed on Feb. 22, 2000 and issued as U.S. Pat. No. 6,491,201; U.S. application Ser. No. 09/887,789, filed on Jul. 22, 2001 and issued as U.S. Pat. No. 7,032,798, each of which is expressly incorporated herein in its entirety by reference.

FIELD OF THE INVENTION

The present invention relates to an electromechanical surgical system, and more particularly to a surgical attachment of an electromechanical surgical system for clamping, cutting and stapling tissue in the body of a patient.

BACKGROUND INFORMATION

There are many surgical procedures that require a surgical instrument to be introduced into an orifice of a body. One example of such is a surgical procedure to resect a cancerous or anomalous tissue from an oral passage by the introduction, e.g., insertion, of a circular clamping, cutting and stapling instrument via a patient's oral cavity.

One of the problems experienced during surgical procedures of this type is that the orifice of the body may be damaged when the surgical instrument is being introduced, or has been introduced, into the orifice. This is particularly problematic when the orifice into which the surgical device is being introduced includes fragile tissue that is easily damaged when contacted, e.g., the tissues of the oral cavity. Another problem experienced during surgical procedures of this type is that the surgical instrument may be damaged when the surgical instrument is being introduced, or has been introduced, into the orifice. It may be particularly important to avoid damage to the surgical device, since a patient may also be harmed if the surgical device functions improperly.

While significant advances have been made in miniaturizing surgical instruments, conventional surgical instruments are typically not able to be employed within a relatively small orifice or passage of a patient, such an oral passage. Thus, conventional surgical devices and procedures still risk damage to one or both of the surgical device and the orifice/passage.

Thus, there is a need for a device that minimizes the likelihood of damage to one or both of a surgical device and an orifice or passage of a patient, e.g., an oral passage, when the surgical device is introduced into the orifice.

SUMMARY OF THE INVENTION

The present invention, in accordance with various embodiments thereof, relates to a surgical device for at least one of cutting and stapling a section of tissue. The surgical device includes a housing including at least two drivers. The surgical device also includes an anvil mechanically attachable to the housing and moveable relative to the housing between an open position and a closed position. The first driver operates to move the anvil relative to the housing to an intermediate position between the open position and the closed position. The second driver operates to move at least a portion of the housing relative to the anvil between the intermediate position and the closed position.

Advantageously, the anvil and the housing define first and second clamping faces, respectively. When the anvil is in the closed position, the surgical device is configured to clamp a section of tissue between the first clamping face of the anvil and the second clamping face of the housing. The housing may include a cutting element configured to be driven between a retracted position and an extended position by the second driver. The housing may also include a stapling element configured to be driven between a retracted position and an extended position by the second driver. The stapling element includes a staple cartridge that is configured to move axially within the housing between a retracted position and an extended position by the second driver, and a staple pusher configured to push staples that are stored within respective staple slots of the staple cartridge out of the staple slots and into staple guides in the anvil.

The present invention, in accordance with various embodiments thereof, also relates to a surgical device for stapling a section of tissue. The surgical device includes a staple pusher and a housing configured to store staples. The housing is selectively moveable relative to the staple pusher. The surgical device also includes an anvil moveable relative to the staple pusher and the housing. Movement of the anvil causes the housing to move relative to the staple pusher. The anvil may be moveable relative to the staple pusher between a first position, in which the anvil is spaced apart from a clamping surface of the housing, and a second position, in which the anvil contacts the clamping surface of the housing. Furthermore, the anvil may be moveable relative to the staple pusher between the second position and a third position, in which the staples stored in the housing are pushed out of the housing by the staple pusher to be closed against the anvil. In one embodiment, the housing is connected to the staple pusher by a shear pin, wherein the shear pin is configured to shear when, by the movement of the anvil between the second and the third position, the anvil applies a predetermined amount of pressure on the clamping surface of the housing.

The present invention, in accordance with various embodiments thereof, also relates to a surgical device for cutting a section of tissue. The surgical device includes a cutting element and a housing having a clamping surface. The housing is selectively moveable relative to the cutting element. The surgical device also includes an anvil moveable relative to the cutting element and the housing. Movement of the anvil causes the housing to move relative to the cutting element. The anvil may be moveable relative to the cutting element between a first position, in which the anvil is spaced apart from a clamping surface of the housing, and a second position, in which the anvil contacts the clamping surface of the housing. Furthermore, the anvil may be moveable relative to the cutting element between the second position and a third position, in which the cutting element is brought into contact with the anvil. In one embodiment, the housing is connected to the cutting element by a shear pin, which is configured to shear when, by the movement of the anvil between the second and the third position, the anvil applies a predetermined amount of pressure on the clamping surface of the housing.

The present invention, in accordance with various embodiments thereof, also relates to a surgical device for at least one of cutting and stapling a section of tissue. The surgical device includes a housing forming a first clamping surface. The surgical device also includes an anvil mechanically attachable and moveable relative to the housing along an axis between an extended position and a retracted position. The anvil forms a second clamping surface. At least a portion of the first and second clamping surfaces are non-perpendicular relative to the axis. Preferably, when the anvil is in the closed position, the surgical device is configured to clamp a section of tissue between the first and second clamping faces. Furthermore, the first and second clamping faces may be parallel relative to each other. A first driver may be employed to move the anvil relative to the housing. A second driver may also be employed, wherein the housing includes a cutting element configured to be driven between a retracted position and an extended position by the second driver. In addition, the housing may include a stapling element configured to be driven between a retracted position and an extended position by the second driver.

The present invention, in accordance with various embodiments thereof, also relates to a surgical device for at least one of cutting and stapling a section of tissue. The surgical device also includes a housing including a stapling element. The stapling element includes a staple cartridge defining a plurality of slots and staples stored within the slots. The stapling element also includes a staple pusher having staple pusher fingers aligned with the plurality of slots. The surgical device also includes a driver configured to move the staple cartridge and the staple pusher together between a retracted position and an intermediate position. At the intermediate position, the driver moves the staple pusher relative to the staple cartridge to an extended position. The surgical device may also include an interference element that is configured to maintain the relative position of the staple cartridge and the staple pusher when the driver moves the staple cartridge and the staple pusher together between the retracted position and the intermediate position. The intermediate position may be a position at which the staple cartridge sufficiently clamps a section of tissue or a position at which the staple cartridge is axially locked in position relative to the housing. The interference element may be a frangible component. Alternatively, the interference element may be connected to the staple pusher and may include a radially extending rib that maintains contact with a portion of the staple cartridge up to a predetermined pressure. The surgical device may also include a cutting element, e.g., a blade, wherein the radially extending rib of the interference element contacts an oppositely-disposed, radially extending rib of the staple cartridge and the blade.

The present invention, in accordance with various embodiments thereof, also relates to a surgical device for at least one of cutting and stapling a section of tissue. The surgical device may include a housing. The surgical device may also include a staple cartridge positioned at a distal end of the housing and defining a plurality of slots and staples stored within the slots. The surgical device may also include a staple pusher positioned proximal to the staple cartridge and having a plurality of staple pusher fingers aligned with the plurality of slots. The surgical device may also include a pusher element positioned proximal to the staple pusher and configured to be simultaneously rotated within the housing and distally advanced relative to the staple cartridge. The pusher element has a cam element extending toward the staple pusher such that the cam element sequentially pushes against the plurality of staple pusher fingers. The pusher element may be keyed to a rotatable member that extends longitudinally towards the staple cartridge, such as a neck portion of a spider screw element. The surgical device may also include a nut positioned proximally relative to the pusher element, the nut having an internally threaded bore, wherein the internally threaded bore of the nut is in threaded engagement with the rotatable member.

The present invention, in accordance with various embodiments thereof, also relates to a sleeve for facilitating the insertion of a surgical device into one of an orifice and a passage of a patient, the surgical device having a distal end defining a cross-section. The surgical device may include a first portion configured to cover at least a portion of the surgical device. The surgical device may also include at least one closure element selectively moveable between an insertion position, in which the closure element(s) tapers to a cross-section that is smaller than the cross-section of the distal end of the surgical device, and a retracted position, in which the surgical device is configured to perform, through the closure elements, a surgical operation in one of the orifice and the passage of the patient.

BRIEF DESCRIPTION OF THE DRAWINGS

FIG. 5(a) is a rear end view of a first coupling of the flexible shaft illustrated in FIG. 3.

FIG. 5(b) is a front end view of a second coupling of the flexible shaft illustrated in FIG. 3.

FIG. 6(b) is a schematic view of the electromechanical surgical system illustrated in FIG. 1.

FIG. 6(c) is a schematic view of an encoder of the flexible shaft illustrated in FIGS. 3 and 4.

FIG. 6(d) is a schematic view of a memory device, according to one embodiment of the present invention.

FIG. 7(c) is an exploded front perspective view of the handle portion shown in FIG. 7(a).

FIG. 7(d) is a top view of the handle portion illustrated in FIG. 7(a).

FIG. 7(e) is a side cross-sectional view of the handle portion illustrated in FIG. 7(d) taken along the lines A-A.

FIG. 7(f) is a side cross-sectional view of the handle portion illustrated in FIG. 7(d) taken along the lines B-B.

FIG. 8 is a perspective view of a cutting and stapling component in an extended position, according to one embodiment of the present invention.

FIG. 11(b) is a side, cross-sectional view that illustrate the cutting and stapling component, according to one embodiment of the present invention.

FIGS. 13(a) to 13(c) illustrate a handle portion, according to another embodiment of the present invention.

FIG. 14(a) is a front perspective view that illustrates a cutting and stapling component in an assembled and partially closed position, according to another embodiment of the present invention.

FIG. 14(b) is a rear perspective view that illustrates the cutting and stapling component shown in FIG. 14(a), in an assembled and partially closed position.

FIG. 15(a) is a front exploded view that illustrates the components of an anvil assembly, according to another embodiment of the present invention.

FIG. 15(b) is an exploded, perspective view that illustrates some of the components of the staple and blade portion shown in FIG. 15(a).

FIG. 15(d) is an assembled, side cross-sectional view that illustrates some of the components of the staple and blade portion shown in FIG. 15(a).

FIG. 19(b) is a side cross-sectional view of a portion of the sleeve shown in FIG. 19(a) in a closed position.

FIG. 19(c) illustrates the closure elements of the sleeve shown in FIG. 19(a) in the open position.

FIG. 19(d) is a perspective view of a sleeve that is configured to cover a surgical device in an insertion position, according to another embodiment of the present invention.

FIG. 19(e) is a perspective view of the sleeve shown in FIG. 19(d) in a retracted position.

DETAILED DESCRIPTION

Figure 1:
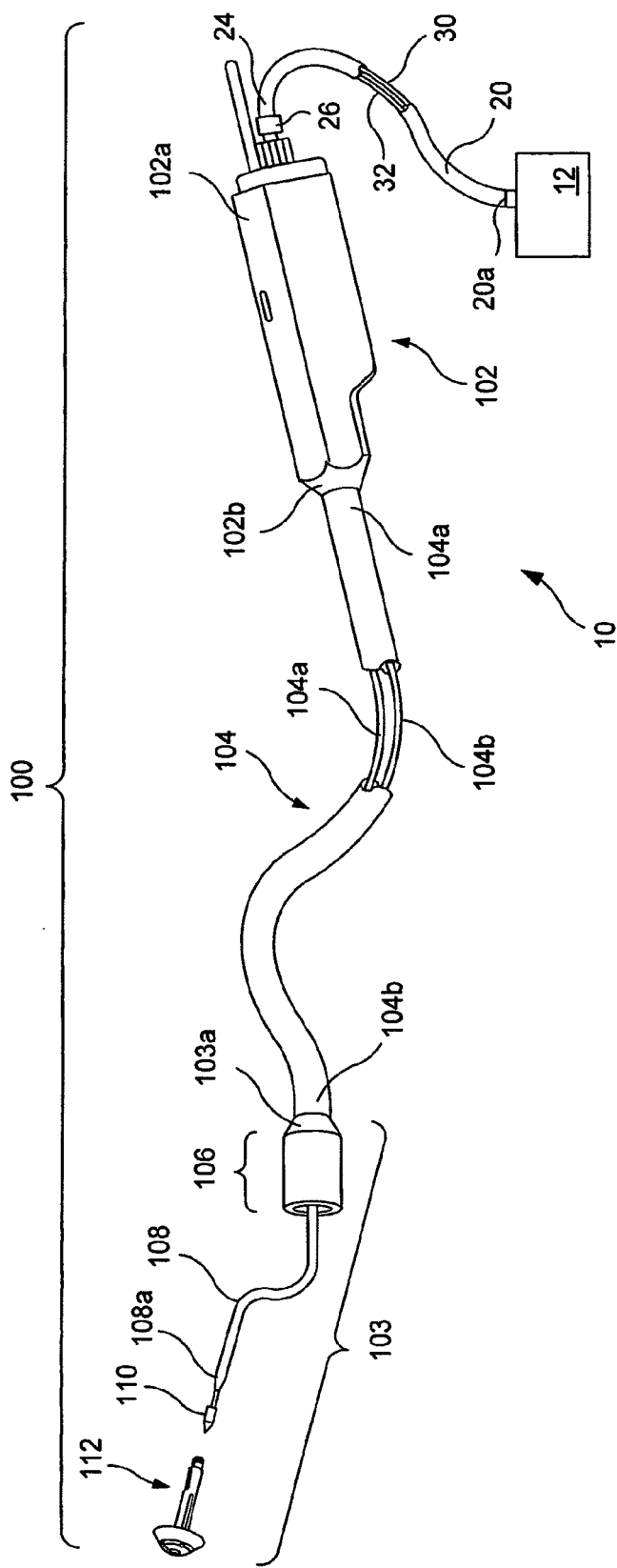
FIG. 1 is a perspective view of an electro-mechanical surgical system, according to one embodiment of the present invention.

The present invention is directed to an electro-mechanical surgical system. FIG. 1 is a perspective view of an electro-mechanical surgical system 10 according to one embodiment of the present invention.

As shown in FIG. 1, the electro-mechanical surgical system 10 includes a remote power console 12 having a flexible shaft 20 extending therefrom. The flexible shaft 20 includes at least a first rotatable drive shaft 30 and a second rotatable drive shaft 32. Additional details of the remote power console 12 are described and shown in connection with, e.g., FIG. 2. Additional details of the flexible shaft 20 are described and shown in connection with, e.g., FIGS. 3 to 6.

Attached, or attachable, to a coupling 26 at the distal end 24 of the flexible cable 20 is a surgical attachment 100. The surgical attachment 100 is configured to perform a surgical operation. For the purposes of example only, the surgical attachments are described hereinbelow as being circular clamping, cutting and stapling devices that are configured to perform, e.g., an anastomosis procedure. However, it should be recognized that the surgical attachments may be any suitable type of surgical device. Furthermore, for the purposes of example only, the surgical attachments described hereinbelow are described as being employed within an oral passage of a patient. However, it should be recognized that the surgical attachments may be employed within any type of orifice or passage of a patient. Advantageously, the surgical attachments described hereinbelow have a relatively small cross-sectional area, thereby facilitating its passage into, e.g., the oral passages, of a patient.

The surgical attachment 100 may include a handle portion 102. A proximal end 102a of the handle portion 102 is attachable to the coupling 26 at the distal end 24 of the flexible cable 20. The surgical attachment 100 may also include a flexible shaft 104, through which extends at least a first drive shaft 104a and a second drive shaft 104b. A distal end 102 b of the handle portion 102 is attachable to a proximal end 104a of the flexible shaft 104. The flexible shaft 104 may be formed of a tissue-compatible, sterilizable elastomeric material. Preferably, the flexible shaft 104 may be formed of a material that is autoclavable. In addition, the flexible shaft 104 may be formed of a material having a high or relatively high lubricity. For instance, the flexible shaft 104 may be formed of a material such as Teflon™ (i.e., a fluoropolymer, e.g., polytetrafluoroethylene—"PTFE"), silicone, a Teflon™/silicone combination, such as, for example, SIL-KORE™ (made by W.L. Gore & Associates), "EPTFE", e.g., expanded teflon, etc. Other suitable materials and sealing arrangements that may be employed are described in further detail in Applicants' co-pending U.S. patent application Ser. No. 10/099,634, filed on Mar. 15, 2002 (now U.S. Pat. No. 7,951,071), which is expressly incorporated herein by reference in its entirety.

The surgical attachment 100 may also include cutting and stapling component 103. A distal end 104*b* of the flexible shaft 104 is attached or attachable to a proximal end 103*a* of the cutting and stapling component 103. One example embodiment of the cutting and stapling component 103 is illustrated in FIGS. 8 to 12(*c*). As shown in FIG. 8, the cutting and stapling component 103 includes an staple and blade portion 106. Extending in an axial direction through a centrally disposed opening of the staple and blade portion 106 is a trocar shaft 108, e.g., a cable that may be flexible. Disposed at a distal end 108*a* of the trocar shaft 108 is a trocar 110. The trocar 110 is configured to engage an anvil assembly 112. The surgical attachment 100 is configured such that the anvil assembly 112 may be selectively moved, e.g., extended and retracted, relative to the staple and blade portion 106, as set forth more fully below.

Figure 2:
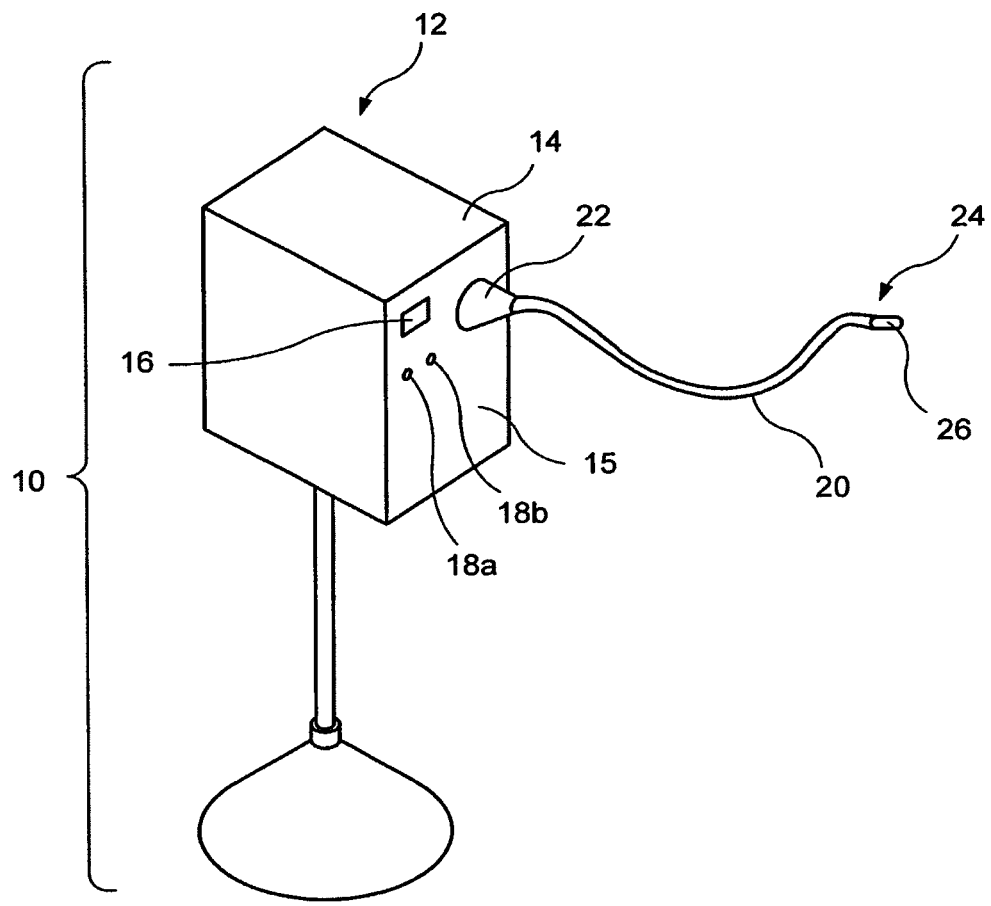
FIG. 2 is a perspective view of a remote power console, according to one embodiment of the present invention.

Referring to FIG. 2, there is seen a perspective view of the remote power console 12 and the flexible shaft 20 of the electromechanical surgical system 10, according to an example embodiment of the present invention. The remote power console 12 may include a housing 14 having a front panel 15. Mounted on front panel 15 are a display device 16 and indicators 18 *a*, 18 *b*, which are more fully described hereinbelow. The flexible shaft 20 may extend from the housing 14 and may be detachably secured thereto via a first coupling 22. The distal end 24 of the flexible shaft 20 may include a second coupling, for instance coupling 26, adapted to detachably secure the surgical attachment 100 to the distal end 24 of the flexible shaft 20.

Figure 3:
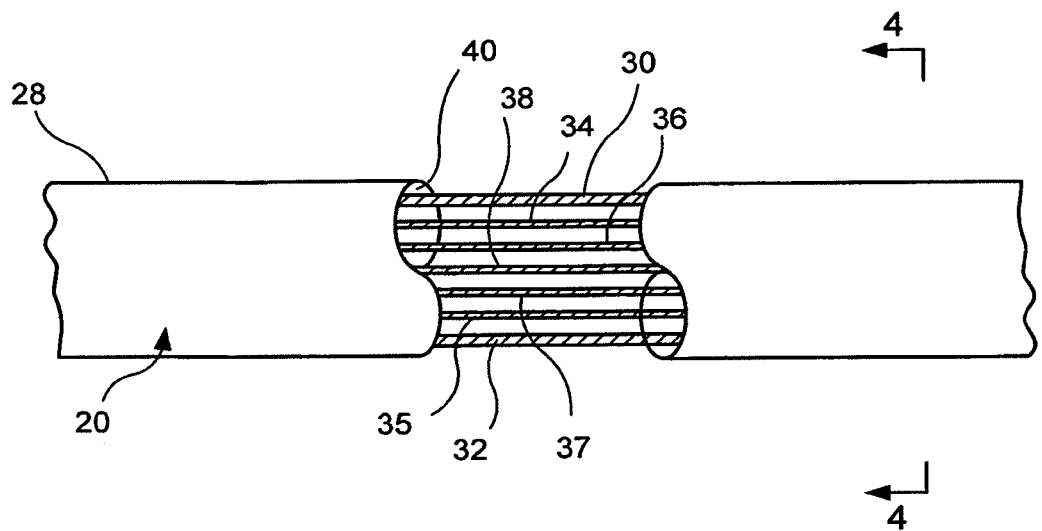
FIG. 3 is a side elevational view, partially in section, of a flexible shaft of the electromechanical surgical system illustrated in FIG. 1.
Figure 4:
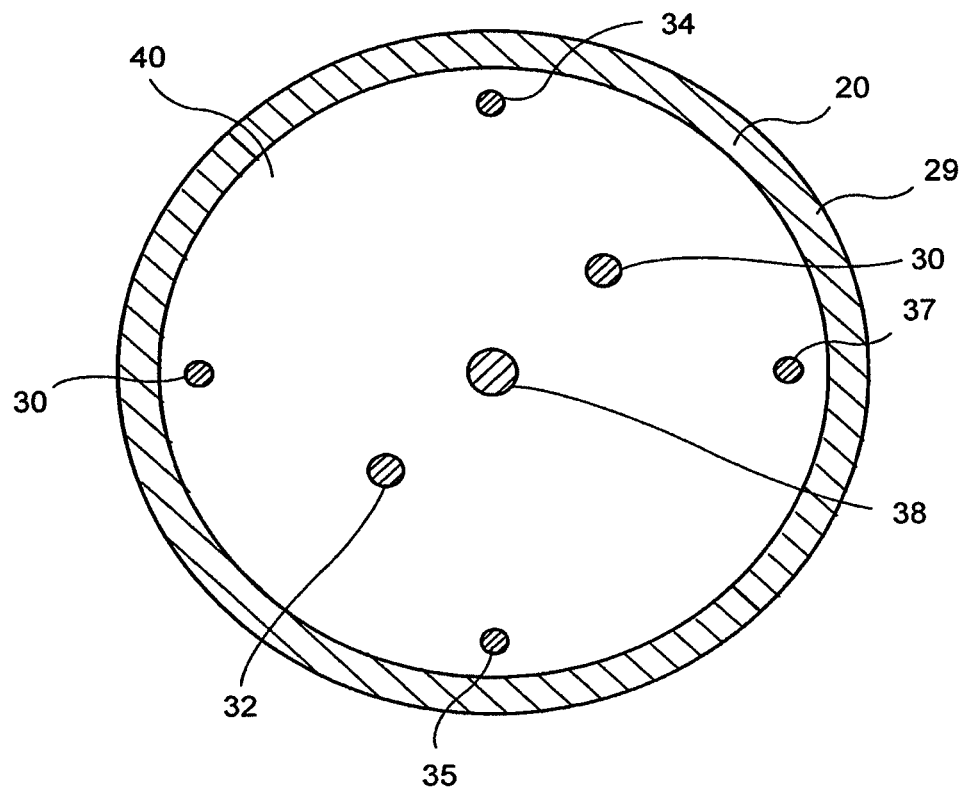
FIG. 4 is a cross-sectional view of the flexible shaft taken along the line 4-4 shown in FIG. 3.

Referring to FIG. 3, there is seen a side view, partially in section, of the flexible shaft 20. According to one embodiment, the flexible shaft 20 includes a tubular sheath 28, which may include a coating or other sealing arrangement to provide a fluid-tight seal between the interior channel 40 thereof and the environment. The sheath 28 may be formed of a tissue-compatible, sterilizable elastomeric material such as the materials enumerated above in connection with flexible shaft 104. In addition, the sheath 28 may also be formed of a material that is autoclavable. Disposed within the interior channel 40 of the flexible shaft 20, and extending along the entire length thereof, are the first rotatable drive shaft 30 and the second rotatable drive shaft 32, as well as a first steering cable 34, a second steering cable 35, a third steering cable 36, a fourth steering cable 37 and a data transfer cable 38. FIG. 4 is a cross-sectional view of the flexible shaft 20 taken along the line 4-4 shown in FIG. 3 and further illustrates the several cables 30, 32, 34, 35, 36, 37, 38. Each distal end of the steering cables 34, 35, 36, 37 is affixed to the distal end 24 of the flexible shaft 20. Each of the several cables 30, 32, 34, 35, 36, 37, 38 may be contained within a respective sheath.

The first rotatable drive shaft 30 and the second rotatable drive shaft 32 may be configured, for example, as highly flexible drive shafts, such as, for example, braided or helical drive cables. It should be understood that such highly flexible drive cables have limited torque transmission characteristics and capabilities. It should also be understood that the surgical attachment 100 illustrated in FIG. 1 and described hereinbelow, may require a higher torque input than the torque transmittable by the first and second rotatable drive shafts 30, 32. The first and second rotatable drive shafts 30, 32 may thus be configured to transmit low torque but high speed, the high speed/low torque being converted to low speed/high torque by gearing arrangements disposed, for example, at the distal end 24 and/or a proximal end 20 *a* of the drive flexible shaft 20, in the surgical attachment 100 and/or in the remote power console 12. It should be appreciated that such gearing arrangement(s) may be provided at any suitable location along the power train between the motors disposed in the housing 14 and the surgical attachment 100 that is detachably attachable to the flexible shaft 20. Such gearing arrangement(s) may include, for example, a spur gear arrangement, a planetary gear arrangement, a harmonic gear arrangement, cycloidal drive arrangement, an epicyclic gear arrangement, etc.

Referring now to FIG. 5(*a*), there is seen a rear end view of the first coupling 22. The first coupling 22 includes a first connector 44, a second connector 48, a third connector 52 and a fourth connector 56, each rotatably secured to the first coupling 22. Each of the connectors 44, 48, 52, 56 includes a respective recess 46, 50, 54, 58. As shown in FIG. 5(*a*), each recess 46, 50, 54, 58 may be hexagonally shaped. It should be appreciated, however, that the recesses 46, 50, 54, 58 may have any shape and configuration to non-rotatably couple and rigidly attach the connectors 44, 48, 52, 56 to respective drive shafts of the motor arrangement contained within the housing 12, as more fully described below. It should be appreciated that complementary projections may be provided on respective drive shafts of the motor arrangement to thereby drive the drive elements of the flexible shaft 20 as described below. It should also be appreciated that the recesses may be provided on the drive shafts and complementary projections may be provided on the connectors 44, 48, 52, 56. Any other coupling arrangement configured to non-rotatably and releasably couple the connectors 44, 48, 52, 56 and the drive shafts of the motor arrangement may be provided.

One of the connectors 44, 48, 52, 56 is non-rotatably secured to the first rotatable drive shaft 30, and another one of the connectors 44, 48, 52, 56 is non-rotatably secured to the second rotatable drive shaft 32. The remaining two of the connectors 44, 48, 52, 56 engage with transmission elements configured to apply tensile forces on the steering cables 34, 35, 36, 37 to thereby steer the distal end 20*b* of the flexible shaft 20. The data transfer cable 38 is electrically and logically connected with a data connector 60. The data connector 60 includes, for example, electrical contacts 62, corresponding to and equal in number to the number of individual wires contained in the data cable 38. The first coupling 22 includes a key structure 42 to properly orient the first coupling 22 to a mating and complementary coupling arrangement disposed on the remote power console 12. Such key structure 42 may be provided on either one, or both, of the first coupling 22 and the mating and complementary coupling arrangement disposed on the remote power console 12. The first coupling 22 may include a quick-connect type connector, which may use, for example, a simple pushing motion to engage the first coupling 22 to the housing 12. Seals may be provided in conjunction with any of the several connectors 44, 48, 52, 56, 60 to provide a fluid-tight seal between the interior of the first coupling 22 and the environment.

Referring now to FIG. 5(*b*), there is seen a front end view of the second coupling 26 of the flexible shaft 20. The second coupling 26 includes a first connector 66 and a second connector 68, each being rotatably secured to the second coupling 26 and each being non-rotatably secured to a distal end of a respective one of the first and second rotatable drive shafts 30, 32. A quick-connect type fitting 64 is provided on the second coupling 26 for detachably securing the surgical attachment 100 thereto. The quick-connect type fitting 64 may be, for example, a rotary quick-connect type fitting, a bayonet type fitting, etc. A key structure 74 is provided on the second coupling 26 for properly aligning the surgical instrument or attachment to the second coupling 26. The key structure 74 or other arrangement for properly aligning the surgical attachment 100 to the flexible shaft 20 may be provided on either one, or both, of the second coupling 26 and the surgical attachment 100. In addition, the quick-connect type fitting may be provided on the surgical attachment 100. A data connector 70, having electrical contacts 72, is also provided in the second coupling 26. Like the data connector 60 of the first coupling 22, the data connector 70 of the second coupling 26 includes contacts 72 electrically and logically connected to the respective wires of the data transfer cable 38 and the contacts 62 of the data connector 60. Seals may be provided in conjunction with the connectors 66, 68, 70 to provide a fluid-tight seal between the interior of second coupling 26 and the environment.

Disposed within housing 14 of the remote power console 12 are electro-mechanical driver elements configured to drive the drive shafts 30, 32 and the steering cables 34, 35, 36, 37 to thereby operate the electro-mechanical surgical system 10 and the surgical attachment 100 attached to the second coupling 26. In the example embodiment illustrated schematically in FIG. 6(*a*), five electric motors 76, 80, 84, 90, 96, each operating via a power source, may be disposed in the remote power console 12. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 6A:
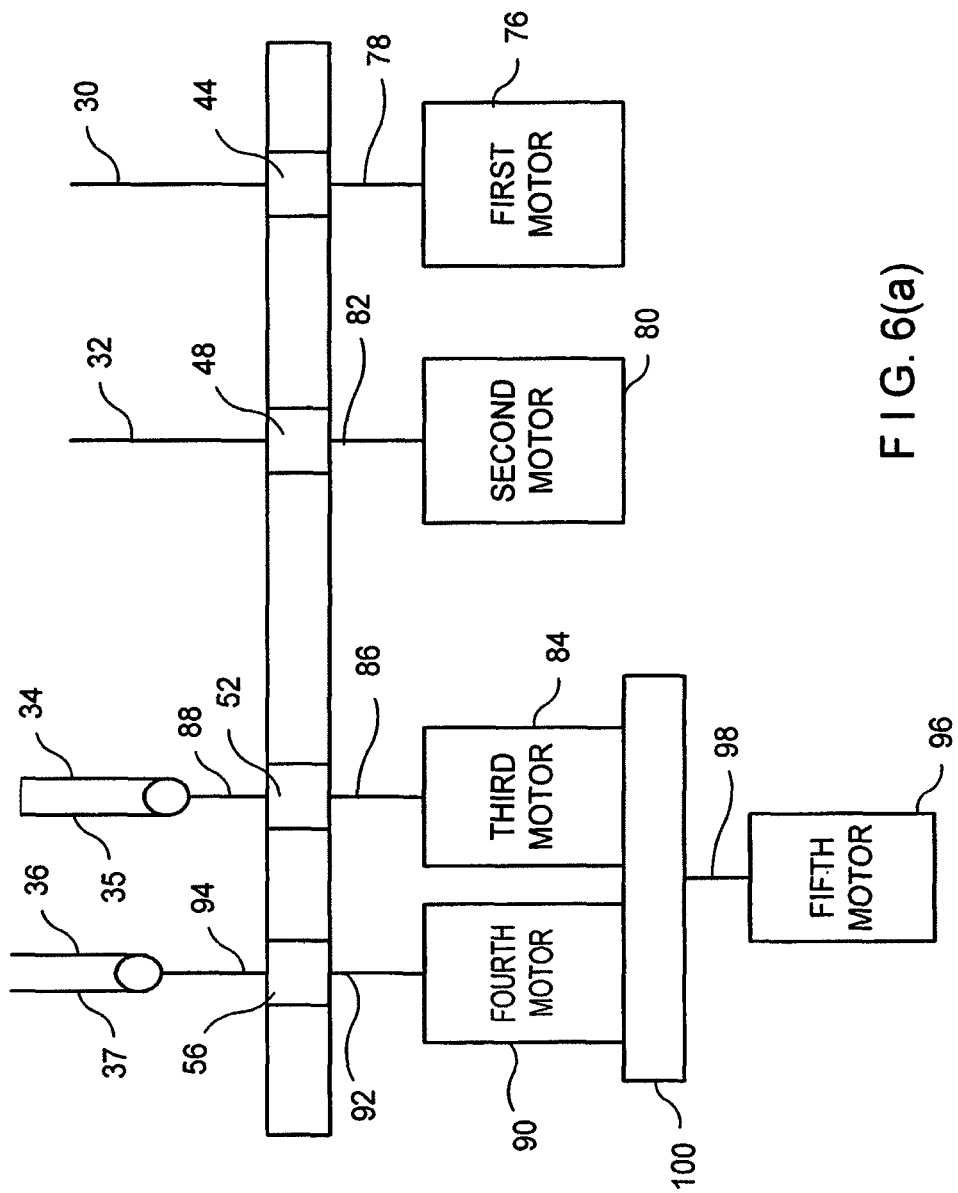
FIG. 6(a) is a schematic view illustrating a motor arrangement of the electro-mechanical surgical system illustrated in FIG. 1.
Figure 6E:
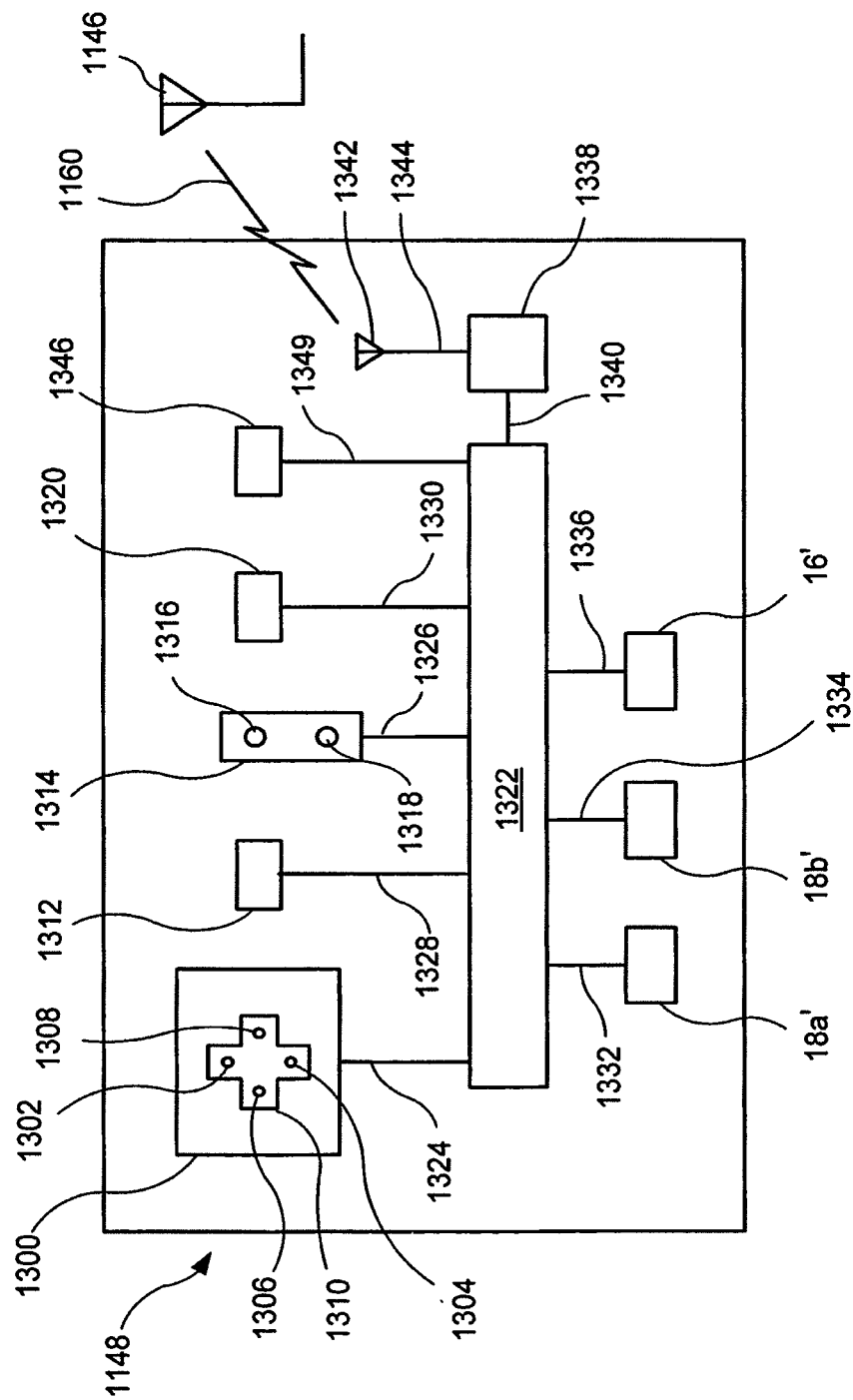
FIG. 6(e) is a schematic view of a wireless RCU, according to one embodiment of the present invention.
Figure 6F:
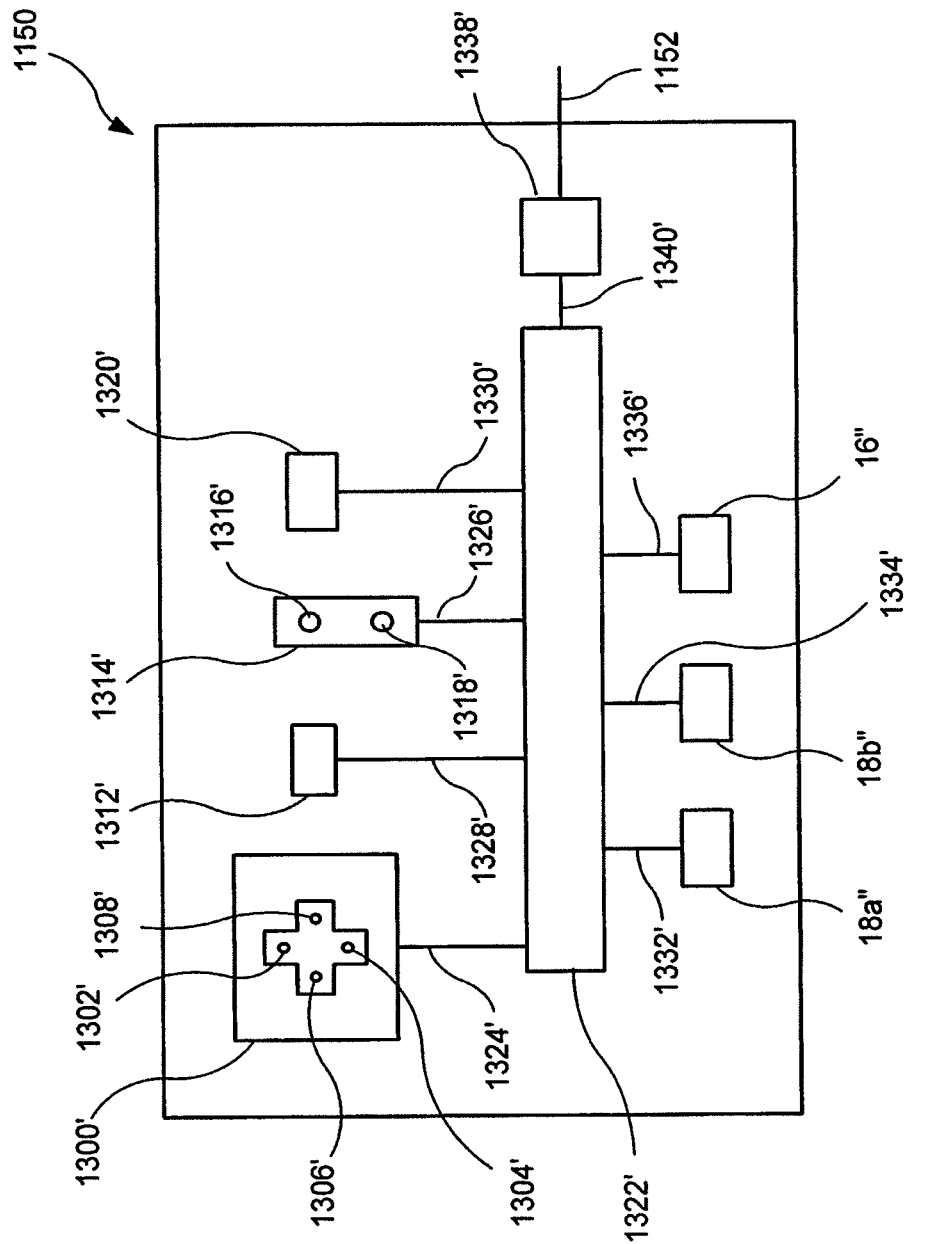
FIG. 6(f) is a schematic view of a wired RCU, according to one embodiment of the present invention.

FIG. 6(*a*) illustrates schematically one possible arrangement of motors. An output shaft 78 of a first motor 76 engages with the first connector 44 of the first coupling 22 when the first coupling 22, and, therefore, flexible shaft 20, is engaged with the housing 14 to thereby drive the first drive shaft 30 and first connector 66 of second coupling 26. Similarly, an output shaft 82 of a second motor 80 engages the second connector 48 of first coupling 22 when first coupling 22, and, therefore, flexible shaft 20 is engaged with the housing 14 to thereby drive the second drive shaft 32 and second connector 68 of second coupling 26. An output shaft 86 of a third motor 84 engages the third connector 52 of the first coupling 22 when the first coupling 22, and, therefore, flexible shaft 20, is engaged with the housing 14 to thereby drive the first and second steering cables 34, 35 via a first pulley arrangement 88. An output shaft 92 of a fourth motor 90 engages the fourth connector 56 of the first coupling 22 when the first coupling 22, and, therefore, flexible shaft 20, is engaged with the housing 14 to thereby drive the third and fourth steering cables 36, 37 via a second pulley arrangement 94. The third and fourth motors 84, 90 may be secured on a carriage 100, which is selectively movable via an output shaft 98 of a fifth motor 96 between a first position and a second position to selectively engage and disengage the third and fourth motors 84, 90 with the respective pulley arrangement 88, 94 to thereby permit the flexible shaft 20 to become taut and steerable or limp as necessary. It should be appreciated that other mechanical, electrical or electromechanical mechanisms may be used to selectively engage and disengage the steering mechanism. The motors may be arranged and configured as described, for example, in U.S. patent application Ser. No. 09/510,923, filed on Feb. 22, 2000, entitled "A Carriage Assembly for Controlling a Steering Wire Mechanism Within a Flexible Shaft," (now U.S. Pat. No. 6,517,565) which is expressly incorporated herein in its entirety by reference thereto.

It should be appreciated, that any one or more of the motors 76, 80, 84, 90, 96 may be high-speed/low-torque motors or low-speed/high-torque motors. As indicated above, the first rotatable drive shaft 30 and the second rotatable drive shaft 32 may be configured to transmit high speed and low torque. Thus, the first motor 76 and the second motor 80 may be configured as high-speed/low-torque motors. Alternatively, the first motor 76 and the second motor 80 may be configured as low-speed/high-torque motors with a torque-reducing/speed-increasing gear arrangement disposed between the first motor 76 and the second motor 80 and a respective one of the first rotatable drive shaft 30 and the second rotatable drive shaft 32. Such torque-reducing/speed-increasing gear arrangement may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 12 or in the proximal end of the flexible shaft 20, such as, for example, in the first coupling 22. It should be appreciated that the gear arrangement(s) are provided at the distal and/or proximal ends of the first rotatable drive shaft 30 and/or the second rotatable drive shaft 32 to prevent windup and breakage thereof.

Referring now to FIG. 6(*b*), there is seen a schematic view of the electro-mechanical surgical system 10. A controller 1122 is provided in the housing 14 of the remote power console 12 and is configured to control all functions and operations of the electro-mechanical surgical system 10 and the surgical attachment 100 attached to the flexible shaft 20. A memory unit 1130 is provided and may include memory devices, such as, a ROM component 1132 and/or a RAM component 1134. The ROM component 1132 is in electrical and logical communication with the controller 1122 via line 1136, and the RAM component 1134 is in electrical and logical communication with the controller 1122 via line 1138. The RAM component 1134 may include any type of random-access memory, such as, for example, a magnetic memory device, an optical memory device, a magneto-optical memory device, an electronic memory device, etc. Similarly, the ROM component 1132 may include any type of read-only memory, such as, for example, a removable memory device, such as a PC-Card or PCMCIA-type device. It should be appreciated that the ROM component 1132 and the RAM component 1134 may be embodied as a single unit or may be separate units and that the ROM component 1132 and/or the RAM component 1134 may be provided in the form of a PC-Card or PCMCIA-type device. The controller 1122 is further connected to the front panel 15 of the housing 14 and, more particularly, to the display device 16 via line 1154 and the indicators 18 *a*, 18 *b* via respective lines 1156, 1158. The lines 1116, 1118, 1124, 1126, 1128 electrically and logically connect the controller 1122 to the first, second, third, fourth and fifth motors 76, 80, 84, 90, 96, respectively. A wired remote control unit ("RCU") 1150 is electrically and logically connected to the controller 1122 via line 1152. A wireless RCU 1148 is also provided and communicates via a wireless link 1160 with a receiving/sending unit 1146 connected via line 1144 to a transceiver 1140. The transceiver 1140 is electrically and logically connected to the controller 1122 via line 1142. The wireless link 1160, may be, for example, an optical link, such as an infrared link, a radio link or any other form of wireless communication link.

A switch device 1186, which may be, for example, an array of DIP switches, may be connected to the controller 1122 via line 1188. The switch device 1186 may be used, for example, to select one of a plurality of languages used in displaying messages and prompts on the display device 16. The messages and prompts may relate to, for example, the operation and/or the status of the electro-mechanical surgical system 10 and/or to the surgical attachment attached thereto.

According to the example embodiment of the present invention, a first encoder 1106 is provided within the second coupling 26 and is configured to output a signal in response to and in accordance with the rotation of the first drive shaft 30. A second encoder 1108 is also provided within the second coupling 26 and is configured to output a signal in response to and in accordance with the rotation of the second drive shaft 32. The signal output by each of the encoders 1106, 1108 may represent the rotational position of the respective drive shaft 30, 32 as well as the rotational direction thereof. Such encoders 1106, 1108 may be, for example, Hall-effect devices, optical devices, etc. Although the encoders 1106, 1108 are described as being disposed within the second coupling 26, it should be appreciated that the encoders 1106, 1108 may be provided at any location between the motor system and the surgical instrument or attachment. It should be appreciated that providing the encoders 1106, 1108 within the second coupling 26 or at the distal end of the flexible shaft 20 provides for an accurate determination of the drive shaft rotation. If the encoders 1106, 1108 are disposed at the proximal end of the flexible shaft 20, windup of the first and second rotatable drive shafts 30, 32 may result in measurement error.

FIG. 6(c) is a schematic view of an encoder 1106, 1108, which includes a Hall-effect device. Mounted non-rotatably on drive shaft 30, 32 is a magnet 240 having a north pole 242 and a south pole 244. The encoder 1106, 1108 further includes a first sensor 246 and second sensor 248, which are disposed approximately 90° apart relative to the longitudinal, or rotational, axis of drive shaft 30, 32. The output of the sensors 246, 248 is persistent and changes its state as a function of a change of polarity of the magnetic field in the detection range of the sensor. Thus, based on the output signal from the encoders 1106, 1108, the angular position of the drive shaft 30, 32 may be determined within one-quarter revolution and the direction of rotation of the drive shaft 30, 32 may be determined. The output of each encoder 1106, 1108 is transmitted via a respective line 1110, 1112 of data transfer cable 38 to controller 1122. The controller 1122, by tracking the angular position and rotational direction of the drive shafts 30, 32 based on the output signal from the encoders 1106, 1108, can thereby determine the position and/or state of the components of the surgical attachment 100 connected to the electromechanical surgical system 10. That is, by counting the revolutions of the drive shaft 30, 32, the controller 1122 can determine the position and/or state of the components of the surgical attachment 100 connected to the electromechanical surgical system 10.

The surgical attachment 100 may further include, according to one embodiment and as shown in FIG. 6(d), a data connector 1272 adapted by size and configuration to electrically and logically connect to the connector 70 of the second coupling 26. In the example embodiment, the data connector 1272 includes contacts (not shown) equal in number to the number of leads 72 of the connector 70. Contained within the surgical attachment 100 is a memory unit 1174 electrically and logically connected with the data connector 1272. The memory unit 1174 may be in the form of, for example, an EEPROM, EPROM, etc. and may be contained, for example, within the staple and blade portion 106 of the surgical attachment 100.

FIG. 6(d) schematically illustrates the memory unit 1174. As seen in FIG. 6(d), the data connector 1272 includes contacts 1276, each electrically and logically connected to the memory unit 1174 via a respective line 1278. The memory unit 1174 is configured to store, for example, a serial number data 1180, an attachment type identifier (ID) data 1182 and a usage data 1184. The memory unit 1174 may additionally store other data. Both the serial number data 1180 and the ID data 1182 may be configured as read-only data. In the example embodiment, the serial number data 1180 is data uniquely identifying the particular surgical attachment, whereas the ID data 1182 is data identifying the type of the attachment (when, for instance, other types of attachments may be employed by the device). The usage data 1184 represents usage of the particular attachment, such as, for example, the number of times the anvil assembly 112 of the surgical attachment 100 has been retracted or extended, or the number of times that the staple pusher 220 of the surgical attachment 100 has been advanced or fired, as set forth more fully below.

It should be appreciated that the surgical attachment 100 attachable to the distal end 24 of the flexible shaft 20 may be designed and configured to be used a single time or multiple times. The surgical attachment 100 may also be designed and configured to be used a predetermined number of times. Accordingly, the usage data 1184 may be used to determine whether the surgical attachment 100 has been used and whether the number of uses has exceeded the maximum number of permitted uses. As more fully described below, an attempt to use the surgical attachment 100 after the maximum number of permitted uses has been reached will generate an ERROR condition.

Referring again to FIG. 6(b), in accordance with the example embodiment of the present invention, the controller 1122 is configured to read the ID data 1182 from the memory unit 1174 of the surgical attachment 100 when the surgical attachment 100 is initially connected to the flexible shaft 20. The memory unit 1174 is electrically and logically connected to the controller 1122 via line 1120 of data transfer cable 38. Based on the read ID data 1182, the controller 1122 is configured to read or select from the memory unit 1130, an operating program or algorithm corresponding to the type of surgical instrument or attachment connected to the flexible shaft 20. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory unit 1174 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electromechanical surgical system 10. It should be appreciated that the serial number data 1180 and/or the usage data 1184 may also be used to determine which of a plurality of operating programs or algorithms is read or selected from the memory unit 1130. It should be appreciated that the operating program or algorithm may alternatively be stored in the memory unit 1174 of the surgical attachment 100 and transferred to the controller 1122 via the data transfer cable 38. Once the appropriate operating program or algorithm is read or selected by, or transmitted to, the controller 1122, the controller 1122 causes the operating program or algorithm to be executed in accordance with operations performed by the user via the wired RCU 1150 and/or the wireless RCU 1148. As indicated hereinabove, the controller 1122 is electrically and logically connected with the first, second, third, fourth and fifth motors 76, 80, 84, 90, 96 via respective lines 1116, 1118, 1124, 1126, 1128 and controls such motors 76, 80, 84, 90, 96 in accordance with the read, selected or transmitted operating program or algorithm via the respective lines 1116, 1118, 1124, 1126, 1128.

Referring now to FIG. 6(*e*), there is seen a schematic view of a wireless RCU 1148. The wireless RCU 1148 includes a steering controller 1300 having a plurality of switches 1302, 1304, 1306, 1308 arranged under a four-way rocker 1310. The operation of switches 1302, 1304, via the rocker 1310, controls the operation of the first and second steering cables 34, 35 via the third motor 84. Similarly, the operation of the switches 1306, 1308, via the rocker 1310, controls the operation of the third and fourth steering cables 36, 37 via the fourth motor 92. It should be appreciated that the rocker 1310 and the switches 1302, 1304, 1306, 1308 are arranged so that the operation of the switches 1302, 1304 steers the flexible shaft 20 in the north-south direction and that the operation of the switches 1306, 1308 steers the flexible shaft 20 in the east-west direction. Reference herein to north, south, east and west is made to a relative coordinate system. Alternatively, a digital joystick, analog joystick, etc. may be provided in place of the rocker 1310 and the switches 1302, 1304, 1306, 1308. Potentiometers or any other type of actuator may also be used in place of the switches 1302, 1304, 1306, 1308.

The wireless RCU 1148 further includes a steering engage/disengage switch 1312, the operation of which controls the operation of the fifth motor 96 to selectively engage and disengage the steering mechanism. The wireless RCU 1148 also includes a two-way rocker 1314 having first and second switches 1316, 1318 operable thereby. The operation of these switches 1316, 1318 controls certain functions of the electro-mechanical surgical system 10 and any surgical attachment, such as surgical attachment 100, attached to the flexible shaft 20 in accordance with the operating program or algorithm corresponding to the attached surgical attachment, if any. For example, where the surgical instrument is the surgical attachment 100, such as that shown in FIG. 1 and described hereinbelow, operation of the two-way rocker 1314 may control the extension and retraction of the anvil assembly 112 of the surgical attachment 100. The wireless RCU 1148 is provided with yet another switch 1320, the operation of which may further control the operation of the electro-mechanical surgical system 10 and any surgical attachment attached to the flexible shaft 20 in accordance with the operating program or algorithm corresponding to the attached surgical attachment, if any. For example, when the surgical attachment 100 is attached to the flexible shaft 20, operation of the switch 1320 may initiate the advancement, or firing sequence, of the staple pusher 220.

The wireless RCU 1148 includes a controller 1322, which is electrically and logically connected with the switches 1302, 1304, 1306, 1308 via line 1324, with the switches 1316, 1318 via line 1326, with the switch 1312 via line 1328 and with the switch 1320 via line 1330. The wireless RCU 1148 may include indicators 18 *a'*, 18 *b'*, corresponding to the indicators 18 *a*, 18 *b* of the front panel 15, and a display device 16', corresponding to the display device 16 of the front panel 15. If provided, the indicators 18 *a'*, 18 *b'* are electrically and logically connected to the controller 1322 via respective lines 1332, 1334, and the display device 16' is electrically and logically connected to the controller 1322 via line 1336. The controller 1322 is electrically and logically connected to a transceiver 1338 via line 1340, and the transceiver 1338 is electrically and logically connected to a receiver/transmitter 1342 via line 1344. A power supply, not shown, for example, a battery, may be provided in the wireless RCU 1148 to power the same. Thus, the wireless RCU 1148 may be used to control the operation of the electromechanical surgical system 10 and any surgical attachment 100 attached to the flexible shaft 20 via wireless link 1160.

The wireless RCU 1148 may include a switch 1346 connected to the controller 1322 via line 1348. Operation of the switch 1346 transmits a data signal to the transmitter/receiver 1146 via the wireless link 1160. The data signal includes identification data uniquely identifying the wireless RCU 1148. This identification data is used by the controller 1122 to prevent unauthorized operation of the electro-mechanical surgical system 10 and to prevent interference with the operation of the electromechanical surgical system 10 by another wireless RCU. Each subsequent communication between the wireless RCU 1148 and the electromechanical surgical system 10 may include the identification data. Thus, the controller 1122 can discriminate between wireless RCUs and thereby allow only a single, identifiable wireless RCU 1148 to control the operation of the electro-mechanical surgical system 10 and any surgical attachment attached to the flexible shaft 20.

Based on the positions of the components of the surgical attachment 100 attached to the flexible shaft 20, as determined in accordance with the output signals from the encoders 1106, 1108, the controller 1122 may selectively enable or disable the functions of the electromechanical surgical system 10 as defined by the operating program or algorithm corresponding to the attached surgical attachment 100. For example, where the surgical attachment is the surgical attachment 100 illustrated in FIG. 1, the firing function controlled by the operation of the switch 1320 is disabled unless the space or gap between the anvil assembly 112 and the staple and blade portion 106 is determined to be within an acceptable range. The space or gap between the anvil assembly 112 and the staple and blade portion 106 is determined based on the output signal from the encoders 1106, 1108, as more fully described hereinabove. It should be appreciated that the switch 1320 itself remains operable but that the controller 1122 does not effect the corresponding function unless the space or gap is determined to be within the acceptable range.

Referring now to FIG. 6(*f*), there is seen a schematic view of a wired RCU 1150. In the example embodiment, the wired RCU 1150 includes substantially the same control elements as the wireless RCU 1148 and further description of such elements is omitted. Like elements are noted in FIG. 6(*f*) with an accompanying prime. It should be appreciated that the functions of the electromechanical surgical system 10 and any surgical attachment attached to the flexible shaft 20 may be controlled by the wired RCU 1150 and/or by the wireless RCU 1148. In the event of a battery failure, for example, in the wireless RCU 1148, the wired RCU 1150 may be used to control the functions of the electromechanical surgical system 10 and any surgical attachment 100 attached to the flexible shaft 20.

As described hereinabove, the front panel 15 of housing 14 includes display device 16 and indicators 18a, 18b. The display device 16 may include an alpha-numeric display device, such as an LCD display device. The display device 16 may also include an audio output device, such as a speaker, a buzzer, etc. The display device 16 is operated and controlled by controller 1122 in accordance with the operating program or algorithm corresponding to a surgical attachment 100 attached to the flexible shaft 20. If no surgical attachment is so attached, a default operating program or algorithm may be read or selected by, or transmitted to, controller 1122 to thereby control the operation of the display device 16 as well as the other aspects and functions of the electromechanical surgical system 10. If the surgical attachment 100 illustrated in FIG. 1 is attached to flexible shaft 20, display device 16 may display, for example, data indicative of the gap between the anvil assembly 112 and the staple and blade portion 106 as determined in accordance with the output signal of encoders 1106, 1108, as more fully described hereinabove.

Similarly, the indicators 18a, 18b are operated and controlled by the controller 1122 in accordance with the operating program or algorithm corresponding to the surgical attachment 100 attached to the flexible shaft 20. The indicator 18a and/or the indicator 18b may include an audio output device, such as a speaker, a buzzer, etc., and/or a visual indicator device, such as an LED, a lamp, a light, etc. If the surgical attachment 100 illustrated in FIG. 1 is attached to the flexible shaft 20, the indicator 18a may indicate, for example, that the electromechanical surgical system 10 is in a power ON state, and the indicator 18 b may, for example, indicate whether the gap between the anvil assembly 112 and the staple and blade portion 106 is determined to be within the acceptable range as more fully described hereinabove. It should be appreciated that although only two indicators 18a, 18b are described, any number of additional indicators may be provided as necessary. Additionally, it should be appreciated that although a single display device 16 is described, any number of additional display devices may be provided as necessary.

The display device 16' and the indicators 18a', 18b' of the wireless RCU 1150 and the display device 16" and the indicators 18a", 18b" of the wired RCU 1148 are similarly operated and controlled by the respective controller 1322, 1322' in accordance with the operating program or algorithm corresponding to the surgical attachment 100 attached to the flexible shaft 20.

Hereinbelow is described the surgical attachment 100 illustrated for instance in FIG. 1, in accordance with various embodiments of the present invention.

Figures 7A, 7B:
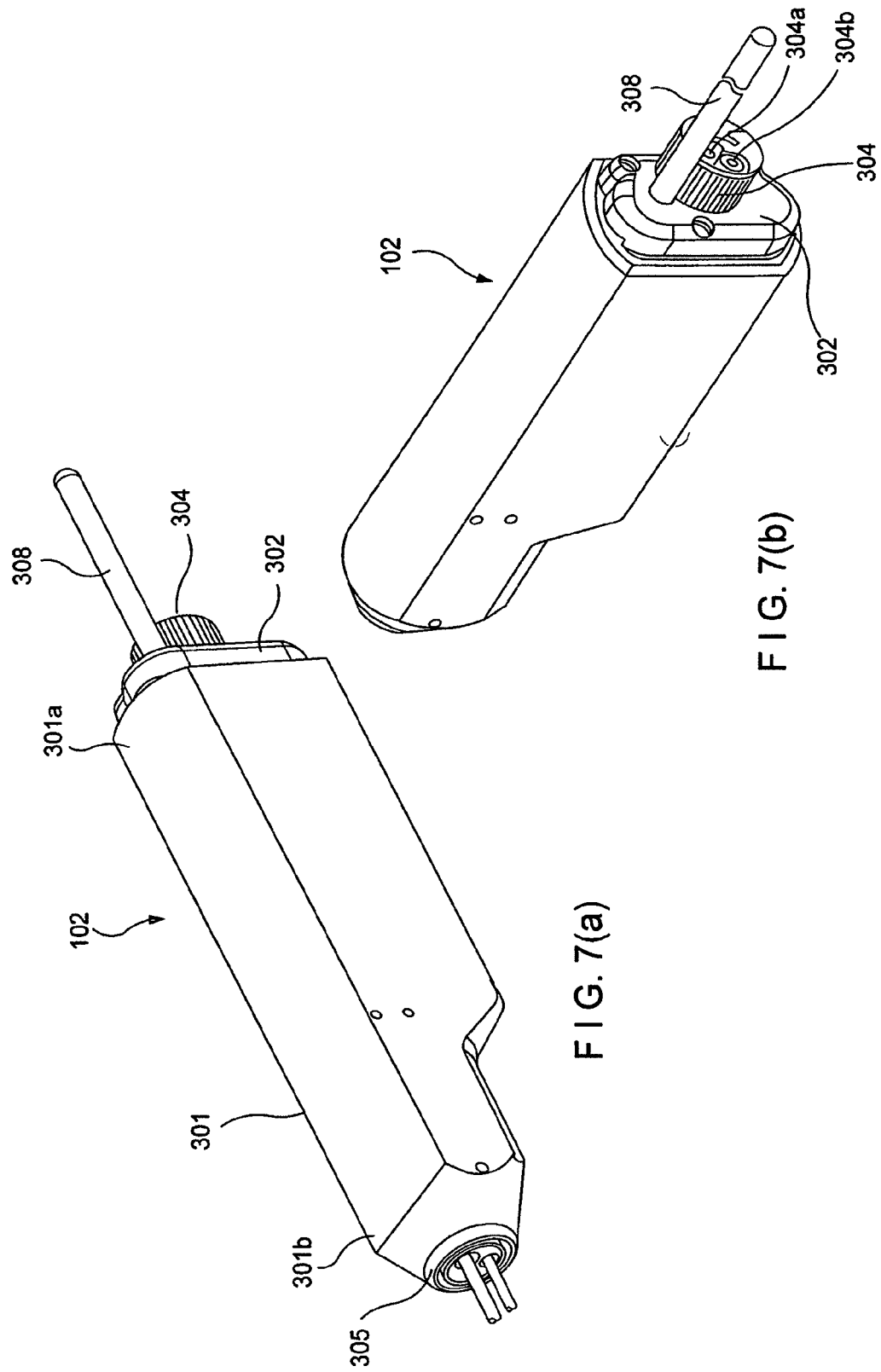
FIG. 7(a) is a front perspective view of a handle portion, according to one embodiment of the present invention.
FIG. 7(b) is a rear perspective view of the handle portion shown in FIG. 7(a).

FIGS. 7(a) to 7(f) are various views of the handle portion 102 of the surgical attachment 100, according to one embodiment of the present invention. For instance, FIG. 7(a) is a front perspective view, and FIG. 7(b) is a rear perspective view, of the handle portion 102 including a housing 301. At a proximal end 301a of the housing 301 is disposed a gear housing 302. At a distal end 301b of the housing 301 is disposed a coupling block 305. Extending from the gear housing 302 is a quick connect coupling 304 and an extension rod 308.

The quick-connect coupling 304 is mounted onto the gear housing 302 and may be biased, e.g., via a set of springs. The gear housing 302 includes a first drive socket 304a and a second drive socket 304b. FIG. 7(c) is an exploded front perspective view of the handle portion 102. As shown in FIG. 7(c), the first drive socket 304a includes a first input element 306a, one end 3061 of which extends through an opening 3021 of the gear housing 302 and the other end 3062 of which includes spur gear teeth 3063. The second drive socket 304b includes a second input element 306b, one end 3064 of which extends through a second opening 3022 of the gear housing 302 and the other end 3065 of which includes spur gear teeth 3066.

The extension rod 308 extends through an extension rod opening 3025 in the gear housing 302. The distal end 308b of the extension rod 308 has a flange 3081 that is larger than the extension rod opening 3025 such that the flange 3081 of the extension rod 308 is retained within the gear housing 302. The flange 3081 of the extension rod 308 abuts one side of the spur gear 310, the spur gear 310 being seated within an internal recess 3023 of the gear housing 302. The spur gear 310 has arranged along its outer circumference spur gear teeth 3101 that correspond to the spur gear teeth 3063 of the first input element 306a. Extending through an internally threaded bore 3102 of the spur gear 310 is externally threaded rod 312 that is arranged coaxially relative to the extension rod 308. The rod 312 is connected to a coupling element 314 that is positioned within a first opening 3052 of the coupling block 305. The rod coupling 314 may provide a connection to the first drive shaft 104a of the flexible shaft 104.

Also seated within an internal recess 3024 of the gear housing 302 is a spur gear 318. The spur gear 318 has arranged along its outer circumference spur gear teeth 3181 that correspond to the spur gear teeth 3066 of the second input element 306b. The spur gear 318 has a bore 3182 extending therethrough. Non-rotatably engaged within the bore 3182 of the spur gear 318 is a first end 3161 of a shaft drive element 316. A second end 3162 of the shaft drive element 316 is configured to non-rotatably engage the second drive shaft 104b of the flexible shaft 104, which extends through a second opening 3053 in the distal face 3051 of the coupling block 305.

FIG. 7(d) is a top view of the handle portion 102 illustrated in FIG. 7(a). FIG. 7(e) is a side cross-sectional view of the handle portion 102 illustrated in FIG. 7(d) taken along the lines A-A. FIG. 7(f) is a side cross-sectional view of the handle portion 102 illustrated in FIG. 7(d) taken along the lines B-B.

FIG. 8 is a perspective view of the cutting and stapling component 103 of the surgical attachment 100, according to one embodiment of the present invention. As shown in FIG. 8 and as previously described, the cutting and stapling component 103 includes a staple and blade portion 106. Extending in an axial direction through a centrally disposed opening of the staple and blade portion 106 is a trocar shaft 108. The trocar shaft 108 may be flexible. In one embodiment, the trocar shaft 108 is a cable. Disposed at a distal end 108a of the trocar shaft 108 is a trocar 110. The trocar 110 has a sharp or pointed end that is configured to be pushed through a section of tissue. In addition, the trocar 110 is configured to engage an anvil assembly 112, preferably by being insertable within a slot of the anvil assembly 112 for detachably fixing the trocar 110, and thus the trocar shaft 108 attached thereto, to the anvil assembly 112 as set forth more fully below. The surgical attachment 100 is configured such that the trocar shaft 108, and the anvil assembly 112 attached thereto, may be selectively moved, e.g., extended and retracted, relative to the staple and blade portion 106, as set forth more fully below. Specifically, the trocar shaft 108, having the trocar 110 disposed at its end, is extendable and retractable by movement in first and second, e.g., distal and proximal, directions, respectively, to a desired distance relative to the staple and blade portion 106.

Figure 9:
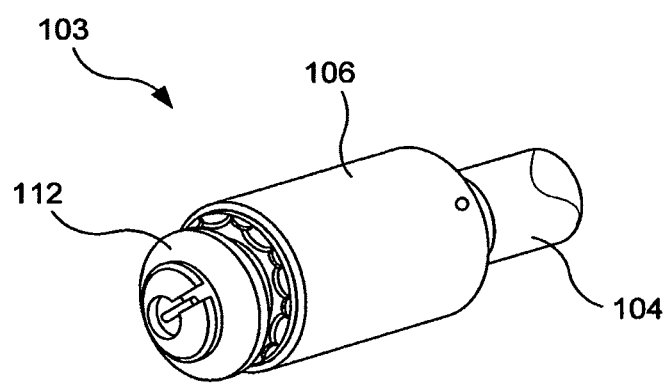
FIG. 9 is a perspective view that illustrates a cutting and stapling component in a partially closed, according to one embodiment of the present invention.

FIG. 9 is a perspective view that illustrates a cutting and stapling component 103, according to one embodiment of the present invention. FIG. 9 shows the cutting and stapling component 103 in an assembled, partially closed position. Specifically, FIG. 9 illustrates the anvil assembly 112 in a partially retracted position relative to the staple and blade portion 106.

Figure 10A:
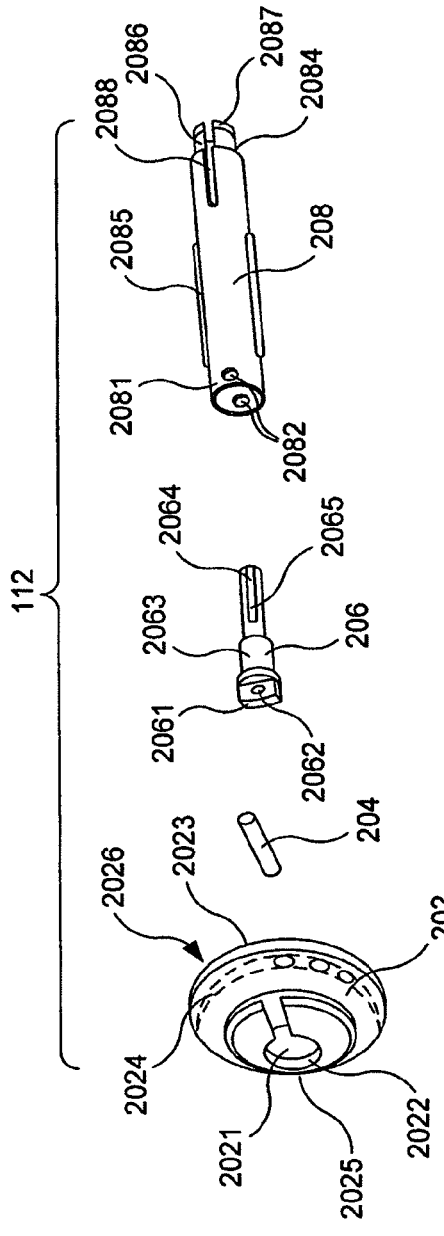
FIG. 10(a) is a perspective view that illustrates the components of an anvil assembly, according to one embodiment of the present invention.

FIG. 10(a) is a perspective view that illustrates the components of the anvil assembly 112, according to one embodiment of the present invention. FIG. 10(a) shows the anvil assembly 112 in an exploded condition. As shown in FIG. 10(a), the anvil assembly 112 includes an anvil end cap 202. The anvil end cap 202 has a centrally-disposed opening 2021 arranged in the axial direction. The anvil end cap 202 also includes a radially-disposed slot 2022 on a distal side 2025 of the end cap 202, and a clamping face 2023 on a proximal side 2026 of the anvil end cap 202. The clamping face 2023 has a recessed portion that forms a blade repository 2024. The clamping face 2023 also defines staple guides 2026.

The anvil assembly 112 also includes a pin 204 corresponding cross-sectionally to the slot 2022 of the anvil end cap 202. The anvil assembly 112 also includes a hollow anvil sleeve 208. A distal end 2081 of the anvil sleeve 208 corresponds cross-sectionally to the opening 2021 of the anvil end cap 202. In addition, the distal end 2081 of the anvil sleeve 208 defines openings 2082 that correspond cross-sectionally to the anvil pin 204. In a proximal end 2084 of the anvil sleeve 208 there is defined a recess 2086 that extends circumferentially around the anvil sleeve 208 and that has a radius that is smaller than the radius of the other portions of the anvil sleeve 208, including the radius of several radially-extending teeth 2087 located at the proximal-most end of the anvil sleeve 208. The proximal end 2084 of the anvil sleeve 208 also defines a plurality, e.g., four, axial slots 2088 that extend through the recess 2086 and the teeth 2087, thereby enabling the proximal end 2084 of the anvil sleeve 208 to be radially compressed. The anvil sleeve 208 also includes one or more longitudinally-extending keys 2085 on its outer surface.

The anvil assembly 112 also includes an anvil extension rod 206. The anvil extension rod 206 has a distal end 2061 that may be flat and that defines an opening 2062. The anvil extension rod 206 also has a central region 2063 that is round and that corresponds cross-sectionally to an inner diameter of the recess 2086 of the anvil sleeve 208. The distal end 2061 of the anvil extension rod 206 is cross-sectionally larger than the inner diameter of the recess 2086 of the anvil sleeve 208. The anvil extension rod 206 also has a proximal end 2063 that defines a trocar receiving slot 2065.

Figure 10B:
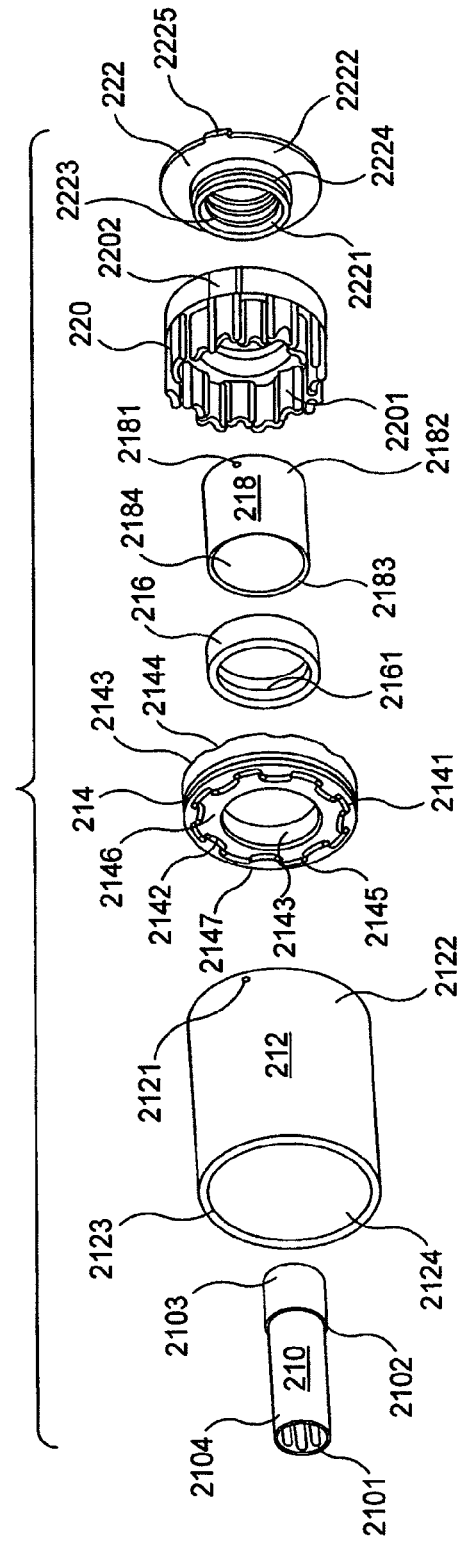
FIG. 10(b) is a perspective view that illustrates some of the components of the staple and blade portion in an exploded condition, according to one embodiment of the present invention.

FIG. 10(b) is a perspective view that illustrates some of the components of the staple and blade portion 106, according to one embodiment of the present invention. FIG. 10(b) shows the components in an exploded condition. As shown in FIG. 10(b), the staple and blade portion 106 includes a hollow anvil sleeve guide 210. The inner surface of the anvil sleeve guide 210 includes one or more keyways 2101. The outer surface of the anvil sleeve guide 210 includes a lip 2102, such that a proximal end 2103 of the anvil sleeve guide 210 has a larger radius than a distal end 2104 of the anvil sleeve guide 210.

The staple and blade portion 106 also includes an outer housing sleeve 212. The outer housing sleeve 212 has one or more openings 2121 at its distal end 2122, and a radially inwardly-extending lip 2123 at the distal end 2124 of the outer housing sleeve 212. The staple and blade portion 106 also includes a staple cartridge 214. The staple cartridge 214 defines a plurality of axially-disposed staple receiving slots 2141 in which staples 2142 are stored. In the embodiment shown in FIG. 10(b), the staple receiving slots 2141 are disposed circumferentially around the staple cartridge 214 in two radially-spaced apart rows, wherein the staple receiving slots 2141 in the first row overlap the staple receiving slots 2141 in the second row. The staple cartridge 214 also includes a radially inwardly-extending lip 2145 located near the distal end 2147 of the staple cartridge 214 and a radially outwardly-extending lip 2143 located near the proximal end 2144 of the staple cartridge 214. Furthermore, the distal end 2147 of the staple cartridge 214 defines a clamping face 2146.

The staple and blade portion 106 also includes a frangible blade protection ring 216 that defines within its interior a slot 2161. In addition, the staple and blade portion 106 includes a blade 218. The blade 218 has a cutting edge 2183 that extends circumferentially along its distal end 2184. In addition, the blade 218 defines a radially, inwardly-extending tab or lip 2181 at its proximal end 2182.

The staple and blade portion 106 also includes a staple pusher 220. The staple pusher 220 has a plurality of axially-disposed pushing teeth 2201, each of which corresponds to and aligns with the staple receiving slots 2141 of the stapler cartridge 214. The staple pusher 220 also includes a key 2202 on its outer surface.

The staple and blade portion 106 also includes a staple pusher carriage element 222 that has a neck portion 2221 and a flange portion 2222, the neck portion 2221 extending axially in a distal direction relative to the flange portion 2222. An interior surface of the neck portion 2221 includes threads 2223, while an exterior surface of the neck portion 2221 defines a circumferentially-disposed recess 2224. In addition, the radially outermost edge of the flange 2222 includes a key 2225.

Figure 10C:
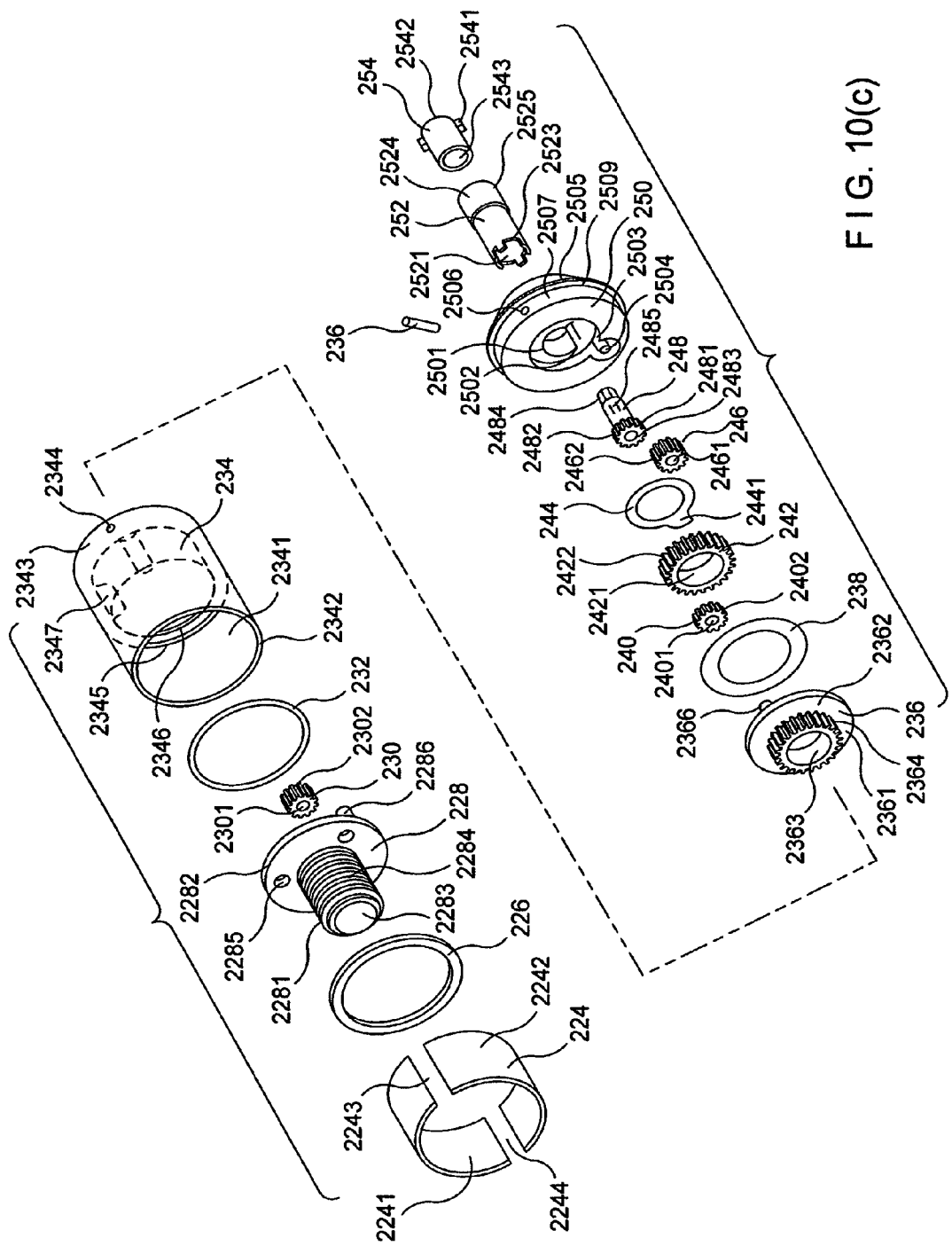
FIG. 10(c) is a perspective view that illustrates the remaining components of the staple and blade portion in an exploded condition, according to one embodiment of the present invention.

FIG. 10(c) is a perspective view that illustrates the remaining components of the staple and blade portion 106 in an exploded condition, according to one embodiment of the present invention. As shown in FIG. 10(c), the staple and blade portion 106 also includes a split ring 224. The split ring 224 includes a pair of semi-circular ring portions 2241 and 2242 that when arranged in the shape of a ring define therebetween a pair of keyways 2243 and 2244. The staple and blade portion 106 also includes a washer 226. The staple and blade portion 106 also includes a thrust element 228 that has a neck portion 2281 and a flange portion 2282, the neck portion 2281 extending axially in a distal direction relative to the flange portion 2282. A bore 2283 is defined within the interior of the neck portion 2281, while an exterior surface of the neck portion 2281 defines threads 2284 that correspond to the threads 2223 located on the interior surface of the neck portion 2221 of the staple pusher carriage element 222. The flange 2282 of the thrust element 228 includes one or more bores 2285 within its distally-facing surface, and a proximally-extending pin 2286 having, e.g., a round cross section.

The staple and blade portion 106 also includes a first spur gear 230. The first spur gear 230 defines an internal bore 2301 that corresponds cross-sectionally to the pin 2286 of the thrust element 228. The first spur gear 230 also includes circumferentially-disposed spur gear teeth 2302. The staple and blade portion 106 also includes a washer 232, and an inner housing sleeve 234. The inner housing sleeve 234 includes an internal bore 2341 that has a first interior radius at a distal end 2342 of the inner housing sleeve 234. The internal bore 2341 extends proximally towards a radially inwardly-extending lip 2345 at which point the interior radius of the internal bore 2342 is reduced. The internal bore 2342 extends still further proximally to a second radially inwardly-extending lip 2346 at which point the interior radius of the internal bore 2342 is again reduced. Proximal to the second lip 2346 are gear teeth 2347 that extend circumferentially along the interior surface of the inner housing sleeve 234. A proximal end 2343, e.g., proximal relative to the gear teeth 2347, has a smooth interior surface, and has one or more radial openings 2344 defined therein.

The staple and blade portion 106 also includes a sun gear element 236 that has a neck portion 2361 and a flange portion 2362, the neck portion 2361 extending axially in a distal direction relative to the flange portion 2362. A bore 2363 is defined within the interior of the neck portion 2361, while an exterior surface of the neck portion 2361 has circumferentially-disposed gear teeth 2364 that correspond to the gear teeth 2302 of the first spur gear 230. The flange portion 2362 includes a proximally-extending pin 2366 having, e.g., a round cross section. The staple and blade portion 106 also includes a washer 238.

The staple and blade portion 106 also includes a first planetary gear 240 having an internal bore 2401. An exterior surface of the first planetary gear 240 has circumferentially-disposed gear teeth 2402. The staple and blade portion 106 also includes a sun gear 242 having an internal bore 2421. An exterior surface of the sun gear 242 has circumferentially-disposed gear teeth 2422 that correspond to the gear teeth 2402 of the first planetary gear 240. The staple and blade portion 106 also includes a washer 244 having a tab 2441. The staple and blade portion 106 also includes a second planetary gear 246 having an internal bore 2461. An exterior surface of the second planetary gear 246 has circumferentially-disposed gear teeth 2462 that correspond to circumferentially-disposed gear teeth 2422 of the sun gear 242.

The staple and blade portion 106 also includes an input element 248. A distal end 2481 of the input element 248 has an internal bore 2483, which may have, e.g., a square cross-section. On an outer surface of the distal end 2481 of the input element 248 are circumferentially-disposed gear teeth 2482 that correspond to the circumferentially-disposed gear teeth 2462 on the exterior surface of the second planetary gear 246. A proximal end 2484 of the input element 248 has a round outer circumference and an internal bore 2485.

The staple and blade portion 106 also includes a housing rear endcap 250 having a central bore 2501, a second bore 2502 radially offset relative to the central bore 2501, and a recess 2503 from which a pin 2504 extends in a distal direction. The housing rear endcap 250 also includes an outer radial lip 2505. Located distally relative to the outer radial lip 2505 is at least one opening 2506 defined within a round outer circumferential surface 2507. The housing rear endcap 250 also includes at its proximal end one or more keyways 2509 in communication with the central bore 2501.

The staple and blade portion 106 also includes a central rear endcap sleeve 252 having a bore 2521 disposed therethrough. At a distal end 2522 of the central rear endcap sleeve 252, the bore 2521 defines a radially inwardly-extending rim 2523. At a proximal end 2524 of the central rear endcap sleeve 252 are oppositely-disposed keyways 2525.

The staple and blade portion 106 also includes a retainer sleeve 254 having a bore 2541 disposed therethrough. At a proximal end 2542 of the retainer sleeve 254 are oppositely-disposed keys 2543 that correspond to the oppositely-disposed keyways 2525 located at the proximal end 2524 of the central rear endcap sleeve 252 and the keyways 2509 of the rear housing endcap 250.

Figure 11A:
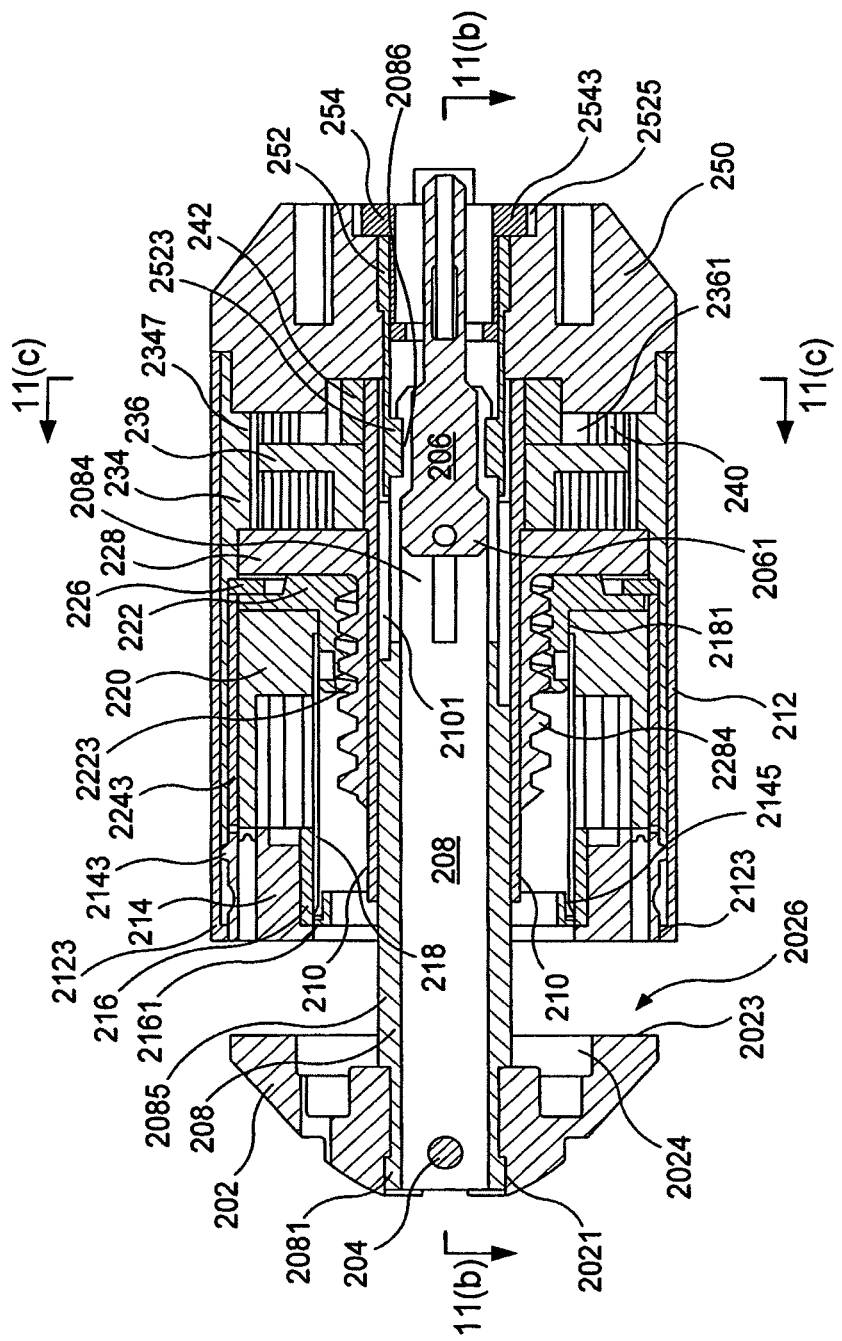
FIG. 11(a) is a top, cross-sectional view that illustrates the cutting and stapling component, according to one embodiment of the present invention.

FIG. 11(a) is a top, cross-sectional view and FIG. 11(b) is a side, cross-sectional view that illustrate the cutting and stapling component 103, according to one embodiment of the present invention. FIGS. 11(a) and 11(b) show the cutting and stapling component 103 in an assembled and partially retracted position, as set forth more fully below. As shown in FIGS. 11(a) and 11(b), the distal end 2081 of the anvil sleeve 208 is inserted into the corresponding, centrally-disposed opening 2021 in the anvil end cap 202. The anvil pin 204 is inserted through the radially-disposed slot 2022 of the end cap 202 and through the oppositely-disposed openings 2082 in the distal end 2081 of the anvil sleeve 208 so that the anvil end cap 202 is axially and rotatably fixed relative to the anvil sleeve 208. The distal end 2061 of the anvil extension rod 206 is axially retained within the recess 2086 at the proximal end 2084 of the anvil sleeve 208. The anvil sleeve 208 is axially and slidably retained within the interior of the anvil sleeve guide 210. The anvil sleeve 208 is prevented from rotating relative to the anvil sleeve guide 210 by the engagement of the keys 2085 of the anvil sleeve 208 within the keyways 2101 of the anvil sleeve guide 210.

Extending through the central opening 2501 of the housing rear end 250 and into the proximal end 2103 of the anvil sleeve guide 210 is the central rear endcap sleeve 252. In the position shown, the rim 2523 of the central rear endcap sleeve 252 is engaged within the recess 2086 of the anvil sleeve 208, thereby axially fixing the central rear endcap sleeve 252 and the anvil sleeve 208 relative to each other. Inserted into the bore 2521 of the central rear endcap sleeve 252 is the retainer sleeve 254. The keys 2543 of the retainer sleeve 254 engage the keyways 2525 of the central rear endcap sleeve 252 and the keyways 2509 of the housing rear endcap 250 so as to prevent relative rotation between the retainer sleeve 254, the central rear endcap sleeve 252 and the housing rear endcap 250.

The input element 248 is rotatably maintained within the second opening 2502 of the housing rear end cap 250. The teeth 2482 of the input element 248 are in meshing engagement with the circumferentially-disposed teeth 2462 of the second planetary gear 246, which is rotatably mounted on the pin 2504 extending distally from the recess 2503 of the housing rear endcap 250. The circumferentially-disposed teeth 2462 of the second planetary gear 246 are also in meshing engagement with circumferentially-disposed teeth 2422 of the sun gear 242. The sun gear 242 is rotatably mounted via its internal bore 2421 on the proximal end 2103 of the anvil sleeve guide 210.

The circumferentially-disposed teeth 2422 of the sun gear 242 are also in meshing engagement with the circumferentially-disposed teeth 2402 of the first planetary gear 240. The first planetary gear 240 is rotatably mounted on the pin 2361 that extends proximally from the flange portion 2362 of the sun gear element 236. The circumferentially-disposed teeth 2402 of the first planetary gear 240 are also in meshing engagement with the gear teeth 2347 that extend circumferentially around the interior surface of the inner housing sleeve 234. The inner housing sleeve 234 is rotatably and axially fixed relative to the housing rear endcap 250 and the outer housing sleeve 212 by the insertion of fasteners 256, e.g., pins or screws, through aligned openings 2121, 2344 and 2506 in the outer housing sleeve 212, the inner housing sleeve 234 and the housing rear endcap 250, respectively.

The sun gear element 236 is rotatably mounted via its internal bore 2363 on the anvil sleeve guide 210. The circumferentially-disposed gear teeth 2364 on the exterior surface of the neck portion 2361 of the sun gear element 236 are in meshing engagement with the circumferentially-disposed gear teeth 2302 of the first spur gear 230. The first spur gear 230 is rotatably mounted on the thrust element 228 by the internal bore 2301 of the first spur gear 230 having inserted therein the proximally-extending pin 2286 of the thrust element 228. The circumferentially-disposed gear teeth 2302 of the first spur gear 230 are also in meshing engagement with the gear teeth 2347 that extend circumferentially around the interior surface of the inner housing sleeve 234.

The thrust element 228 is rotatably mounted on the anvil sleeve guide 210 by the anvil sleeve guide 210 fitting within the internal bore 2283 of the thrust element 228. The washer 232 resides between the proximal surface of the flange 2282 of the thrust element 282 and the second lip 2346 of the inner housing sleeve 234, while the washer 226 resides between the distal surface of the flange 2282 of the thrust element 282 and the flange 2222 of the staple cartridge carrier element 222.

The staple pusher carriage element 222 is mounted on the thrust element 228 such that the threads 2223 located on the interior surface of the neck portion 2221 of the staple pusher carriage element 222 are in threaded engagement with the threads 2284 located on the exterior surface of the neck portion 2281 of the thrust element 228. The keys 2225 of the staple pusher carriage element 222 are engaged within the keyways 2243 formed by the split ring 224, thereby enabling the staple pusher carriage element 222 to be axially slidable relative to the split ring 224. The split ring is positioned within the bore 2341 at the distal end 2342 of the inner housing sleeve 234.

Located within the split ring 224, and abutting the flange 2282 of the thrust element 228 is the staple pusher 220. The keys 2202 of the staple pusher 220 are engaged within the keyways 2243 formed by the split ring 224, thereby enabling the staple pusher 220 to be axially slidable relative to the split ring 224. The pushing teeth 2201 of the staple pusher 220 extend distally and align with the staple receiving slots 2141 of the staple cartridge 214.

The staple cartridge 214 is positioned distally relative to the staple pusher 220 and is maintained within the interior of the outer housing sleeve 212. The staple cartridge 214 is axially moveable in a distal direction within the outer housing sleeve 212 from the position shown in FIGS. 11(a) and 11(b) until the radially, outwardly-extending lip 2143 of the staple cartridge 214 abuts the radially, inwardly-extending lip 2123 of the outer housing sleeve 212 as set forth more fully below.

Located between the staple pusher 220 and the staple pusher carriage element 222 is the blade 218. The radially, inwardly-extending tab or lip 2185 located at the distal end 2182 of the blade is engaged within the recess 2224 located on the outer surface of the neck portion 2221 of the staple pusher carriage element 222. The cutting edge 2183 of the blade 218 is sheathed within the slot 2161 of the frangible blade protection ring 216. The frangible blade protection ring 216 axially abuts the radially inwardly-extending lip 2144 of the staple cartridge 214.

In operation, the surgical attachment 100 is attached via the quick connect coupling 304 of the handle portion 102 to the flexible shaft 20 such that the first rotatable drive shaft 30 of the flexible shaft 20 is coupled, e.g., non-rotatably, to the first input element 306a of the handle portion 102 and such that the second rotatable drive shaft 32 of the flexible shaft 20 is coupled, e.g., non-rotatably, to the second input element 306b of the handle portion 102. Initially, the trocar shaft 108 of the surgical attachment 100 may be in a retracted position, such as illustrated in FIG. 9, so as to facilitate the insertion of the surgical attachment 100 into the body of a patient. For instance, in this position, the staple and blade portion 106 may be inserted into an oral passage of the patient. The controller 1122 may initially be configured to operate in a clamping mode. In the clamping mode, rotation of the first rotatable drive shaft 30 in a first direction, e.g., clockwise when viewed from the proximal end, causes rotation of the input element 306a in the first direction. By the meshing engagement of the gear teeth 3063 of the first input element 306 a with the spur gear teeth 3101 of the spur gear 310, the spur gear 310 is caused to rotate in a second direction, e.g., counter-clockwise when viewed from the proximal end. Rotation of the spur gear 310 in the second direction causes the rod 312, the threads of which are engaged within the threaded internal bore 3102 of the spur gear 310, to move axially within the housing portion 102. The coupling element 314 at the end of the rod 312 is engaged, e.g., non-rotatably, with the first drive shaft 104a of the flexible shaft 104, which in turn is engaged, e.g., non-rotatably, with the trocar shaft 108 extending through the staple and blade portion 106 of the cutting and stapling component 103. In this manner, the trocar shaft 108, having the trocar 110 disposed at its end, may be extended by movement in a first, e.g., distal, direction to a desired distance relative to the staple and blade portion 106. The trocar 110 is pushed through a section of tissue desired to be stapled and is inserted within the trocar receiving slot 2065 of the anvil extension rod 206 so as to be axially fixed relative to the anvil extension rod 206. The trocar shaft 108 is then retracted by operation of the first rotatable drive shaft 30 in the opposite direction so as to draw the anvil extension rod 206, and the other components of the anvil assembly 112, into the anvil sleeve guide 210.

As the trocar shaft 108 is further retracted by continued rotation of the first rotatable drive shaft 30 in, e.g., the second direction, the keys 2085 of the anvil sleeve 208 engage with the keyways 2101 within the anvil sleeve guide 210 to thereby align the anvil assembly 112 with the staple and blade portion 106. Still further retraction of the trocar shaft 108 causes the anvil sleeve 108 to move proximally within the anvil sleeve guide 210 until the rim 2523 of the central rear endcap sleeve 252 seats within the recess 2086 of the anvil sleeve 208. When the rim 2523 of the central rear endcap sleeve 252 seats within the recess 2086 of the anvil sleeve 208, the anvil assembly 112 is axially locked in position relative to the staple and blade portion 106. According to one embodiment of the present invention, the anvil assembly 112 is axially locked in position relative to the staple and blade portion 106 when the clamping face 2023 of the anvil end cap 202 is at a distance of approximately 5 mm from the clamping face 2146 of the staple cartridge 214.

Once the anvil assembly 112 is axially locked in position relative to the staple and blade portion 106, the controller 1122 may cease rotation of the first rotatable drive shaft 30 in the second direction. The controller 1122 may then change to a firing mode of operation. In the firing mode of operation, the second rotatable drive shaft 32 may be rotated in a first, e.g., clockwise, direction, which in turn rotates the input element 306 b in the first direction. By the meshing engagement of the gear teeth 3066 of the input element 306 b with the spur gear teeth 3181 of the spur gear 318, the spur gear 318 is caused to rotate in a second, e.g., counter-clockwise, direction. Rotation of the spur gear 318 in the second direction causes the shaft drive element 316, and the second drive shaft 104b of the flexible shaft 104 which is non-rotatably connected to the shaft drive element 316, to rotate in the second direction. Rotation of the second drive shaft 104b of the flexible shaft 104 thereby causes the input element 248 of the staple and blade portion 106 to which it is non-rotatably coupled to also rotate in the second direction. Thus, the input element 248 rotates within the second opening 2502 of the housing rear end cap 250. By the meshing engagement of the teeth 2482 of the input element 248 with the circumferentially-disposed teeth 2462 of the second planetary gear 246, rotation of the input element 248 in the second direction causes rotation of the second planetary gear 246 on the pin 2504 in the first direction. Additionally, by the meshing engagement of the circumferentially-disposed teeth 2462 of the second planetary gear 246 with circumferentially-disposed teeth 2422 of the sun gear 242, rotation of the second planetary gear 246 in the first direction causes rotation of the sun gear 242 around the proximal end 2103 of the anvil sleeve guide 210 in the second direction.

By the meshing engagement of the circumferentially-disposed teeth 2422 of the sun gear 242 with the circumferentially-disposed teeth 2402 of the first planetary gear 240, rotation of the sun gear 242 around the proximal end 2103 of the anvil sleeve guide 210 in the second direction causes rotation of the first planetary gear 240 on the pin 2361 extending proximally from the flange portion 2362 of the sun gear element 236 in the first direction. By the meshing engagement of the circumferentially-disposed teeth 2402 of the first planetary gear 240 with the gear teeth 2347 of the inner housing sleeve 234, and since the inner housing sleeve 234 is rotatably fixed within the staple and blade portion 106, rotation of the first planetary gear 240 in the first direction causes the first planetary gear 240 to revolve within the inner housing sleeve 234 in the second direction. Since the first planetary gear 240 is mounted on the pin 2361 extending proximally from the flange portion 2362 of the sun gear element 236, the revolving motion of the first planetary gear 240 in the second direction causes the sun gear element 236 to rotate around the anvil sleeve guide 210 in the second direction.

By the meshing engagement of the gear teeth 2364 on the exterior surface of the neck portion 2361 of the sun gear element 236 and the gear teeth 2302 of the first spur gear 230, rotation of the sun gear 236 in the second direction causes the first spur gear 230 to rotate in the first direction. By the meshing engagement of the circumferentially-disposed gear teeth 2302 of the first spur gear 230 with the gear teeth 2347 of the inner housing sleeve 234, and since the inner housing sleeve 234 is rotatably fixed within the staple and blade portion 106, rotation of the first spur gear 230 in the first direction causes the first spur gear 230 to revolve in the second direction within the inner housing sleeve 234. Furthermore, since the first spur gear 230 is mounted on the pin 2286 extending proximally from the flange portion 2282 of the thrust element 228, the revolving motion of the first spur gear 230 in the second direction causes the thrust element 228 to rotate in the second direction around the anvil sleeve guide 210.

The rotation of the thrust element 228 in the second direction around the anvil sleeve guide 210 causes the staple pusher carriage element 222, by virtue of the threads 2284 located on the exterior surface of the neck portion 2281 of the thrust element 228 being in threaded engagement with the threads 2223 located on the interior surface of the neck portion 2221 of the staple pusher carriage element 222, to move relative to the thrust element 228. Because the keys 2225 of the staple pusher carriage element 222 are engaged within the keyways 2243 formed by the split ring 224, the staple pusher carriage element 222 is caused to axially slide within the split ring 224 in the distal direction. The distal movement of the staple pusher carriage element 222 causes the staple pusher 220, by virtue of the abutment of the flange 2282 of the thrust element 228 with the staple pusher 220, to also move in the distal direction.

Movement of the staple pusher 220 in the distal direction causes the blade 218 to move along with the staple pusher 220 in the distal direction. The cutting edge 2183 of the blade 218, which is sheathed within the slot 2161 of the frangible blade protection ring 216, causes the frangible blade protection ring 216 to be moved distally. Since the frangible blade protection ring 216 axially abuts the inward lip 2144 of the staple cartridge 214, the distal movement of the frangible blade protection ring 216 also causes distal movement of the staple cartridge 214. Thus, at this stage of operation, the staple pusher 220, the blade 218, the frangible blade protection ring 216 and the staple cartridge 214 move distally together. The staple cartridge 214 moves distally so as to further clamp a section of tissue (not shown) between the clamping face 2023 of the anvil endcap 202 and the clamping face 2146 of the staple cartridge 214. Depending on the thickness of the section of tissue, the staple cartridge 214 may move distally until the lip 2143 of the staple cartridge 214 abuts the radially, inwardly-extending lip 2123 of the outer housing sleeve 212.

Once the staple cartridge 214 has been moved distally sufficiently to completely clamp a section of tissue, continued rotation of the second rotatable drive shaft 32 causes further distal movement of the staple pusher 220, the frangible blade protection ring 216 and the blade 218. Once the frangible blade protection ring 216 and the staple cartridge 214 are prevented from further distal movement by contact with a compressed section of tissue, the staple pusher 220 and the blade 218 are caused to continue to move distally relative these components. Specifically, further distal movement of the blade 218 causes the cutting edge 2183 of the blade 218 to penetrate the frangible blade protection ring 216 and to thereby cut the section of tissue that has been clamped. Advantageously, these components are configured such that approximately 70 lbs. or more of pressure is employed to cause the cutting edge 2183 of the blade 218 to penetrate the frangible blade protection ring 216 and to thereby cut the section of tissue, thereby ensuring that the section of tissue is sufficiently clamped prior to cutting. Simultaneously, further distal movement of the staple pusher 220 causes the pushing teeth 2201 of the staple pusher 220, which are aligned with the staple receiving slots 2141 of the stapler cartridge 214, to begin moving distally through the staple receiving slots 2141. The staples 2142 that are maintained within the staple receiving slots 2141 of the stapler cartridge 214 are thereby pushed through the section of clamped tissue and into the staple guides 2026 of the clamping face 2023 of the anvil endcap 202 until the staples 2142 are closed.

Upon the staples 2142 being fully closed, the clamping force on the section of tissue may be reduced by rotation of the second drive shaft 32 in the opposite direction. Generally, when the second drive shaft 32 is rotated in the opposite direction, the thrust element 228 is caused, via the reverse movement of the components of the staple and blade portion 106, to also rotate in a direction opposite of that described above, thereby causing the staple pusher carriage element 222 to be retracted, e.g., moved proximally. The blade 218 is also caused to be retracted, e.g., moved proximally, by the lip 2181 of the blade 218 being engaged within the recess 2224 located on the outer surface of the neck portion 2221 of the staple pusher carriage element 222. Once the clamping force between the clamping face 2023 of the anvil endcap 202 and the clamping face 2146 of the staple cartridge 214 has been sufficiently reduced, the section of tissue that has been cut and stapled is removed from between the clamping face 2023 of the anvil endcap 202 and the clamping face 2146 of the staple cartridge 214, and the surgical attachment 100 may be removed from within the patient.

Figure 12A:
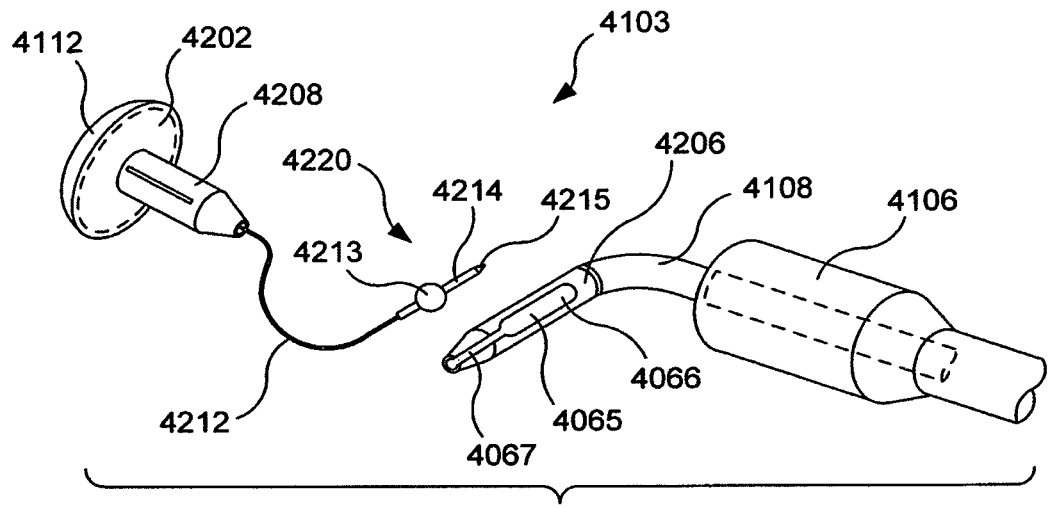
FIG. 12(a) is a perspective view of a cutting and stapling component, according to one embodiment of the present invention.
Figure 12B:
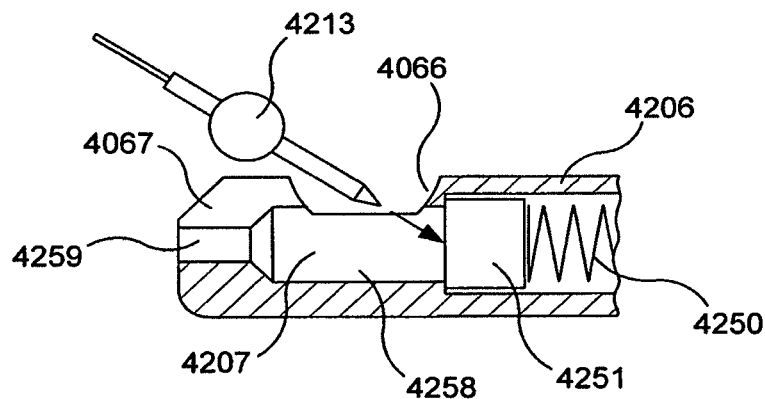
FIGS. 12(b) and 12(c) are side cross-sectional views that illustrate additional features of a cable extension element, according to one embodiment of the present invention.
Figure 12C:
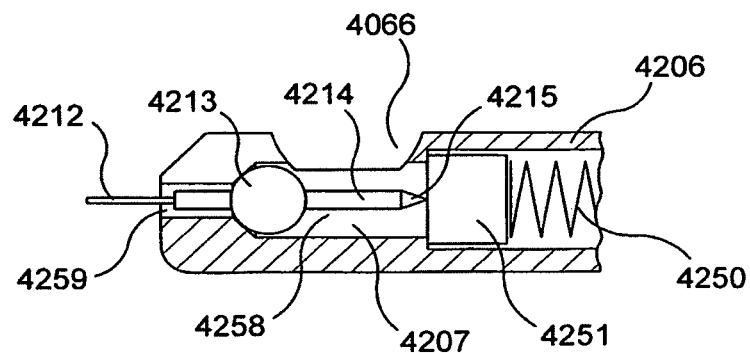

FIGS. 12(a) to 12(c) illustrate some components of a cutting and stapling component, according to another embodiment of the present invention. Specifically, FIG. 12(a) is a perspective view of a cutting and stapling component 4103 that includes an staple and blade portion 4106. Extending in an axial direction through a centrally disposed opening of the staple and blade portion 4106 is a flexible trocar shaft 4108, e.g., a cable. Disposed at a distal end 4108a of the flexible trocar shaft 4108 is a cable extension element 4206 that defines a trocar receiving slot 4065. The trocar receiving slot 4065 has a wide portion 4066 at its proximal end and a narrow portion 4067 at its distal end.

The cutting and stapling component 4103 also includes an anvil assembly 4112. The anvil assembly 4112 includes an anvil end cap 4202. The anvil end cap 4202 has extending proximally therefrom an anvil sleeve 4208. Extending from a proximal-most end of the anvil sleeve 4208 is a flexible cable 4212 having a trocar 4220 attached thereto. The trocar 4220 includes a first portion 4213, e.g., a spherical orb, from which extends a cylindrical finger 4214. The cylindrical finger 4214 tapers to a trocar tip 4215.

FIG. 12(*b*) is a side cross-sectional view that illustrates additional features of the cable extension element 4206. Specifically, the cable extension element 4206 defines an axially-extending central bore 4207 with which the narrow portion 4067 and the wide portion 4066 of the trocar receiving slot 4065 are in communication. Positioned within the central bore 4207 and proximal to the trocar receiving slot 4065 is a plunger 4251 that is biased in the distal direction by a biasing element, e.g., spring, 4250. As shown in FIG. 12(*b*), the trocar tip 4215 is configured to be pushed against and displace the biased plunger 4251 such that the first portion 4213, e.g., the spherical orb, of the trocar 4220 is positioned proximal to the narrow portion 4067 of the trocar receiving slot 4065.

As shown in FIG. 12(*c*), once the first portion 4213, e.g., the spherical orb, of the trocar 4220 is positioned proximal to the narrow portion 4067 of the trocar receiving slot 4065, the trocar 4220 is lowered through the trocar receiving slot 4065 and into the central bore 4207. The plunger 4251 is then biased by the bias element 4250 in the distal direction so as to seat the first portion 4213 of the trocar 4220 at the interface of the wide portion 4258 and the narrow portion 4259 of the central bore 4207. The narrow portion 4259 of the central bore 4207 retains the trocar 4220 so that, when the trocar shaft 4108 is retracted relative to the staple and blade portion 4106, the anvil assembly 4112 is also retracted.

This embodiment of the cutting and stapling component 4103 provides for an arrangement that facilitates the connection of the trocar shaft 4108 to the anvil assembly 4112. Specifically, the flexible cable 4212 of the anvil assembly 4112 and the flexible trocar shaft 4108 enable the anvil assembly 4112 to be more easily connected to the flexible trocar shaft 4108. For instance, this arrangement may enable the anvil assembly 4112 to be connected to the flexible trocar shaft 4108 without requiring that the anvil assembly 4112 be aligned with the flexible trocar shaft 4108 prior to such connection and/or with requiring that the tissue limbs in which the anvil assembly 4112 and the flexible trocar shaft 4108 are positioned be aligned prior to such connection. Furthermore, this arrangement supports high tensile loads, thus enabling the section of tissue that is cut and stapled to be clamped with a greater clamping force than may be possible in conventional surgical devices. It should be recognized that, while the embodiment shown in FIGS. 12(*a*) to 12(*c*) has the trocar 4220 attached to the anvil assembly 4112 and the cable extension element 4206 attached to the trocar shaft 4108, in another embodiment, the trocar 4220 may be attached to the trocar shaft 4108 and the cable extension element 4206 may be attached to the anvil assembly 4112.

Figure 13C:
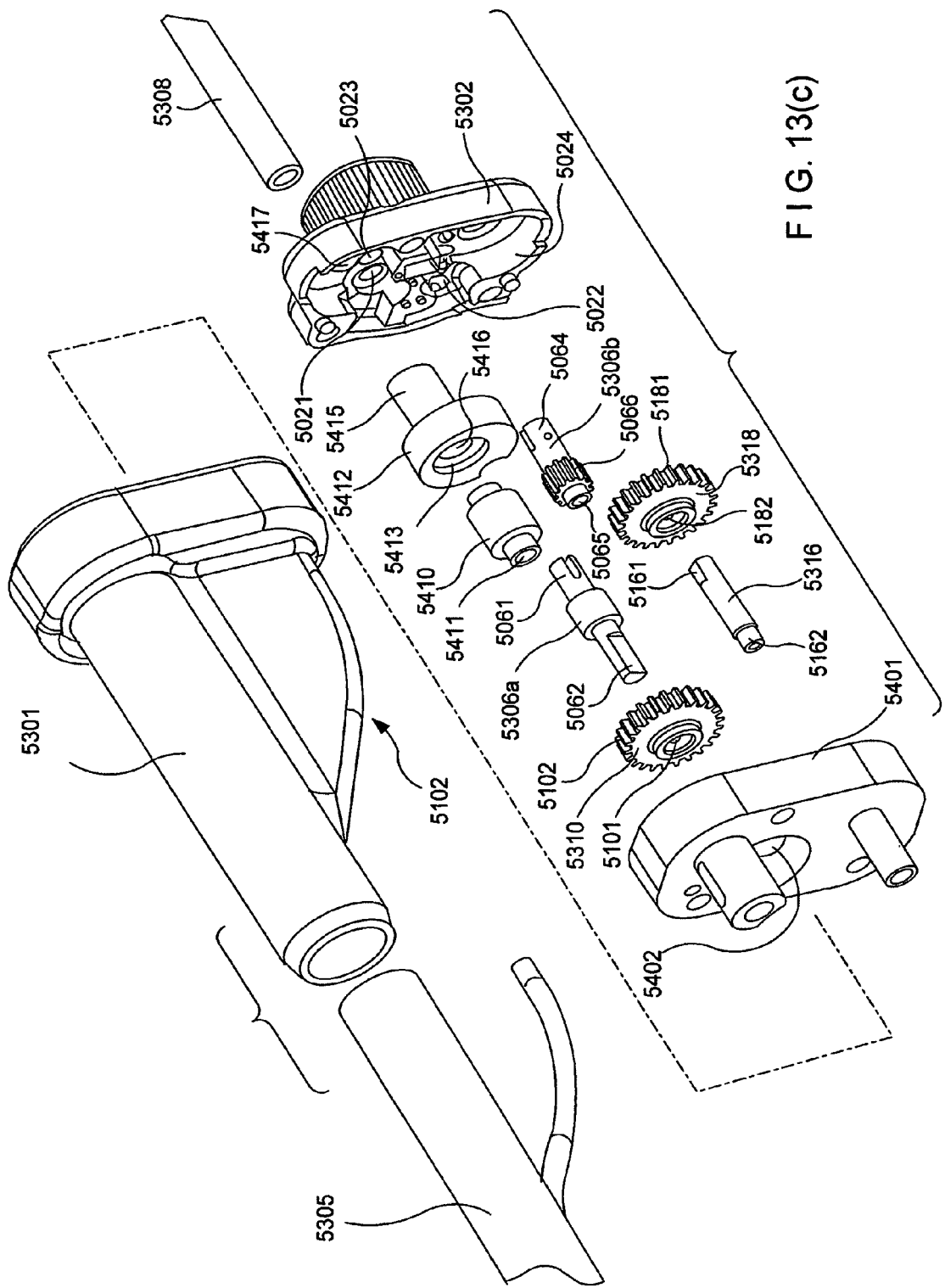

FIGS. 13(*a*) to 13(*c*) illustrate a handle portion, according to another embodiment of the present invention. Specifically, FIG. 13(*a*) is a front perspective view, and FIG. 13(*b*) is a rear perspective view, of a handle portion 5102 including a housing 5301. At a proximal end 5301*a* of the housing 5301 is disposed a gear housing 5302. At a distal end 5301 *b* of the housing 5301 there extends an insertion tube 5305. Extending from the gear housing 5302 is a quick connect coupling 5304 and a tube 5308.

The quick-connect coupling 5304 is mounted onto the gear housing 5302 and may be biased, e.g., via a set of springs. The gear housing 5302 includes a first drive socket 5304*a* and a second drive socket 5304*b*. FIG. 13(*c*) is an exploded front perspective view of the handle portion 5102. As shown in FIG. 13(*c*), the gear housing 5302 mates with a gear retaining plate 5401 so as to maintain the remaining gear components in relative position. The first drive socket 5304*a* includes a first input element 5306*a*, one end 5061 of which extends through an opening 5021 of the gear housing 5302. A first spur gear 5310 has an internal bore 5101 and circumferentially-disposed spur gear teeth 5102. A second end 5062 of the first input element 5306*a* extends, e.g., non-rotatably, through the internal bore 5101 of the first spur gear 5310. The teeth 5102 of the first spur gear 5310 engage a gear nut 5410 having an internally threaded axially-extending bore 5411 into which the first drive shaft 104*a* of the flexible shaft 104 may be inserted by threaded engagement. The gear nut 5410 seats within a recess 5413 of a gear bearing 5412. The gear bearing 5412 seats within a recess 5023 of the gear housing 5302. A neck portion 5415 of the gear bearing 5412 has an internal bore 5416 and extends proximally through an opening 5417 of the gear housing 5302.

The second drive socket 5304 *b* includes a second input element 5306 *b*, one end 5064 of which extends through a second opening 5022 of the gear housing 5302 and the other end 5065 of which includes spur gear teeth 5066. Also seated within an internal recess 5024 of the gear housing 5302 is a spur gear 5318. The spur gear 5318 has arranged along its outer radius spur gear teeth 5181 that correspond to the spur gear teeth 5066 of the second input element 5306*b*. The spur gear 5318 has a bore 5182 extending therethrough. Non-rotatably engaged within the bore 5182 of the spur gear 5318 is a first end 5161 of a shaft drive element 5316. A second end 5162 of the shaft drive element 5316 is configured to non-rotatably engage the second drive shaft 104*b* of the flexible shaft 104, which extends through the insertion tube 5305 and to the second end 5162 of the shaft drive element 5316.

In operation, the handle portion 5102 is attached via the quick connect coupling 5304 to the flexible shaft 20 such that the first rotatable drive shaft 30 of the flexible shaft 20 is coupled, e.g., non-rotatably, to the first input element 5306*a* of the handle portion 5102 and such that the second rotatable drive shaft 32 of the flexible shaft 20 is coupled, e.g., non-rotatably, to the second input element 5306*b* of the handle portion 5102. In the clamping mode, rotation of the first rotatable drive shaft 30 in a first, e.g., clockwise, direction rotates the input element 5306*a* in the first direction. By the meshing engagement of the gear teeth 5063 of the first input element 5306*a* with the spur gear teeth 5101 of the spur gear 5310, the spur gear 5310 is caused to rotate in a second, e.g., counter-clockwise, direction. Rotation of the spur gear 5310 in the second direction causes rotation of the gear nut 5410 in the first direction. By the threaded engagement of the first drive shaft 104*a* of the flexible shaft 104 with the internal bore 5101 of the spur gear 5310, the first drive shaft 104*a* of the flexible shaft 104, and thus the trocar shaft 108 to which the first drive shaft 104*a* is attached, is caused to move axially. In this manner, the trocar shaft 108 may be extended in a first, e.g., distal, direction to a desired distance relative to the staple and blade portion 106. Once the trocar 110 is inserted within the trocar receiving slot 2065 of the anvil extension rod 206, the trocar shaft 108 may then be retracted by operation of the first rotatable drive shaft 30 in the opposite direction.

In the firing mode of operation, the second rotatable drive shaft 32 may be rotated in a first, e.g., clockwise, direction, so as to rotate the input element 5306b in the first direction. By the meshing engagement of the gear teeth 5066 of the input element 5306b with the spur gear teeth 5181 of the spur gear 5318, the spur gear 5318 is caused to rotate in a second, e.g., counter-clockwise, direction. Rotation of the spur gear 5318 in the second direction causes the shaft drive element 5316, and the second drive shaft 104b of the flexible shaft 104 which is non-rotatably connected to the shaft drive element 316, to rotate in the second direction. Rotation of the second drive shaft 104b of the flexible shaft 104 thereby causes the input element 248 of the staple and blade portion 106 to which it is non-rotatably coupled to also rotate in the second direction. In this manner, the staple cartridge 214 of the staple and blade portion 106 may be moved relative to the anvil assembly 112 so as to clamp a section of tissue disposed therebetween, and the tissue may be cut and stapled as set forth more fully above.

Figure 14D:
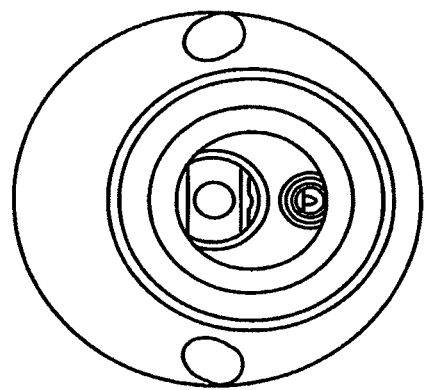
FIG. 14(d) is a rear view that illustrates the cutting and stapling component shown in FIG. 14(a), in an assembled and partially closed position.
Figure 14C:
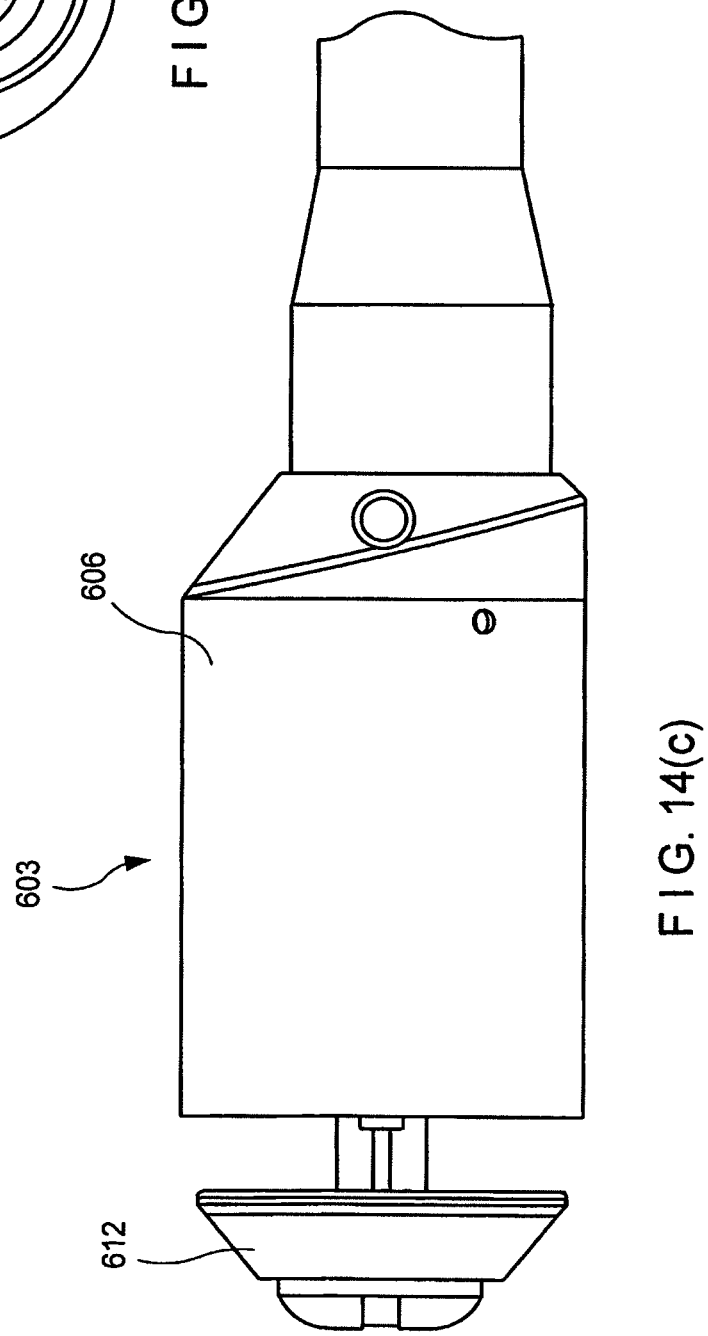
FIG. 14(c) is a side view that illustrates the cutting and stapling component shown in FIG. 14(a), in an assembled and partially closed position.

FIGS. 14(a) to 14(d) and FIGS. 15(a) to 15(d) illustrate a cutting and stapling component according to another embodiment of the invention. Specifically, FIG. 14(a) is a front perspective view and FIG. 14(b) is a rear perspective view that illustrate a cutting and stapling component 603 in an assembled and partially closed position. FIG. 14(c) is a side view and FIG. 14(d) is a rear view that illustrate the cutting and stapling component 603 in the same position and condition. As shown, the cutting and stapling component 603 includes an anvil assembly 612 and a staple and blade portion 606.

FIG. 15(a) is a front exploded view that illustrates the components of the anvil assembly 612. The anvil assembly 612 includes an anvil end cap 602. The anvil end cap 602 has a centrally-disposed opening 6021 arranged in the axial direction. The anvil end cap 602 also includes a radially-disposed slot 6022 on a distal side 6025 of the end cap 602, and a clamping face 6023 on a proximal side 6026 of the anvil end cap 602. The clamping face 6023 has recessed portion that forms a blade repository 6024, the purpose of which is set forth in additional detail below. The clamping face 6023 also defines staple guides 6027.

The anvil assembly 612 also includes a pin 604 corresponding cross-sectionally to the slot 6022 of the anvil end cap 602. The anvil assembly 612 also includes a hollow anvil sleeve 608. A distal end 6083 of the anvil sleeve 608 corresponds cross-sectionally to the opening 6021 of the anvil end cap 602. In addition, the distal end 6083 of the anvil sleeve 608 defines openings 6082 that correspond cross-sectionally to the anvil pin 604. In a proximal end 6084 of the anvil sleeve 608 there is defined a recess 6086 that extends circumferentially around the anvil sleeve 608 and that has a radius that is smaller than the radius of the other portions of the anvil sleeve 608, including the radius of several radially-disposed teeth 6087 located at the proximal-most end of the anvil sleeve 608. The proximal end 6084 of the anvil sleeve 608 also defines a plurality, e.g., four, axial slots 6088 that extend through the recess 6086 and the teeth 6087, thereby enabling the proximal end 6084 of the anvil sleeve 608 to be radially compressed. The anvil sleeve 608 also includes one or more axially-disposed keys 6085 on its outer surface.

The anvil assembly 612 also includes an anvil extension rod 606. The anvil extension rod 606 has a distal end 6061 that may be flat and that defines an opening 6062. The anvil extension rod 606 also has a central region 6063 that is round and that corresponds cross-sectionally to an inner diameter of the recess 6086 of the anvil sleeve 608. The distal end 6061 of the anvil extension rod 606 is cross-sectionally larger than the inner diameter of the recess 6086 of the anvil sleeve 608. The anvil extension rod 606 also has a proximal end 6063 that defines a trocar receiving slot 6065.

FIG. 15(b) is an exploded, perspective view that illustrates some of the components of the staple and blade portion 606, according to one embodiment of the present invention. As shown in FIG. 15(b), the staple and blade portion 606 includes a hollow anvil sleeve guide 610. The inner surface of the anvil sleeve guide 610 includes one or more keyways 6101. The outer surface of the anvil sleeve guide 610 includes a lip 6102, such that a proximal end 6103 of the anvil sleeve guide 610 has a larger radius than a distal end 6104 of the anvil sleeve guide 610.

The staple and blade portion 606 also includes an outer housing sleeve 612. The outer housing sleeve 612 has one or more openings 6121 at its proximal end 6122, and a radially inwardly-extending lip 6123 at the distal end 6124 of the outer housing sleeve 612. The staple and blade portion 106 also includes a staple cartridge 614. The staple cartridge 614 defines a plurality of axially-disposed staple receiving slots 6141 in which staples 6142 are stored. In the embodiment shown in FIG. 15(b), the staple receiving slots 6141 are disposed circumferentially around the staple cartridge 614 in two radially-spaced apart rows, wherein the staple receiving slots 6141 in the first row overlap the staple receiving slots 6141 in the second row. The staple cartridge 614 also includes a radially inwardly-extending lip 6145 and a radially outwardly-extending lip 6143 located near the proximal end 6144 of the staple cartridge 614. Furthermore, the distal end 6147 of the staple cartridge 614 defines a clamping face 6146.

The staple and blade portion 606 also includes a frangible blade protection ring 616 and a cartridge pusher element 617. The cartridge pusher element 617 has a radially outwardly-extending rib 6171 at its distal end. In addition, the staple and blade portion 106 includes a blade 618. The blade 618 has a cutting edge 6183 that extends circumferentially along its distal end. In addition, the blade 618 defines a radially, inwardly-extending tab or lip 6181 at its proximal end.

The staple and blade portion 606 also includes a staple pusher 620. The staple pusher 620 has a plurality of axially-disposed pushing teeth 6201, each of which corresponds to and aligns with the staple receiving slots 6141 of the stapler cartridge 614. The staple pusher 620 also includes a key 6202 on its outer surface.

The staple and blade portion 606 also includes a staple pusher carriage element 622 that has a neck portion 6221 and a flange portion 6222, the neck portion 6221 extending axially in a distal direction relative to the flange portion 6222. An interior surface of the neck portion 6221 includes threads 6223, while an exterior surface of the neck portion 6221 defines a circumferentially-disposed recess 6224. In addition, the radially outermost edge of the flange 6222 includes a key 6225.

Figure 15C:
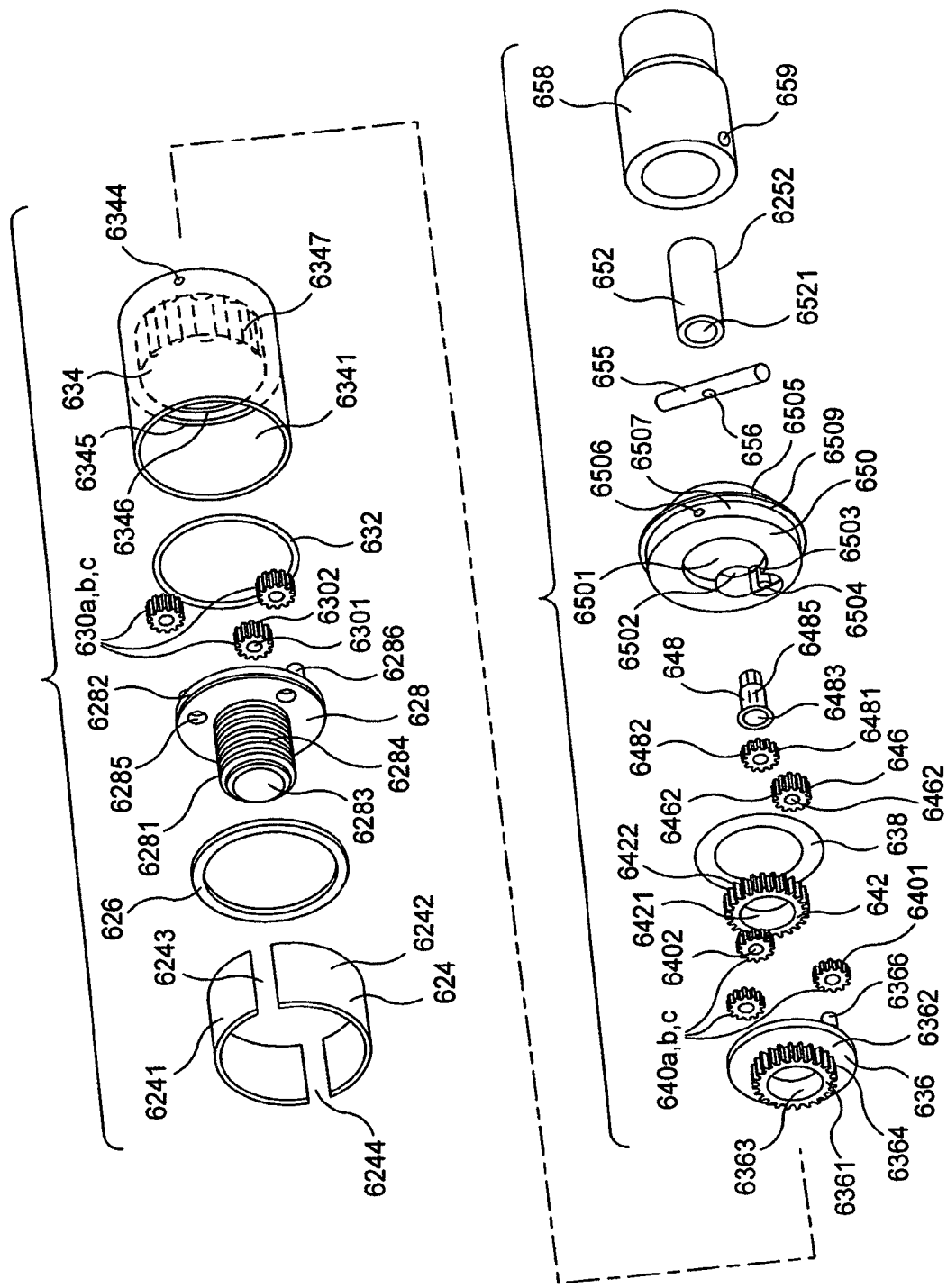
FIG. 15(c) is an exploded, perspective view that illustrates the remaining components of the staple and blade portion shown in FIG. 15(a).

FIG. 15(c) is a perspective view that illustrates the remaining components of the staple and blade portion 606 in an exploded condition, according to one embodiment of the present invention. As shown in FIG. 15(c), the staple and blade portion 606 also includes a split ring 624. The split ring 624 includes a pair of semi-circular ring portions 6241 and 6242 that when arranged in the shape of a ring define therebetween a pair of keyways 6243 and 6244. The staple and blade portion 606 also includes a washer 626. The staple and blade portion 606 also includes a thrust element 628 that has a neck portion 6281 and a flange portion 6282, the neck portion 6281 extending axially in a distal direction relative to the flange portion 6282. A bore 6283 is defined within the interior of the neck portion 6281, while an exterior surface of the neck portion 6281 defines threads 6284 that correspond to the threads 6223 located on the interior surface of the neck portion 6221 of the staple pusher carriage element 622. The flange 6282 of the thrust element 628 includes one or more bores 6285 within its distally-facing surface, and three proximally-extending pins 6286 having, e.g., a round cross section.

The staple and blade portion 606 includes a first spur gear 630a, a second spur gear 630b and a third spur gear 630c. Each of the first, second and third spur gears 630a, 630b, 630c define an internal bore 6301 that corresponds cross-sectionally to a pin 6286 of the thrust element 628. Each of the first, second and third spur gears 630a, 630b, 630c also includes circumferentially-disposed spur gear teeth 6302.

The staple and blade portion 606 also includes a washer 632, and an inner housing sleeve 634. The inner housing sleeve 634 includes an internal bore 6341 that has a first interior radius at a distal end of the inner housing sleeve 634. The internal bore 6341 extends proximally towards a radially inwardly-extending lip 6345 at which point the interior radius of the internal bore 6341 is reduced. The internal bore 6341 extends still further proximally to a second radially inwardly-extending lip 6346 at which point the interior radius of the internal bore 6341 is again reduced. Proximal to the second lip 6346 are gear teeth 6347 that extend circumferentially along the interior surface of the inner housing sleeve 634. A proximal end, e.g., proximal relative to the gear teeth 6347, has a smooth interior surface, and has one or more radial openings 6344 defined therein.

The staple and blade portion 606 also includes a sun gear element 636 that has a neck portion 6361 and a flange portion 6362, the neck portion 6361 extending axially in a distal direction relative to the flange portion 6362. A bore 6363 is defined within the interior of the neck portion 6361, while an exterior surface of the neck portion 6361 has circumferentially-disposed gear teeth 6364 that correspond to the gear teeth 6302 of the first spur gear 630. The flange portion 6362 includes three proximally-extending pins 6366 having, e.g., a round cross section. The staple and blade portion 606 also includes a washer 638.

The staple and blade portion 606 also includes a first planetary gear 640a, a second planetary gear 640b and a third planetary gear 640c. Each of the first, second and third planetary gears 640a, 640b, 640c define an internal bore 6401 that corresponds cross-sectionally to a pin 6366 of the thrust element 636. Each of the first, second and third planetary gears 640a, 640b, 640c also includes circumferentially-disposed gear teeth 6402.

The staple and blade portion 606 also includes a sun gear 642 having an internal bore 6421. An exterior surface of the sun gear 242 has circumferentially-disposed gear teeth 6422 that correspond to the gear teeth 6402 of the first, second and third planetary gears 640a, 640b and 640c. The staple and blade portion 606 also includes a second planetary gear 646 having an internal bore 6461. An exterior surface of the second planetary gear 646 has circumferentially-disposed gear teeth 6462 that correspond to circumferentially-disposed gear teeth 6422 of the sun gear 642.

The staple and blade portion 606 also includes a input element 648, a distal end 6481 of which has an internal bore 6483, into which is non-rotatably inserted, e.g., via a square cross-section, a gear element 6483. On an outer surface of the gear element 6483 are circumferentially-disposed gear teeth 6482 that correspond to the circumferentially-disposed gear teeth 6462 on the exterior surface of the second planetary gear 646. A proximal end of the input element 648 has a round outer circumference and an internal bore 6485.

The staple and blade portion 606 also includes a housing rear endcap 650 having a central bore 6501, a second bore 6502 radially offset relative to the central bore 6501, and a recess 6503 from which a pin 6504 extends in a distal direction. The housing rear endcap 650 also includes an outer radial lip 6505. Located distally relative to the outer radial lip 6505 is at least one opening 6506 defined within a round outer circumferential surface 6507. The housing rear endcap 650 also includes at its proximal end one a radial bore 6509 in communication with the central bore 6501.

The staple and blade portion 606 also includes a central rear endcap sleeve 652 having an axial bore 6521 extending therethrough. In addition, the central rear endcap sleeve 652 has radial bores 6252 extending therethrough. The staple and blade portion 606 also includes a pin stop 655 that is sized and shaped to be inserted through radial openings 6509 of the housing rear end cap 650. The pin stop 655 is also sized and shaped to be inserted through radial openings 659 of an insertion tube 658. When the pin stop 655 is simultaneously inserted through the radial openings 6509 of the housing rear end cap 650 and the radial openings 659 of the insertion tube 658, the housing rear end cap 650 and the insertion tube 658 are fixed in position relative to each other. The insertion tube 658 is employed to connect the handle portion, e.g., the handle portion 102 illustrated in FIGS. 7(*a*) to 7(*f*) or the handle portion 5102 illustrated in FIGS. 13(*a*) to 13(*c*), to the staple and blade portion, e.g., the staple and blade portion 106 illustrated in FIGS. 9 to 11(*b*) or the staple and blade portion 606 illustrated in FIGS. 15(*a*) to 15(*c*). Advantageously, the insertion tube 6258 is formed of a tissue-compatible, sterilizable elastomeric material. Preferably, the insertion tube 6258 may be formed of a material that is autoclavable. In addition, the insertion tube 6258 may be formed of a material having a high or relatively high lubricity. For instance, the insertion tube 6258 may be formed of a material such as Teflon™ (i.e., a fluoropolymer, e.g., polytetrafluoroethylene—"PTFE"), silicone, a Teflon™/silicone combination, such as, for example, SIL-KORE™ (made by W.L. Gore & Associates), "EPTFE", e.g., expanded teflon, etc. Other suitable materials that may be employed are described in further detail in Applicants' co-pending U.S. patent application Ser. No. 10/099,634, filed on Mar. 15, 2002 (now U.S. Pat. No. 7,951,071), which as previously mentioned is expressly incorporated herein by reference in its entirety.

FIG. 15(*d*) is a side cross-sectional view that illustrates some of the components of the staple and blade portion 606 in an assembled condition. The components of the staple and blade portion 606 not shown in FIG. 15(*d*) are generally arranged in a manner similar to the arrangement of the staple and blade portion 106 shown in FIGS. 11(*a*) and 11 (*b*). Referring to FIG. 15(*d*), the thrust element 628 (shown partially here for clarity) is rotatably mounted on the anvil sleeve guide 610 (not shown). The staple pusher carriage element 622 is mounted on the thrust element 628 such that the threads 6223 located on the interior surface of the neck portion 6221 of the staple pusher carriage element 622 are in threaded engagement with the threads 6284 located on the exterior surface of the neck portion 6281 of the thrust element 628. The staple pusher carriage element 622 is axially slidable within the outer housing sleeve 612.

Abutting the flange 6222 of the staple pusher carriage element 622 is the staple pusher 620. The staple pusher 620 is axially slidable within the outer housing sleeve 612. The pushing teeth 6201 of the staple pusher 620 extend distally and align with the staple receiving slots 6141 of the staple cartridge 614.

The staple cartridge 614 is positioned distally relative to the staple pusher 620 and is maintained within the interior of the outer housing sleeve 612. The staple cartridge 614 is axially moveable in a distal direction within the outer housing sleeve 612 from the position shown in FIG. 14 until the radially, outwardly-extending lip 6143 of the staple cartridge 614 abuts the radially, inwardly-extending lip 6123 of the outer housing sleeve 612.

Located between the staple pusher 620 and the staple pusher carriage element 622 is the blade 618. The radially, inwardly-extending tab or lip 6185 located at the distal end of the blade is engaged within the recess 6224 located on the outer surface of the neck portion 6221 of the staple pusher carriage element 622. The cutting edge 6183 of the blade 618 is sheathed within the frangible blade protection ring 616. A proximal end of the frangible blade protection ring 616 abuts the radially inwardly-extending lip 6144 of the staple cartridge 614.

A staple cartridge pusher 617 is positioned along the blade 618 such that the proximal end of the staple cartridge pusher 617 abuts the staple pusher 620. The radially outwardly-extending rib 6171 of the staple cartridge pusher 617 abuts the radially inwardly-extending lip 6145 of the staple cartridge 614. The radially outwardly-extending rib 6171 of the staple cartridge pusher 617 is sized and shaped such that, initially, the radially outwardly-extending rib 6171 of the staple cartridge pusher 617 is larger than the distance between the radially inwardly-extending lip 6145 of the staple cartridge 614 and the outer surface of the blade 618.

In operation, the components of the staple and blade portion 606 not shown in FIG. 15(*d*) generally operate in a manner similar to the operation of those components of the staple and blade portion 106 shown in FIGS. 11(*a*) and 11(*b*), as set forth more fully above. Referring to FIG. 15(*d*), the thrust element 628 is caused to rotate around the anvil sleeve guide 610 by, e.g., operation by the user of the first rotatable drive shaft 30 of the flexible shaft 20 in, e.g., a second direction.

The rotation of the thrust element 628 in the second direction around the anvil sleeve guide 610 causes the staple pusher carriage element 622, by virtue of the threads 6284 located on the exterior surface of the neck portion 6281 of the thrust element 628 being in threaded engagement with the threads 6223 located on the interior surface of the neck portion 6221 of the staple pusher carriage element 622, to move relative to the thrust element 628. Because the keys 6225 of the staple pusher carriage element 622 are engaged within the keyways 6243 formed by the split ring 624, the staple pusher carriage element 622 is caused to axially slide within the split ring 624 in the distal direction. The distal movement of the staple pusher carriage element 622 causes the staple pusher 620, by virtue of the abutment of the flange 6282 of the thrust element 628 with the staple pusher 620, to also move in the distal direction.

Movement of the staple pusher 620 in the distal direction causes the blade 618, and the frangible blade protection ring 616 that covers the cutting edge 6183 of the blade 618, to also move along with the staple pusher 620 in the distal direction. Furthermore, because the radially outwardly-extending rib 6171 of the staple cartridge pusher 617 is initially larger than the distance between the radially inwardly-extending lip 6145 of the staple cartridge 614 and the outer surface of the blade 618, movement of the staple pusher 620 in the distal direction also causes the staple cartridge 614 to move along with the staple pusher 620 in the distal direction. Thus, at this stage of operation, the staple pusher 620, the blade 618, the frangible blade protection ring 616, the cartridge pusher element 617 and the staple cartridge 614 move distally together. The staple cartridge 614 moves distally so as to clamp a section of tissue (not shown) between the clamping face 6023 of the anvil endcap 602 and the clamping face 6146 of the staple cartridge 614. Depending on the thickness of the section of tissue, the staple cartridge 614 may move distally until the radially outwardly-extending lip 6143 of the staple cartridge 614 abuts the radially, inwardly-extending lip 6123 of the outer housing sleeve 612.

Once the staple cartridge 614 has been moved distally sufficiently to clamp a section of tissue, the frangible blade protection ring 616 and the staple cartridge 614 are prevented from further distal movement by contact with a compressed section of tissue. Continued operation of the second rotatable drive shaft 32 eventually causes, e.g., upon the exertion of approximately 70 lbs. or more of pressure on the clamped section of tissue, the radially outwardly-extending rib 6171 of the staple cartridge pusher 617 to be pushed between the radially inwardly-extending lip 6145 of the staple cartridge 614 and the outer surface of the blade 618, thereby overcoming the interference fit between these components. At this point, the staple cartridge 614 does not move distally but instead, the staple pusher 620 and the blade 618 are caused to continue to move distally relative to the staple cartridge 614. This continued distal movement of the blade 618 causes the cutting edge 6183 of the blade 618 to penetrate the frangible blade protection ring 616 and to thereby cut the section of tissue that has been clamped. Simultaneously, further distal movement of the staple pusher 620 causes the pushing teeth 6201 of the staple pusher 620, which are aligned with the staple receiving slots 6141 of the stapler cartridge 614, to begin moving distally through the staple receiving slots 6141. The staples 6142 that are maintained within the staple receiving slots 6141 of the stapler cartridge 614 are thereby pushed through the section of clamped tissue and into the staple guides 6026 of the clamping face 6023 of the anvil endcap 602 until the staples 6142 are closed.

Upon the staples 6142 being fully closed, the clamping force on the section of tissue may be reduced by rotation of the second drive shaft 32 in the opposite direction. Generally, when the second drive shaft 32 is rotated in the opposite direction, the thrust element 628 is caused, via the reverse movement of the components of the staple and blade portion 106, to also rotate in a direction opposite of that described above, thereby causing the staple pusher carriage element 622 to be retracted, e.g., moved proximally. The blade 618 is also caused to be retracted, e.g., moved proximally, by the lip 6185 of the blade 618 being engaged within the recess 6224 located on the outer surface of the neck portion 6221 of the staple pusher carriage element 622. In addition, the staple cartridge 614 is caused to be retracted by the interference fit of the radially outwardly-extending rib 6171 of the staple cartridge pusher 617 maintained between the radially inwardly-extending lip 6145 of the staple cartridge 614 and the outer surface of the blade 618. Once the clamping force between the clamping face 6023 of the anvil endcap 602 and the clamping face 6146 of the staple cartridge 614 has been sufficiently reduced, the section of tissue that has been cut and stapled may be removed from between the clamping face 6023 of the anvil endcap 602 and the clamping face 6146 of the staple cartridge 614, and the surgical attachment 600 may be removed from within the patient.

Figure 16:
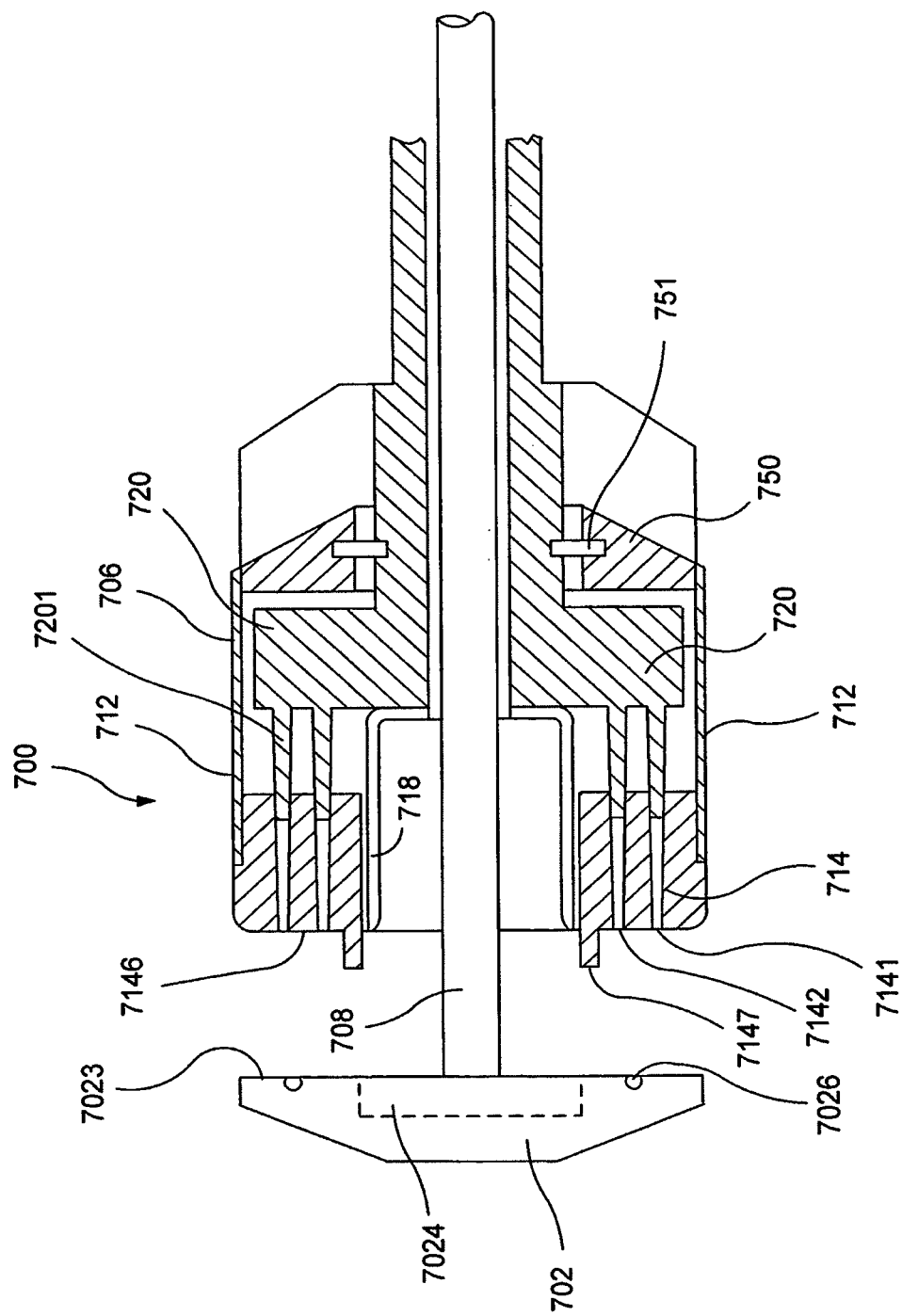
FIG. 16 is a side cross-sectional view that illustrates schematically some components of a surgical attachment, in accordance with another embodiment of the present invention.

FIG. 16 is a side cross-sectional view that illustrates schematically some components of a surgical attachment 700 in accordance with another embodiment of the present invention. The surgical attachment 700 includes an anvil endcap 702 that is connected to a trocar shaft 708, e.g., a cable. The anvil endcap 702 includes a clamping face 7023. The clamping face 7023 has recessed portion that forms a blade repository 7024. The clamping face 7023 also defines staple guides 7026. The trocar shaft 708 extends through a staple and blade portion 706 and is moveable relative to the staple and blade portion 706 by the trocar shaft 708 being extended and retracted, e.g., by operation of a rotatable drive shaft such as the first rotatable drive shaft 30 shown and described in connection with FIG. 1.

The staple and blade portion 706 includes a outer housing sleeve 712 that is fixedly connected at its proximal end to a housing rear end cap 750 and that is fixedly connected at its distal end to a staple cartridge 714. The staple cartridge 714 defines a plurality of staple receiving slots 7141 in which staples 7142 are disposed. The staple receiving slots 7141 are configured so as to correspond to and be aligned with the staple guides 7026 defined in the clamping face 7023 of the anvil endcap 702. The distal end of the staple cartridge 714 defines a clamping face 7146 which has one or more distal protrusions 7147.

The staple and blade portion 706 also includes a staple pusher 720 having staple pusher fingers 7201 that are configured so as to correspond to and be aligned with the staple receiving slots 7141 of the staple cartridge 714. Mounted at a distal end of the staple pusher 720 is a blade 718. At a proximal end of the staple pusher 720 are shear pins 751 which, at least initially, connect the staple pusher 720 to the housing rear end cap 750.

In operation, a section of tissue, such as a section of oral tissue that is desired to be cut and stapled, is disposed between the clamping face 7023 of the anvil endcap 702 and the clamping face 7146 of the staple cartridge 714. Upon operation of a suitable drive mechanism, e.g., the first rotatable drive shaft 30, the trocar shaft 708 is retracted relative to the staple and blade portion 706 until the section of tissue is sufficiently clamped between the clamping face 7023 of the anvil endcap 702 and the clamping face 7146 of the staple cartridge 714. Once the section of tissue is sufficiently clamped between the clamping face 7023 of the anvil endcap 702 and the clamping face 7146 of the staple cartridge 714, continued operation of the suitable drive mechanism, e.g., the first rotatable drive shaft 30, causes the shear pins 751 to shear. Advantageously, the pressure at which the shear pins 751 shear is predetermined to be a pressure at which the section of tissue is optimally clamped prior to being cut and stapled. Once the shear pins 751 are caused to shear, the staple cartridge 714, along with the outer housing sleeve 712 and the housing rear end cap 750, is permitted to move proximally relative to the staple pusher 720. Proximal movement of the staple cartridge 714 relative to the staple pusher 720 causes the staple pusher fingers 7201 of the staple pusher 720 to move through the respective staple receiving slots 7141 of the staple cartridge 714. By continued operation of the suitable drive mechanism, e.g., the first rotatable drive shaft 30, the staples 7142 are gradually pushed out of the staple receiving slots 7141 of the staple cartridge 714, through the section of tissue and against the staple guides 7026 of the anvil endcap 702 until the staples 7142 are closed. In addition, and generally simultaneously, once the shear pins 751 are caused to shear, the staple cartridge 714 is caused to move proximally relative to the blade 718 mounted at the distal end of the staple pusher 720. Proximal movement of the staple cartridge 714 relative to the blade 718 causes the blade 718 to penetrate the section of tissue clamped between the clamping face 7023 of the anvil endcap 702 and the clamping face 7146 of the staple cartridge 714. By continued operation of the suitable drive mechanism, e.g., the first rotatable drive shaft 30, the blade 718 is gradually pushed through the section of tissue and into the blade repository 7024 of the anvil endcap 702 until the section of tissue is completely cut.

Thus, the surgical attachment 700, in accordance with one embodiment of the present invention, provides an arrangement in which the staple pusher 720, the staples 7142 and the blade 718 are held in a relatively stationary position. The anvil assembly 712 is caused to be moved relative to the staple pusher 720, the staples 7142 and the blade 718 so as to cut and staple the section of tissue disposed therebetween. This arrangement may provide for improved performance due to the increased clamping forces that may be applied as compared to conventional circular cutting and stapling devices. These increased clamping forces may be possible because, unlike conventional circular cutting and stapling devices that employ a gear arrangement or the like to push a staple pusher, staples and a blade against a stationary anvil, the surgical attachment 700 provides an arrangement in an anvil assembly is pulled towards and against a staple pusher, staples and a blade that are held in a relative stationary position.

Figure 17:
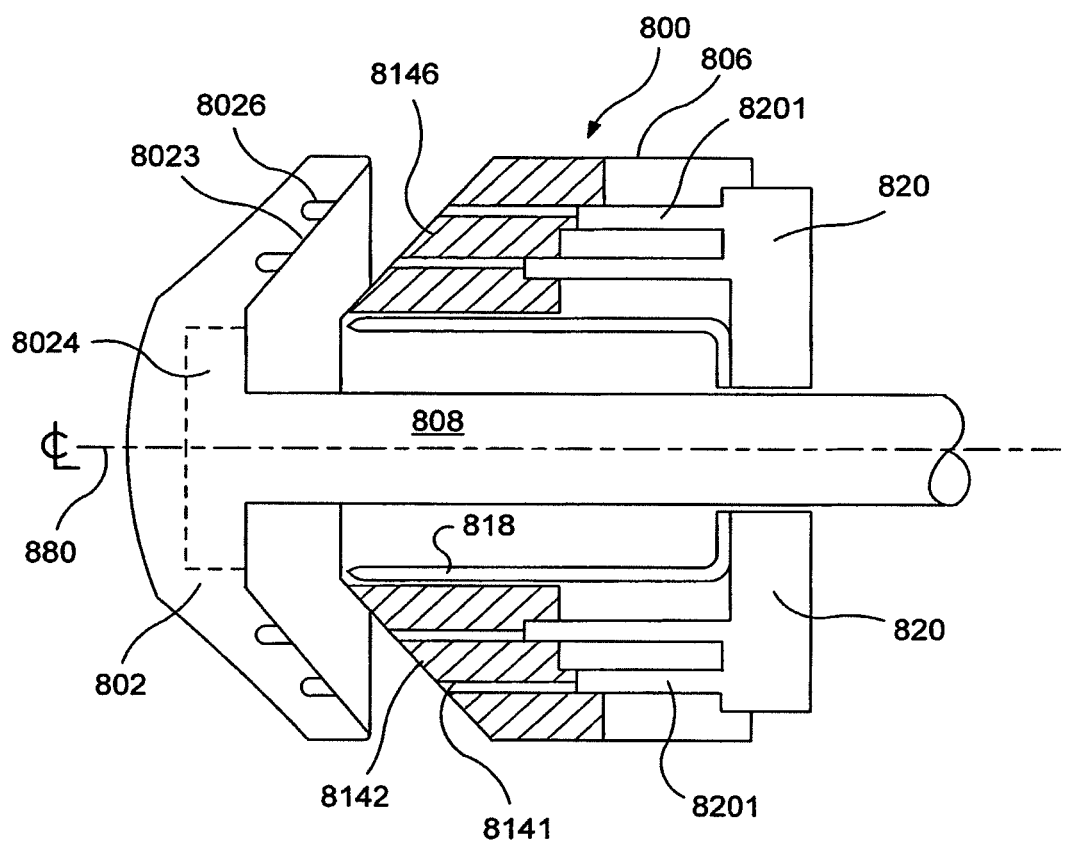
FIG. 17 is a side cross-sectional view that illustrates schematically some components of a surgical attachment, in accordance with another embodiment of the present invention.

FIG. 17 is a side cross-sectional view that illustrates schematically some components of a surgical attachment 800 in accordance with another embodiment of the present invention. The surgical attachment 800 includes an anvil endcap 802 that is connected to a trocar shaft 808, e.g., a cable. The anvil endcap 802 includes a clamping face 8023. The clamping face 8023 is not perpendicular, e.g., sloped, relative to an axis 880 defined by the trocar shaft 808. The clamping face 8023 has a recessed portion that forms a blade repository 8024. The clamping face 8023 also defines staple guides 8026. The trocar shaft 808 extends through a staple and blade portion 806 and is moveable relative to the staple and blade portion 806 by the trocar shaft 808 being extended and retracted, e.g., by operation of a rotatable drive shaft such as the first rotatable drive shaft 30 shown and described in connection with FIG. 1.

The staple and blade portion 806 includes a staple cartridge 814. The staple cartridge 814 defines a plurality of staple receiving slots 8141 in which staples 8142 are disposed. The staple receiving slots 8141 are configured so as to correspond to and be aligned with the staple guides 8026 defined in the clamping face 8023 of the anvil endcap 802. The distal end of the staple cartridge 814 defines a clamping face 8146. The clamping face 8146 is not perpendicular, e.g., sloped, relative to the axis 880 defined by the trocar shaft 808. Preferably, the clamping face 8023 is shaped and oriented so as to be parallel to the clamping face 8023 of the anvil endcap 802.

The staple and blade portion 806 also includes a staple pusher 820 having staple pusher fingers 8201 that are configured so as to correspond to and be aligned with the staple receiving slots 8141 of the staple cartridge 814. Mounted at a distal end of the staple pusher 820 is a blade 818.

In operation, a section of tissue, such as a section of oral tissue that is desired to be cut and stapled, is disposed between the clamping face 8023 of the anvil endcap 802 and the clamping face 8146 of the staple cartridge 814. Upon operation of a suitable drive mechanism, e.g., the first rotatable drive shaft 30, the trocar shaft 808 is retracted relative to the staple and blade portion 806 until the section of tissue is sufficiently clamped between the clamping face 8023 of the anvil endcap 802 and the clamping face 8146 of the staple cartridge 814. The mechanical arrangement by which operation of the suitable drive mechanism, e.g., the first rotatable drive shaft 30, causes the trocar shaft 808 to be retracted relative to the staple and blade portion 806 may be a gear arrangement such as described hereinabove, or may be any other suitable mechanical arrangement. Once the section of tissue is sufficiently clamped between the clamping face 8023 of the anvil endcap 802 and the clamping face 8146 of the staple cartridge 814, continued operation of the suitable drive mechanism, e.g., the first rotatable drive shaft 30, causes the staple cartridge 814 and the staple pusher 820 to move relative to each other. This relative movement may be facilitated by the staple pusher 820 being pushed relative to the staple cartridge 814 by a suitable drive mechanism, some examples of which are described hereinabove, or may be facilitated by the anvil endcap 802 being pulled relative to the staple pusher 820, such as described above in connection with FIG. 16. Any other mechanical arrangement may also be employed for this purpose. Movement of the staple cartridge 814 relative to the staple pusher 820 causes the staple pusher fingers 8201 of the staple pusher 820 to move through the respective staple receiving slots 8141 of the staple cartridge 814. By continued operation of the suitable drive mechanism, e.g., the first rotatable drive shaft 30, the staples 8142 are gradually pushed out of the staple receiving slots 8141 of the staple cartridge 814, through the section of tissue and against the staple guides 8026 of the anvil endcap 802 until the staples 8142 are closed. In addition, and generally simultaneously, movement of the staple cartridge 814 relative to the blade 818, which is mounted at the distal end of the staple pusher 820, causes the blade 818 to penetrate the section of tissue clamped between the clamping face 8023 of the anvil endcap 802 and the clamping face 8146 of the staple cartridge 814. By continued operation of the suitable drive mechanism, e.g., the first rotatable drive shaft 30, the blade 818 is gradually pushed through the section of tissue and into the blade repository 8024 of the anvil endcap 802 until the section of tissue is completely cut.

The surgical attachment 800, in accordance with one embodiment of the present invention, provides an arrangement in which the staple and blade portion 806 may be inserted more easily into a patient's body. In conventional circular cutting and stapling devices, the staple and blade portion typically has a perpendicularly-arranged clamping face, e.g., a clamping face that is perpendicular to the general axis defined by the staple and blade portion or by the trocar shaft passing through the staple and blade portion. This perpendicularly-arranged clamping face meets the outer housing of the staple and blade portion at a circumferential edge which, in cross-section, is essentially a right angle. When inserted into a patient, particularly an oral passage of a patient that has a very small cross-sectional area, the circumferential edge formed by the perpendicularly-arranged clamping face and the outer housing of the staple and blade portion rub against the internal surface of the oral passage and thereby make insertion difficult. Furthermore, the rubbing of the circumferential edge against the internal surface of the oral passage may damage the oral passage. In contrast, the non-perpendicular, e.g., sloped, arrangement of the clamping face 8146 of the staple cartridge 814 reduces the degree of rubbing against the internal surface of the oral passage that is experienced, thereby easing insertion of the staple and blade portion 806 through the oral passage and reducing the likelihood of injury to the internal surface of the oral passage.

Figure 18A:
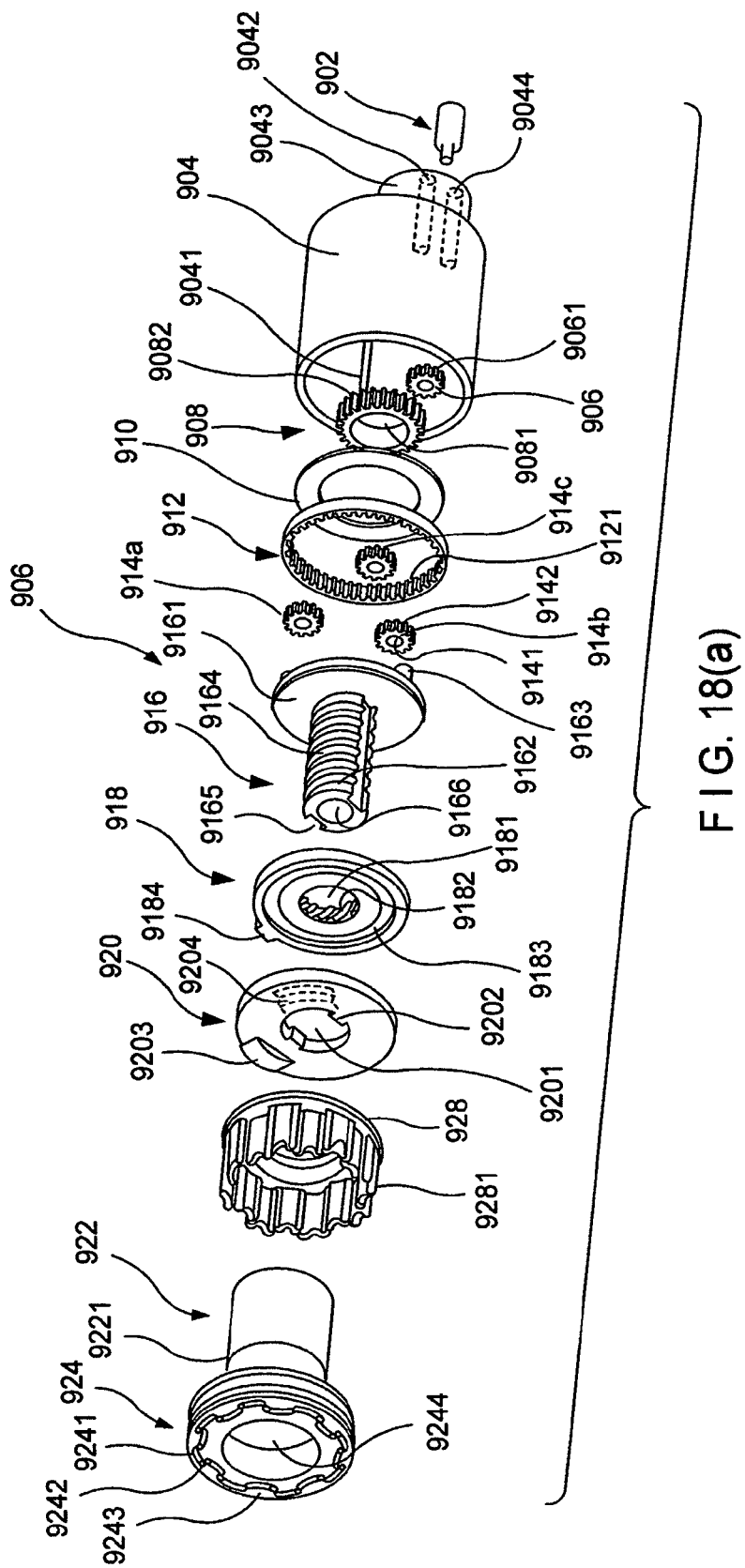
FIG. 18(a) is an exploded, perspective view that illustrates some of the components of a staple and blade portion, according to another embodiment of the present invention.
Figure 18B:
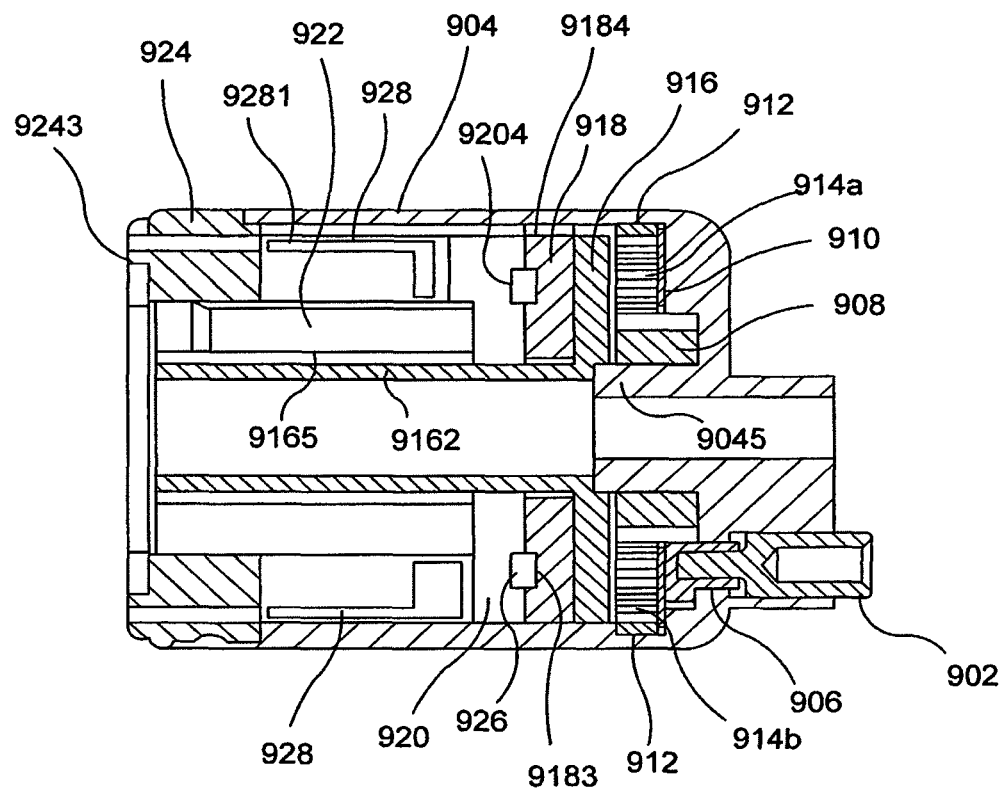
FIG. 18(b) is an assembled, side cross-sectional view that illustrates the components of the staple and blade portion shown in FIG. 18(a).

FIGS. 18(a) and 18(b) illustrate a staple and blade portion, according to another embodiment of the present invention. Specifically, FIG. 18(a) is an exploded, perspective view that illustrates some of the components of a staple and blade portion 906. As shown in FIG. 18(a), the staple and blade portion 906 includes an outer housing sleeve 904. The outer housing sleeve 904 has a gear housing 9043, defining an axial bore 9042 and a second bore 9044, at its proximal end. The outer housing sleeve 904 also has a keyway 9041 that extends longitudinally along its inner surface.

The staple and blade portion 906 also includes an input shaft 902 that is configured to be non-rotatably connected to a drive shaft, e.g., second rotatable drive shaft 104b of the flexible shaft 104, which in turn may be connected via a handle portion, e.g., the handle portion 102 to the second rotatable drive shaft 32 of the flexible shaft 20. The distal end of the input shaft 902 has an extension which is non-rotatably insertable, e.g., via a square cross-section of the extension, into an input gear 906. On an outer surface of the input gear 906 are circumferentially-disposed gear teeth 9061.

The staple and blade portion 906 also includes a sun gear 908 having a central bore 9081. An exterior surface of the sun gear 908 has circumferentially-disposed gear teeth 9082 that correspond to the gear teeth 9061 of the input gear 906. The staple and blade portion 906 also includes a washer 910. The staple and blade portion 906 also includes a ring gear 912. The ring gear 912 has gear teeth 9121 that extend circumferentially along the interior surface of the ring gear 912.

The staple and blade portion 906 also includes a first planetary gear 914a, a second planetary gear 914b and a third planetary gear 914c. Each of the first, second and third planetary gears 914a, 914b, 914c define an internal bore 9141. In addition, each of the first, second and third planetary gears 914a, 914b, 914c also includes circumferentially-disposed gear teeth 9142.

The staple and blade portion 906 also includes a spider screw element 916 that has a neck portion 9162 and a flange portion 9161, the neck portion 9162 extending axially in a distal direction relative to the flange portion 9162. A central bore 9166 extends through the spider screw element 916. An exterior surface of the neck portion 9162 defines threads 9164. In addition, the exterior surface of the neck portion 9162 defines longitudinally-extending keyways 9165. The flange portion 9161 of the spider screw element 916 includes three proximally-extending pins 9163 having a cross section, e.g., round, that corresponds to the bores 9141 of the first, second and third planetary gears 914a, 914b, 914c.

The staple and blade portion 906 also includes a nut 918 having a generally flat, disk-shaped configuration. The nut 918 has a central bore 9181 extending therethrough. The central bore 9181 defines threads 9182 that correspond to the threads 9164 on the exterior surface of the neck portion 9162 of the spider screw element 916. A distal face of the nut 918 defines a circumferential groove 9183. In addition, the outer radial edge of the nut 918 defines a key 9184 that corresponds in size and shape to the keyway 9041 on the internal surface of the outer housing sleeve 904.

The staple and blade portion 906 also includes a rotary pusher 920 that also has a generally flat, disk-shaped configuration. The rotary pusher 920 has a central bore 9201 extending therethrough. The central bore 9181 defines keys 9202 that correspond in size and shape to the keyways 9165 extending longitudinally on the neck portion 9162 of the spider screw element 916. A proximal face of the rotary pusher 920 defines a circumferential groove 9204 that is aligned with the circumferential groove 9183 on the distal face of the nut 918. On a distal face of the rotary pusher 920 there is disposed a pusher cam 9203.

In addition, the staple and blade portion 906 includes a blade 922. The blade 922 has a cutting edge 9221 that extends circumferentially along its distal end. The staple and blade portion 906 also includes a staple cartridge 924. The staple cartridge 924 defines a plurality of axially-disposed staple receiving slots 9241 in which staples 9242 are stored. In the embodiment shown in FIG. 18(a), the staple receiving slots 9241 are disposed circumferentially around the staple cartridge 924 in two radially-spaced apart rows, wherein the staple receiving slots 9241 in the first row overlap the staple receiving slots 9241 in the second row. Furthermore, the distal end of the staple cartridge 924 defines a clamping face 9243.

The staple and blade portion 906 also includes a staple pusher 928. The staple pusher 928 has a plurality of axially-disposed pushing teeth 9281, each of which corresponds to and aligns with the staple receiving slots 9241 of the stapler cartridge 924. The staple pusher 928 also includes a key 9202 on its outer surface.

FIG. 18(b) is a side cross-sectional view that illustrates the components of the staple and blade portion 906 in an assembled condition. The input shaft 902 extends through and is configured to rotate within the second bore 9044 of the gear housing 9043. The input gear 906 is mounted on and non-rotatably connected to the distal end of the input shaft 902. The sun gear 908 is seated within the proximal end of the outer housing sleeve 904 such that a distally-extending cylindrical core 9045 of the outer housing sleeve 904 is inserted through the central bore 9081 of the sun gear 908. The circumferentially-disposed gear teeth 9061 on the outer surface of the input gear 906 are in meshing engagement with the circumferentially-disposed gear teeth 9082 of the sun gear 908. The ring gear 912 is fixed within the proximal end of the outer housing sleeve 904. The first, second and third planetary gears 914a, 914b, 914c are positioned radially between the sun gear 908 and the ring gear 912, such that the circumferentially-disposed gear teeth 9142 of the first, second and third planetary gears 914a, 914b, 914c are in meshing engagement with the gear teeth 9121 that extend circumferentially along the interior surface of the ring gear 912 and with the gear teeth 9082 of the sun gear 908. The washer 910 abuts the proximal side of the first, second and third planetary gears 914a, 914b, 914c and the distal side of the input gear 906 so as to prevent axial movement of these components.

The pins 9163 extending from the flange portion 916 of the spider screw element 916 are inserted in the internal bores 9141 of the first, second and third planetary gears 914a, 914b, 914c and thereby maintain the circumferential spacing of the first, second and third planetary gears 914a, 914b, 914c. Thus, the flange portion 9161 of the spider screw element 916 abuts the distal side of the first, second and third planetary gears 914a, 914b, 914c.

The neck portion 9162 of the spider screw element 916 extends distally through the central bore 9181 of the nut 918 such that the threads 9164 on the exterior surface of the neck portion 9162 are in threaded engagement with the threads 9182 within the central bore 9181 of the nut 918. The key 9184 of the nut 918 is engaged within the keyway 9041 in the internal surface of the outer housing sleeve 904.

The neck portion 9162 of the spider screw element 916 also extends distally through the central bore 9201 of the rotary pusher 920. The keys 9202 in the central bore 9201 of the rotary pusher 920 are engaged within the keyways 9165 in the neck portion 9162 of the spider screw element 916. In addition, a set of ball bearings 926 are positioned in the circumferential grooves 9183 and 9204 of the nut 918 and the rotary pusher 920, respectively, and provide for a generally frictionless contact between the nut 918 and the rotary pusher 920.

The neck portion 9162 of the spider screw element 916 also extends distally through the center of the staple pusher 928 and the blade 922. The proximal ends of the blade 922 and the staple pusher 928 abut the distal face of the rotary pusher 920 the pusher fingers 9281 of the staple pusher 928 extend distally and are aligned with the staple receiving slots 9241 of the staple cartridge 924. The staple cartridge 924 is positioned within the distal end of the outer housing sleeve 904, the clamping face 9243 of which forms the distal face of the staple and blade portion 906.

In operation, a section of tissue, such as a section of oral tissue that is desired to be cut and stapled, is disposed between the clamping face of an anvil assembly, such as an anvil assembly set forth more fully hereinabove, and the clamping face 9243 of the staple cartridge 924. Upon operation of a suitable drive mechanism, e.g., the first rotatable drive shaft 30, a trocar shaft, e.g., a cable, that extends through the staple and blade portion 906 is retracted relative to the staple and blade portion 906 until the section of tissue is sufficiently clamped between the respective clamping faces. The mechanical arrangement by which operation of the suitable drive mechanism, e.g., the first rotatable drive shaft 30, causes the trocar shaft to be retracted relative to the staple and blade portion 906 may be a gear arrangement such as described hereinabove, or may be any other suitable mechanical arrangement.

Referring to FIG. 18(b), the input shaft 902 may be connected to a drive shaft, e.g., the second rotatable drive shaft 104b of the flexible shaft 104. The drive shaft may in turn be connected via a handle portion, e.g., the handle portion 102, to the second rotatable drive shaft 32 of the flexible shaft 20. Rotation of the drive shaft in a first direction, e.g., clockwise, causes the input shaft 902 to rotate in the first direction within the second bore 9044 of the gear housing 9043. By the non-rotatable connection of the distal end of the input shaft 902 with the input gear 906, rotation of the input shaft 902 in the first direction causes the input gear 906 to also rotate in the first direction.

By the meshing engagement of the circumferentially-disposed gear teeth 9061 of the input gear 906 with the circumferentially-disposed gear teeth 9082 of the sun gear 908, rotation of the input gear 906 in the first direction causes the sun gear 908 to rotate around the distally-extending cylindrical core 9045 within the outer housing sleeve 904 in a second direction, e.g., counter-clockwise. Furthermore, by the meshing engagement of the circumferentially-disposed gear teeth 9142 on the outer surfaces of the first, second and third planetary gears 914a, 914b and 914c with the circumferentially-disposed gear teeth 9082 of the sun gear 908, rotation of the sun gear 908 in the second direction causes the first, second and third planetary gears 914a, 914b and 914c to rotate in the first direction. Because the circumferentially-disposed gear teeth 9142 on the outer surfaces of the first, second and third planetary gears 914a, 914b and 914c are also in meshing engagement with the gear teeth 9121 that extend circumferentially along the interior surface of the ring gear 912, and because the ring gear 912 is rotationally fixed within the proximal end of the outer housing sleeve 904, the rotation of the first, second and third planetary gears 914a, 914b and 914c in the first direction results in the first, second and third planetary gears 914a, 914b and 914c revolving around the sun gear 908 in the second direction.

Since the pins 9163 extending from the flange portion 916 of the spider screw element 916 are inserted in the internal bores 9141 of the first, second and third planetary gears 914a, 914b, 914c, the revolving motion of the first, second and third planetary gears 914a, 914b and 914c around the sun gear 908 in the second direction causes the spider screw element 916 to also rotate in the second direction. By the threaded engagement of the threads 9164 on the exterior surface of the neck portion 9162 with the threads 9182 within the central bore 9181 of the nut 918, and because the key 9184 of the nut 918 is engaged within the keyway 9041 in the internal surface of the outer housing sleeve 904, rotation of the spider screw element 916 in the second direction causes the nut 918 to advance distally along the neck portion 9162 of the spider screw element 916.

Because the keys 9202 in the central bore 9201 of the rotary pusher 920 are engaged within the keyways 9165 in the neck portion 9162 of the spider screw element 916, the rotation of the spider screw element 916 in the second direction causes the rotary pusher 920 to be rotated in the second direction. The proximal side of the rotary pusher 920 is in contact with the distal side of the nut 918, and thus the distal advancement of the nut 918 along the neck portion 9162 of the spider screw element 916 causes the rotary pusher 920 to also advance distally along the neck portion 9162 of the spider screw element 916. The set of ball bearings 926 positioned in the circumferential grooves 9183 and 9204 of the nut 918 and the rotary pusher 920, respectively, provide for a generally frictionless contact between the nut 918, which is not rotating, and the rotary pusher 920, which is rotating.

The distal advancement of the rotary pusher 920 along the neck portion 9162 of the spider screw element 916 causes the blade 922 to be moved distally through the central bore 9244 of the staple cartridge 924 to cut a section of tissue that is disposed between the clamping face 9243 of the staple cartridge 924 and the clamping face of an anvil assembly (not shown), such as previously set forth hereinabove. Furthermore, the distal advancement of the rotary pusher 920 along the neck portion 9162 of the spider screw element 916 causes the pusher cam 9203 of the rotary pusher 920 to push the staple pusher element 928 in the distal direction. Since the rotary pusher 920 is simultaneously rotating while it is being distally advanced, the pusher cam 9203 is caused to sequentially contact and push against the staple pusher fingers 9281 of the staple pusher 928. Specifically, as the rotary pusher 920 is gradually rotated around the neck portion 9162 of the spider screw element 916, the pusher cam 9203 contacts and pushes against a first of the staple pusher fingers 9281, then a second of the staple pusher fingers 9281, etc. After a complete rotation of the rotary pusher 920 around the neck portion 9162 of the spider screw element 916, the pusher cam 9203 has contacted and pushed against all of the staple pusher fingers 9281 of the staple pusher 928. Depending on the height of the pusher cam 9203 relative to the distal side of the rotary pusher 920 and on the length of the prongs of the staples 9242, once the pusher cam 9203 contacts the staple pusher 928, several complete rotations of the rotary pusher 920 may be required in order for the pusher cam 9203 to push the staples completely out of the slots 9241 of the staple cartridge 924 and for the staples 9242 to be completely closed against staple guides of the anvil assembly (not shown).

As previously mentioned, one of the problems that is experienced during the use of surgical devices that are inserted within a patients' body, particularly conventional cutting and stapling devices, is that they are required to be inserted into orifices or passages of a patient having a relatively small cross-section, e.g., an oral passage of a patient. Thus, insertion of the surgical device may be difficult or impossible and/or may damage the internal surface of the oral passage. According to one embodiment of the present invention, in order to ease insertion of a surgical device into and through a small orifice or passage of a patient, there may be employed a sleeve. For instance, FIGS. 19(*a*) to 19(*e*) illustrate various sleeves that may be employed to facilitate the insertion of a surgical device into and through a small orifice or passage of a patient.

FIG. 19(*a*) is an exploded, perspective view of a sleeve 8000 that is configured to cover a surgical device, e.g., a circular cutting and stapling device, during insertion into patient's body, according to one embodiment of the present invention. Advantageously, the sleeve 8000 generally has a size and a shape and/or contour that is similar to the size and shape and/or contour of the surgical device that is covered thereby. For the purposes of example only, the sleeves described hereinbelow are recited for use in connection with the surgical attachment 100, although it should be recognized that the sleeves may be employed to cover any type of surgical device. Furthermore, for the purposes of example only, the sleeves described hereinbelow are described as being employed to cover a surgical device for insertion within an oral passage of a patient, although it should be recognized that the sleeves may be employed to cover the insertion of a surgical device into any type of orifice or passage of a patient.

The sleeve 8000 may be formed of a tissue-compatible, sterilizable elastomeric material. Preferably, the sleeve 8000 may be formed of a material that is autoclavable. In addition, the sleeve 8000 may be formed of a material having a high or relatively high lubricity. For instance, the sleeve 8000 may be formed of a material such as Teflon™ (i.e., a fluoropolymer, e.g., polytetrafluoroethylene—"PTFE"), silicone, a Teflon™/silicone combination, such as, for example, SIL-KORE™ (made by W.L. Gore & Associates), "EPTFE", e.g., expanded teflon, etc. Other suitable materials that may be employed are described in further detail in Applicants' copending U.S. patent application Ser. No. 10/099,634, filed on Mar. 15, 2002 (now U.S. Pat. No. 7,951,071), which as previously mentioned is expressly incorporated herein by reference in its entirety.

The sleeve 8000 includes one or more closure elements, such as the closure elements 8020 and 8022, that are configured to be selectively adjusted between an insertion position and a retracted position. The sleeve 8000 also includes a distal portion 8024. The distal portion 8024 may be configured to cover a distal portion of a surgical device, e.g., the staple and blade portion 106 or any other distal portion of a surgical device. The sleeve 8000 may also include a proximal portion 8026. The proximal portion 8026 may be configured to cover a proximal portion of a surgical device. For instance, the proximal portion 8026 of the sleeve 8000 may be configured to cover a flexible shaft, e.g., the flexible shaft 20 or the flexible shaft 104 that are shown and described in connection with FIG. 1, or a handle portion, e.g., the handle portion 102 that is shown and described in connection with FIG. 7(*a*) or the handle portion 5102 that is shown and described in connection with FIG. 13(*a*). A ring introducer element 8010 may be connected to the proximal portion 8026 of the sleeve 8000 and may function to facilitate insertion of the surgical device within the sleeve 8000.

FIG. 19(*b*) is a side cross-sectional view of a portion of the sleeve 8000, according to one embodiment of the present invention. In this embodiment, the closure elements 8020 and 8022 are shown to be tapered so as to form a shape similar to a "duck bill". It should be recognized that the closure elements of the sleeve 8000 may have any suitable shape that provides eased insertion of the surgical attachment 100 into the oral passage. FIG. 19(*b*) illustrates the closure elements 8020 and 8022 in the closed position, in which the sleeve 8000 is suitable for insertion into the oral passage. When the closure elements 8020 and 8022 are in the closed position, as shown, the tapered arrangement of the closure elements 8020 and 8022 enable the sleeve 8000, and the surgical attachment 100 which is covered thereby, to be more easily inserted into the oral passage, thereby reducing the likelihood of injury to an internal surface of the oral passage. In one embodiment, the closure elements 8020 and 8022 may be maintained in the closed position by attachment to a portion of the surgical attachment 100, for instance by attachment to a trocar such as trocar 110 shown and described in connection with FIG. 1.

FIG. 19(c) illustrates the closure elements 8020 and 8022 in the open position. Specifically, after the sleeve 8000 has been inserted into the oral passage, the closure elements 8020 and 8022 may be opened so as to permit the surgical attachment 100 within the sleeve 8000 to perform a desired surgical operation. For instance, the closure elements 8020 and 8022 may be opened so as to permit the anvil assembly 112 to be connected to, then retracted towards and against, the staple and blade portion 106.

Figure 19A:
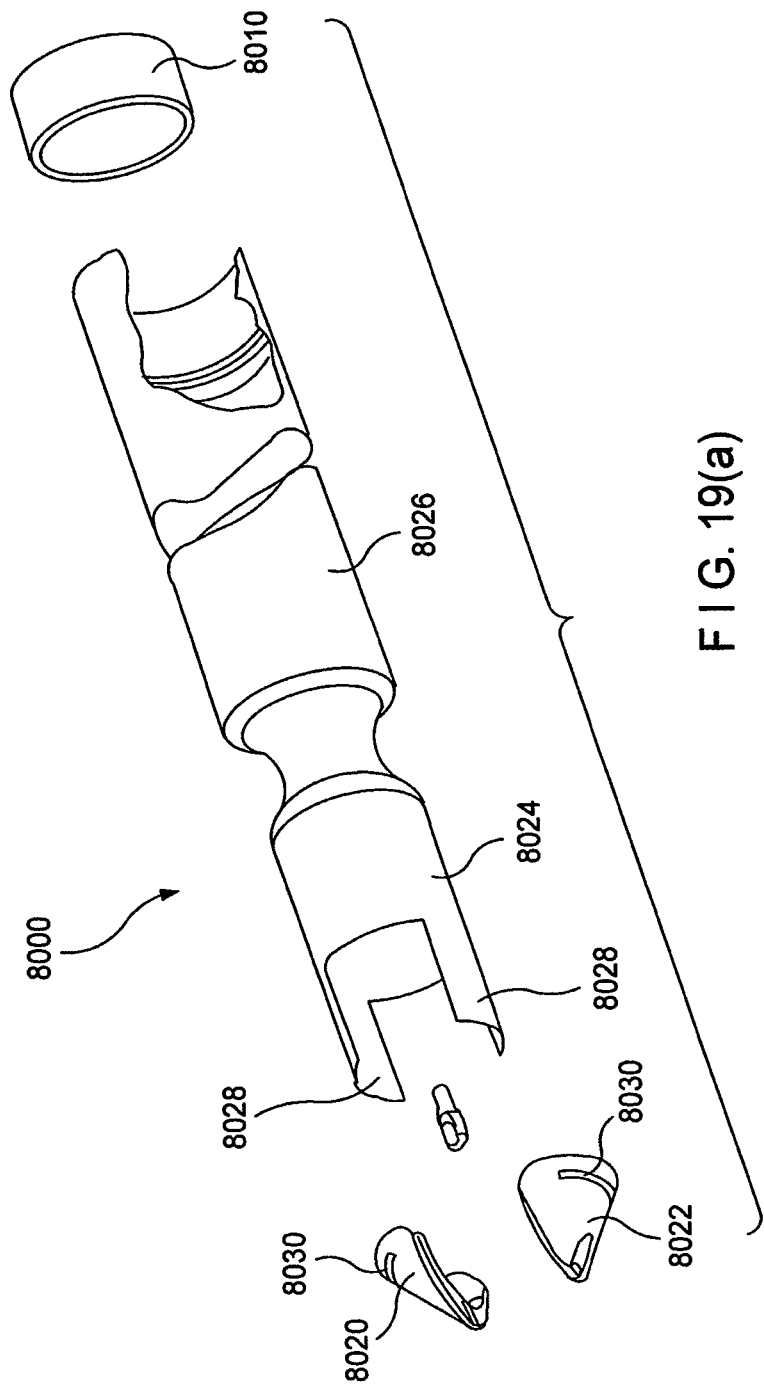
FIG. 19(a) is an exploded, perspective view of a sleeve that is configured to cover a surgical device, according to one embodiment of the present invention.

In order to open the closure elements 8020 and 8022, the distal portion 8024 and/or the closure elements 8020 and 8022 may have a retraction mechanism. For instance, FIG. 19(a) illustrates flaps 8028 that are part of or that extend from the distal portion 8024 of the sleeve 8000. These flaps 8028 may be connected to the closure elements 8020 and 8022, such as by being laminated thereto or by insertion through circumferentially-disposed slots 8030 of the closure elements 8020 and 8022. Thus, after the sleeve 8000 has been inserted into the oral passage, the sleeve 8000 may be moved relative to the surgical attachment 100 in a proximal direction. Movement of the sleeve 8000 relative to the surgical attachment 100 in the proximal direction causes the closure elements 8020 and 8022 to be pivoted or opened.

Depending on the size and shape of the sleeve 8000 and the surgical attachment 100, once the closure elements 8020 and 8022 are opened, the sleeve 8000 may be left in place. In this case, the sleeve 8000 may subsequently be employed, e.g., after the surgical procedure has been completed, to facilitate the removal the surgical attachment 100 from the oral passage. Alternatively, once the closure elements 8020 and 8022 are opened, the sleeve 8000 may be removed from the oral passage—while the surgical attachment 100 remains in the oral passage—by continued movement of the sleeve 8000 relative to the surgical attachment 100 in the proximal direction. In this case, the sleeve 8000, including the closure element 8020 and 8022 are caused to slide over the surgical attachment 100. While the flaps 8028 are shown in FIG. 19(a) as being straight in the longitudinal direction, in other embodiments, the flaps may have a different shape, e.g., hooks, loops, etc.

FIGS. 19(d) and 19(e) illustrate a sleeve 8100, according to another embodiment of the present invention. Specifically, FIG. 19(d) illustrates the sleeve 8100 in an insertion position. In the insertion position, the sleeve 8100 is configured so as to cover the surgical attachment 100, and to provide eased insertion of the surgical attachment 100 into the oral passage.

The sleeve 8100 may include a distal portion 8105. The distal portion 8105 may be configured to cover a distal portion of the surgical attachment 100, e.g., the staple and blade portion 106. The sleeve 8100 may also include a proximal portion 8107. The proximal portion 8107 may be configured to cover a proximal portion of the surgical attachment 100 or any other components that are connected to the surgical attachment 100. For instance, the proximal portion 8107 of the sleeve 8000 may be configured to cover a flexible shaft, e.g., the flexible shaft 20 or the flexible shaft 104 that are shown and described in connection with FIG. 1, or a handle portion, e.g., the handle portion 102 that is shown and described in connection with FIG. 7(a) or the handle portion 5102 that is shown and described in connection with FIG. 13(a).

The sleeve 8100 may also include a closure element. The closure element may be configured as a ring 8102, although other shapes may be employed. When the sleeve 8100 is in the insertion position, the ring 8102 may be positioned such that an axis 8104 that is defined by the ring 8102 is substantially perpendicular to a longitudinal axis 8106 defined by the staple and blade portion 106. The ring 8102 may be maintained in this position by attachment to a portion of the surgical attachment 100, e.g., by attachment to the trocar 110 extending through the staple and blade portion 106. In this position, one side 8110 of the ring 8102 is in contact with the distal side of the staple and blade portion 106, and the opposite side 8112 of the ring 8102 is positioned opposite to the staple and blade portion 106. The round outer circumference of the ring 8102 provides a generally curved surface which, upon insertion into the oral passage, gradually opens the oral passage before the surgical attachment 100 passes therethrough. In this manner, there is provided eased insertion of the surgical attachment 100 into the oral passage.

FIG. 19(e) illustrates the ring 8102 in the retracted position. Specifically, after the sleeve 8100, having the surgical attachment 100 therein, has been inserted into the oral passage, the ring 8102 may be moved relative to the surgical attachment 100 so as to permit the surgical attachment 100 to perform its desired surgical operation. For instance, the ring 8102 may be rotated relative to axis 8109 so as to permit the anvil assembly 112 to be connected to and then retracted towards the staple and blade portion 106. In order to retract the ring 8102, the sleeve 8100 may be moved relative to the surgical attachment 100 in a proximal direction. Movement of the sleeve 8100 relative to the surgical attachment 100 in the proximal direction causes the ring 8102 to be detached from, e.g., the trocar 100 of, the surgical attachment 100 and to be drawn towards and against the staple and blade portion 106. Continued movement of the sleeve 8100 relative to the surgical attachment 100 in the proximal direction causes the ring 8102 to rotate and eventually be positioned such that the axis 8104 defined by the ring 8102 becomes coaxial with the axis 8106 defined by the staple and blade portion 106. In this position, the ring 8102 may, if its outer diameter is less than the outer diameter of the staple and blade portion 106, contact the staple and blade portion 106 with its entire circumference as illustrated in FIG. 19(e). Thus, the sleeve 8100 may continue covering the staple and blade portion 106 during the surgical operation and may subsequently be employed, e.g., after the surgical procedure has been completed, to facilitate the removal the surgical attachment 100 from the oral passage. Alternatively, if the outer diameter of the ring 8102 is greater than the outer diameter of the staple and blade portion 106, continued movement of the sleeve 8100 relative to the surgical attachment may cause the ring 8102 to slide over the surgical attachment 100 for removal of the sleeve 8100 from the oral passage.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby and that its scope is to be determined by that of the appended claims.

The invention claimed is:

1. A method of at least one of cutting and stapling a section of tissue using a surgical attachment having an anvil and a housing, the method comprising:

mechanically attaching the anvil to the housing, the housing storing staples therein and being selectively movable relative a staple pusher;

connecting the housing to the staple pusher by a shear pin;

with a first driver, moving the anvil relative to the housing to an intermediate position between an open position and a closed position; and with a second driver, moving at least a portion of the housing relative to the anvil between the intermediate position and the closed position.

2. The method of claim 1, wherein moving the at least a portion of the housing relative to the anvil to the closed position includes clamping a section of tissue between a first clamping face of the anvil and a second clamping face of the housing.

3. The method of claim 2, further comprising driving, with the second driver, a cutting element between a retracted position and an extended position.

4. The method of claim 2, further comprising driving, with the second driver, a stapling element between a refracted position and an extended position.

5. The method of claim 2, further comprising driving, with the second driver, a staple cartridge axially within the housing between a refracted position and an extended position.

6. The method of claim 5, further comprising:
storing the staples within respective staple slots of the staple cartridge;
driving, with the second driver, the staple pusher; and
pushing, with the staple pusher, the staples into staple guides in the anvil.

7. The method of claim 2, further comprising axially locking the anvil relative to the housing in the intermediate position.

8. The method of claim 2, further comprising:
attaching the first and second drivers to respective rotatable drive shafts; and
selectively rotating the rotatable drive shafts by at least one motor.

9. The method of claim 8, wherein the selectively rotating step includes selectively rotating the rotatable drive shafts under the control of a controller.

10. A method for stapling a section of tissue, the method comprising:

storing staples in a housing, the housing being selectively movable relative to a staple pusher;
connecting the housing to the staple pusher by a shear pin; and
moving an anvil relative to the staple pusher and the housing, wherein moving the anvil causes the housing to move relative to the staple pusher.

11. The method of claim 10, wherein the moving of the anvil includes moving the anvil relative to the staple pusher between a first position, in which the anvil is spaced apart from a clamping surface of the housing, and a second position, in which the anvil contacts the clamping surface of the housing.

12. The method of claim 11, wherein the moving of the anvil includes moving the anvil relative to the staple pusher between the second position and a third position, in which the staples stored in the housing are pushed out of the housing by the staple pusher to be closed against the anvil.

13. The method of claim 12, wherein moving of the anvil between the second and the third position includes the housing being moved relative to the staple pusher.

14. The method of claim 10, further comprising:
with the anvil, applying a predetermined amount of pressure on the clamping surface of the housing; and
shearing the shear pin via a rotatable drive shaft connected to a motor, such that the anvil moves between the second and the third position.

15. The method of claim 14, further comprising aligning a plurality of staple slots of the housing with a corresponding plurality of pusher fingers extending from the staple pusher.

16. The method of claim 15, wherein moving the anvil relative to the housing and the staple pusher includes moving the anvil with a first driver.

17. The method of claim 16, further comprising, when the anvil is moved relative to the staple pusher between the second position and the third position, cutting with a cutting element tissue positioned between the anvil and the clamping surface of the housing.

* * * * *